US010585037B2

(12) United States Patent
Yanagi et al.

(10) Patent No.: US 10,585,037 B2
(45) Date of Patent: Mar. 10, 2020

(54) SUBSTANCE DETECTING DEVICE, SUBSTANCE DETECTING SYSTEM, AND SUBSTANCE DETECTING METHOD IN WHICH TEMPERATURE CONTROL OF LIGHT EMISSION IS PERFORMED

(71) Applicant: PANASONIC INTELLECTUAL PROPERTY MANAGEMENT CO., LTD., Osaka (JP)

(72) Inventors: Kazuhiro Yanagi, Kanagawa (JP); Keiji Hirata, Fukuoka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 106 days.

(21) Appl. No.: 15/751,353

(22) PCT Filed: Aug. 8, 2016

(86) PCT No.: PCT/JP2016/003636
§ 371 (c)(1),
(2) Date: Feb. 8, 2018

(87) PCT Pub. No.: WO2017/033419
PCT Pub. Date: Mar. 2, 2017

(65) Prior Publication Data
US 2018/0231460 A1 Aug. 16, 2018

(30) Foreign Application Priority Data

Aug. 24, 2015 (JP) .................................. 2015-165082
Sep. 29, 2015 (JP) .................................. 2015-191960
Oct. 27, 2015 (JP) .................................. 2015-211280

(51) Int. Cl.
*G01N 21/3504* (2014.01)
*G01N 21/27* (2006.01)
(Continued)

(52) U.S. Cl.
CPC ........ *G01N 21/3504* (2013.01); *G01J 3/0286* (2013.01); *G01J 3/0291* (2013.01);
(Continued)

(58) Field of Classification Search
CPC ............... G01N 21/3518; G01N 21/27; G01N 2201/0636; G01N 2201/0634;
(Continued)

(56) References Cited

U.S. PATENT DOCUMENTS 7,969,576 B1 * 6/2011 Buckley ................. G01N 21/39
356/437
2007/0131882 A1 6/2007 Richman
(Continued)

FOREIGN PATENT DOCUMENTS

JP 6-148071 A 5/1994
JP 7-151681 A 6/1995
(Continued)

OTHER PUBLICATIONS

U.S. Appl. No. 15/935,544 to Hiroshi Iwai et al., filed Mar. 26, 2018.
(Continued)

*Primary Examiner* — Michael P LaPage
(74) *Attorney, Agent, or Firm* — Greenblum & Bernstein, P.L.C.

(57) ABSTRACT

There is provided a substance detecting device emits first invisible light to the inside and the outside of a detection region of a substance, changes an emitting direction of the first invisible light inside and outside the detection region, receives third invisible light which is passing light of the first invisible light through the reference cell in which a detection target substance is stored, outside of the detection region, and adjusts a temperature of the first invisible light and
(Continued)

controls the wavelength of the first invisible light based on the wavelength characteristics of the third invisible light.

18 Claims, 53 Drawing Sheets

(51) Int. Cl.
G01J 3/06 (2006.01)
G01J 3/02 (2006.01)
G01J 3/10 (2006.01)
G01J 3/42 (2006.01)
G01J 3/433 (2006.01)

(52) U.S. Cl.
CPC . G01J 3/06 (2013.01); G01J 3/10 (2013.01); G01J 3/42 (2013.01); G01J 3/4338 (2013.01); G01N 21/27 (2013.01); *G01N 2021/3509* (2013.01)

(58) Field of Classification Search
CPC ...... G01N 21/3504; G01J 3/0286; G01J 3/42; G01J 3/10; G01J 3/06; G01J 3/0291
See application file for complete search history.

(56) References Cited

U.S. PATENT DOCUMENTS

| | | | |
|---|---|---|---|
| 2012/0113426 A1* | 5/2012 | Rao | G01J 3/4338 356/437 |
| 2013/0163000 A1* | 6/2013 | Ido | G01N 21/59 356/437 |
| 2014/0220700 A1* | 8/2014 | Alexander | G01N 21/59 436/164 |

FOREIGN PATENT DOCUMENTS

| | | |
|---|---|---|
| JP | 2002-196075 | 7/2002 |
| JP | 2003-315267 | 11/2003 |
| JP | 2005-077279 | 3/2005 |
| JP | 2005-106521 | 4/2005 |
| JP | 2007-240248 A | 9/2007 |
| JP | 2008-232920 | 10/2008 |
| JP | 2012-000147 | 1/2012 |
| JP | 2013-128185 | 6/2013 |
| JP | 2014-119323 | 6/2014 |
| JP | 2014-235103 | 12/2014 |

OTHER PUBLICATIONS

International Search Report (ISR) from International Searching Authority (Japan Patent Office) in International Pat. Appl. No. PCT/JP2016/003636, dated Oct. 25, 2016.

Communication pursuant to Rule 164(1) EPC from European Patent Office (EPO) dated Jul. 30, 2018 for the related European Patent Application No. 16838770.2.

Ben Russell Van Well: "A Portable Laser System for the Remote Detection of Methane Gas", Jan. 4, 2006 (Jan. 4, 2006), XP055492268, Retrieved from the Internet: URL: http://theses.gla.ac.uk/6145/1/2006.van%20Well.PhD.pdf [retrieved on Jul. 12, 2018].

M. B. Frish et al: "The next generation of TDLAS analyzers", Proceedings of SPIE, vol. 6765, Sep. 26, 2007 (Sep. 26, 2007), p. 676506, XP055492065.

* cited by examiner

FIG. 26
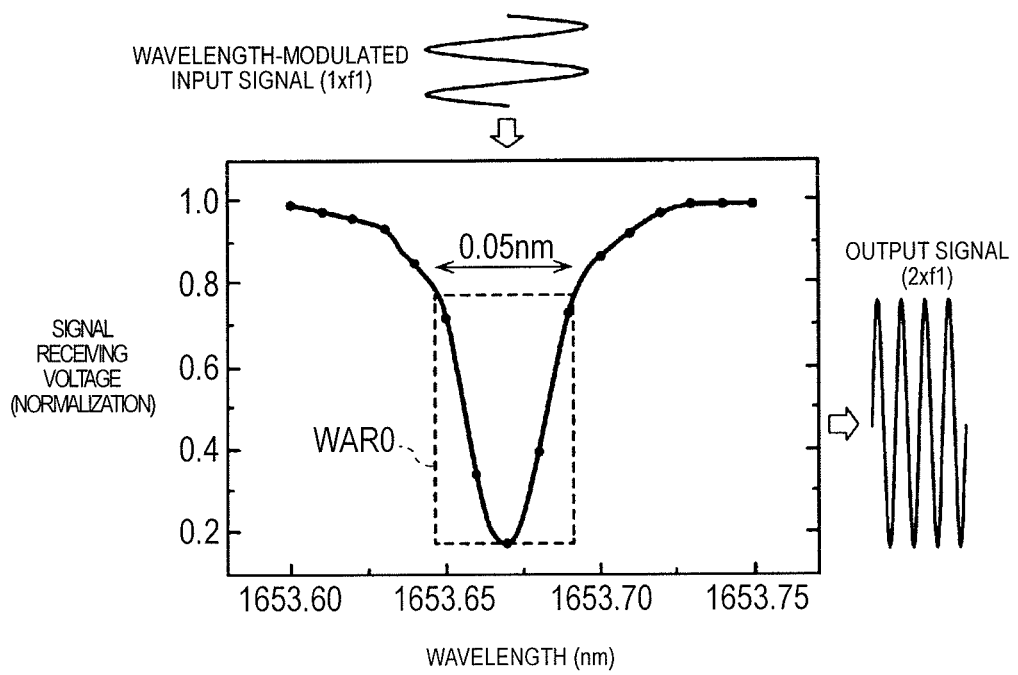
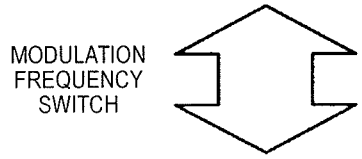
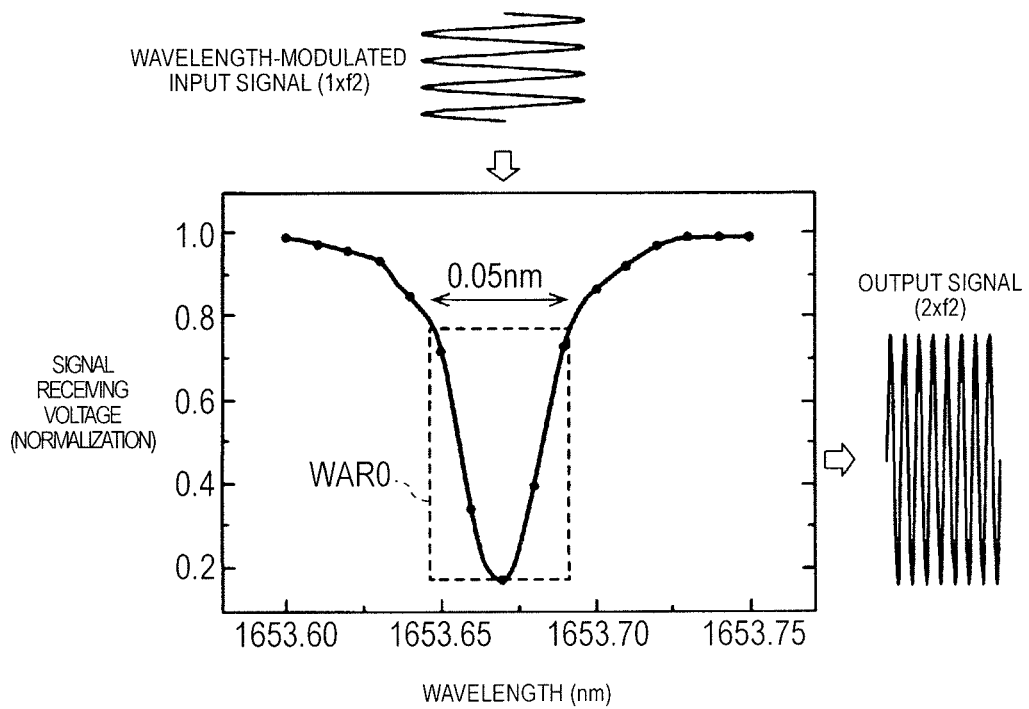

FIG. 28
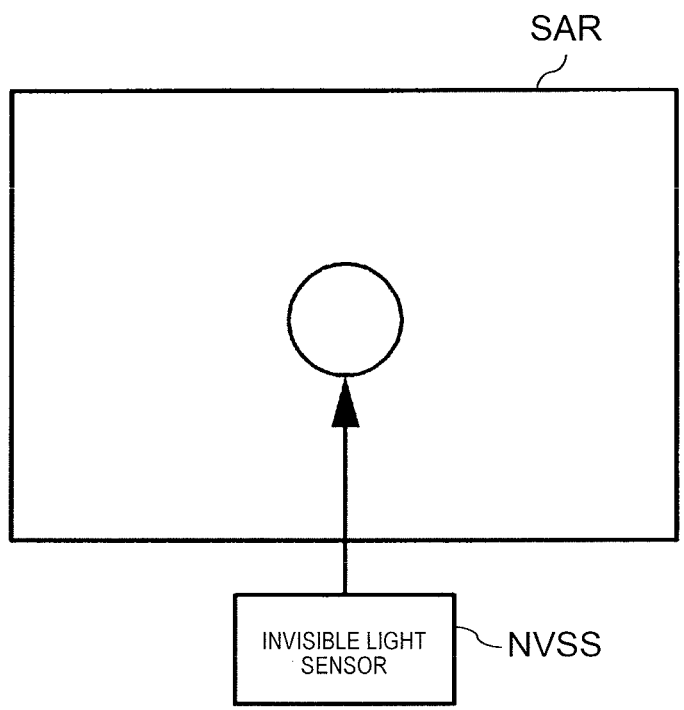
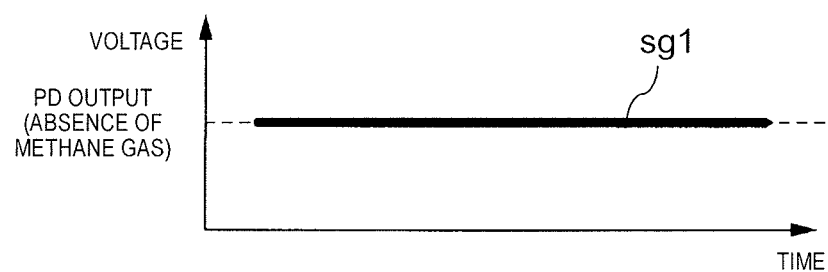
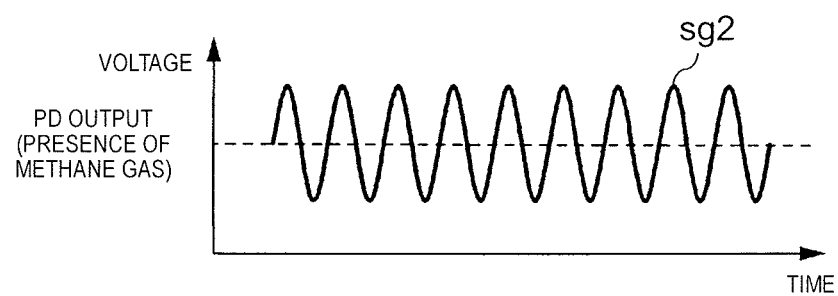

FIG. 29
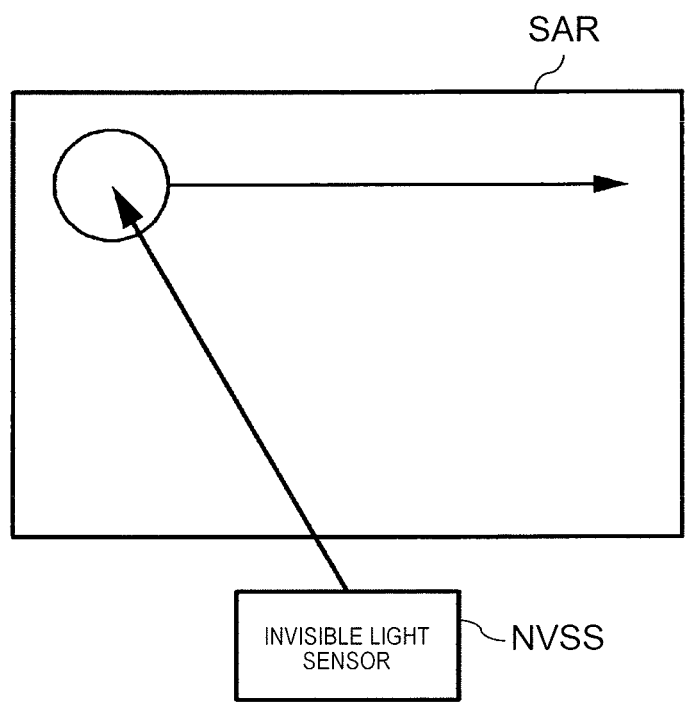
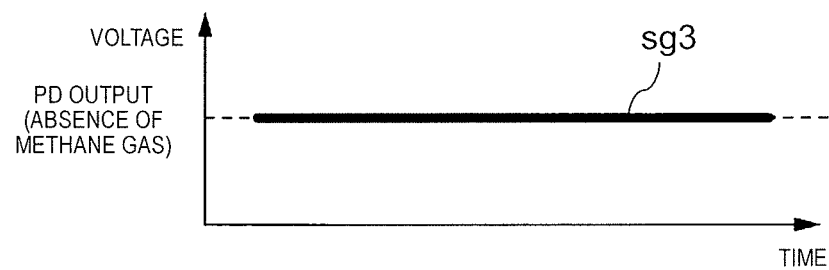
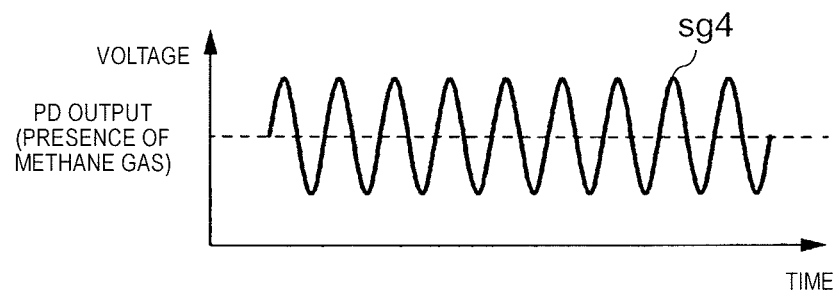

FIG. 30
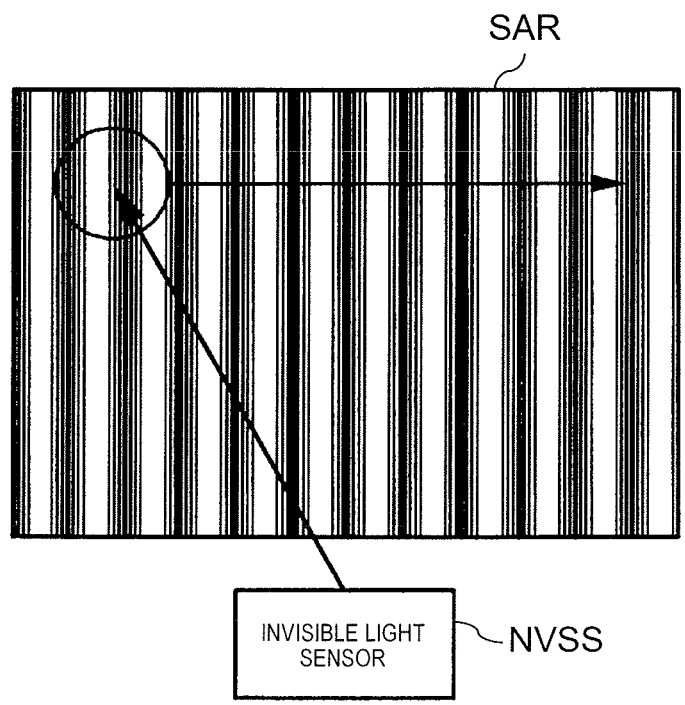
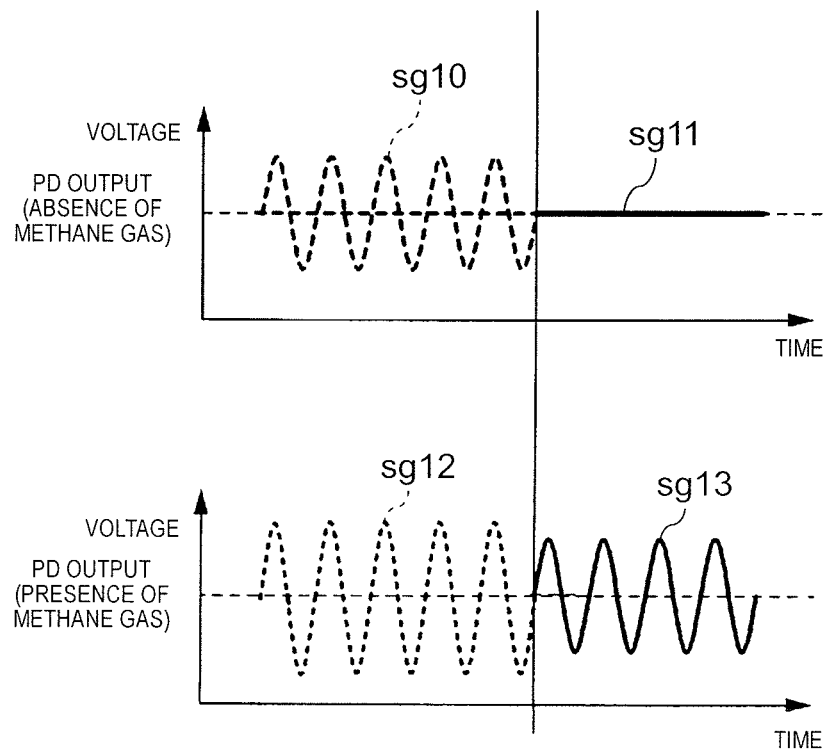

FIG. 42
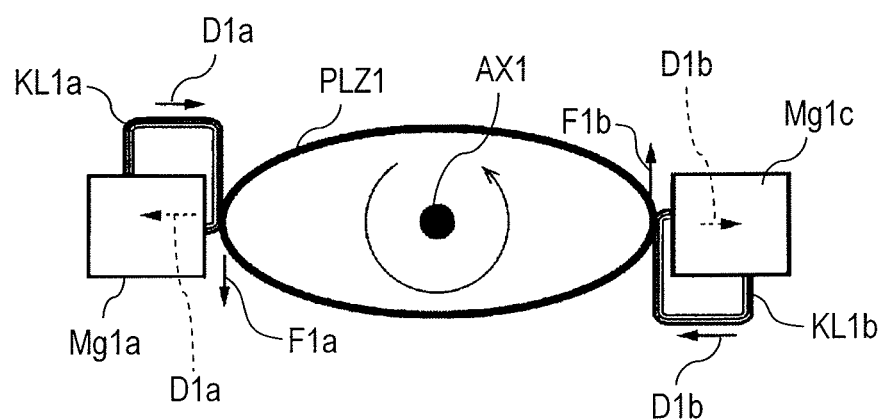
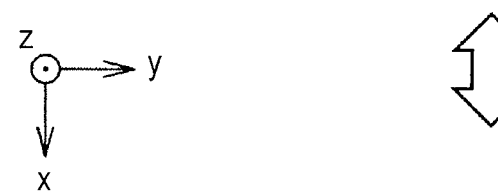
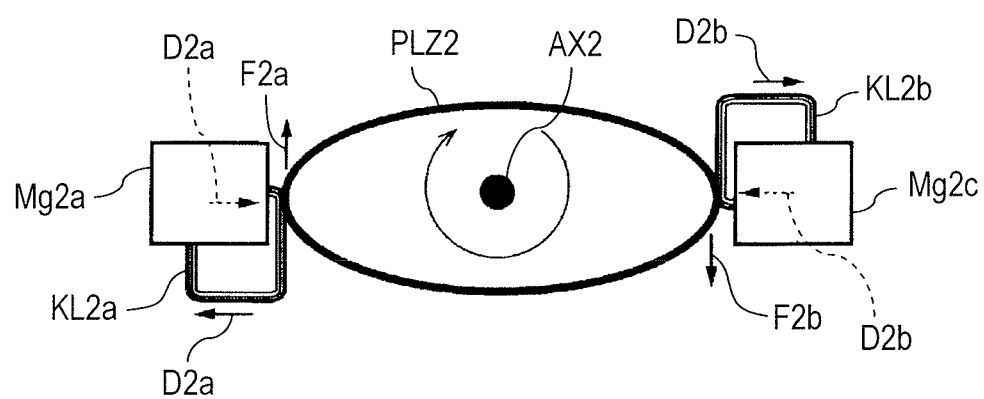

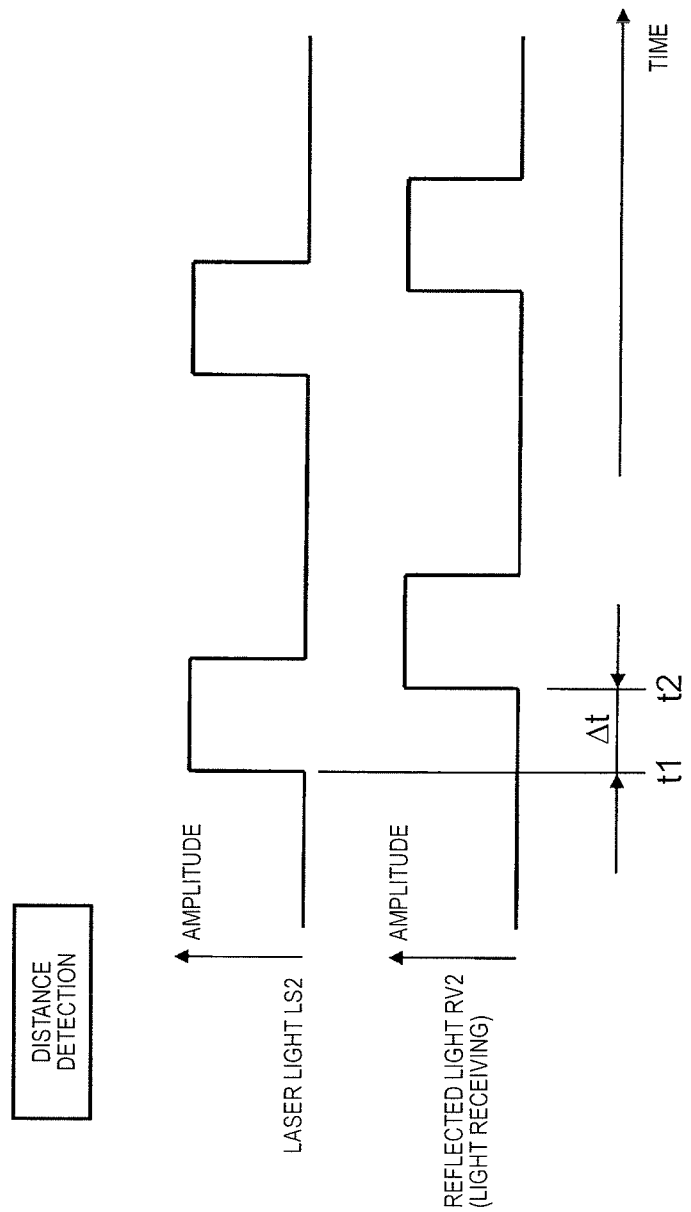

SUBSTANCE DETECTING DEVICE, SUBSTANCE DETECTING SYSTEM, AND SUBSTANCE DETECTING METHOD IN WHICH TEMPERATURE CONTROL OF LIGHT EMISSION IS PERFORMED

TECHNICAL FIELD

This disclosure relates to a substance detecting device, a substance detecting system, and a substance detecting method of detecting a substance that is difficult to be visible through imaging with visible light in a detection region.

BACKGROUND ART

As a device that detects a substance (for example, a gas) which is difficult to be visible by performing imaging with visible light in a detection region in the prior art, a gas concentration measuring device that emits measurement light from a semiconductor laser toward a measurement environment has been known (for example, see PTL 1).

The gas concentration measuring device in PTL 1 emits, from a semiconductor laser unit, the measurement light subjected to frequency stabilization with a gas absorption line and causes a light receiver to receive reflected measurement light reflected from the measurement environment with the emission of the measurement light. The gas concentration measuring device detects a fundamental wave phase-sensitive detection signal and a second harmonic phase-sensitive detection signal having a modulation frequency of a semiconductor laser from an output signal of the light receiver and measures a gas concentration of the measurement environment based on a ratio of both signals. In addition, in the semiconductor laser unit of the gas concentration measuring device, the light receiver is disposed deep inside on a center axis line in a bottomed main body having a cylindrical shape. A semiconductor laser module including a semiconductor laser, a laser pointer that emits visible light as guide light, and combination wave means, which is disposed on an optical axis of a light receiving device and substantially coaxially combines the measurement light that is emitted from the semiconductor laser and guide light that is emitted from the laser pointer, are installed in the main body. In this manner, the gas concentration measuring device is capable of checking an emission position of the measurement light and emitting the measurement light toward a measurement position with accuracy.

In addition, a gas detecting device that performs gas detection on a predetermined point has been known (see PTL 2). The gas detecting device causes laser light emitted from a laser diode (LD) module to diverge into measurement light and reference light with a half mirror. The measurement light is used for the gas detection. The reference light is received by a wavelength processing light receiver after passing through a gas cell. A wavelength processing controller performs a wavelength checking process or a wavelength correcting process of the LD module based on a detection signal obtained by the received reference light.

In this disclosure, it is possible to easily detect a substance in a detection region. Hence, in this disclosure, it is possible to easily detect, with fine resolution, a substance that is difficult to be visible through imaging with visible light in the detection region, without significant effort of a user.

CITATION LIST

Patent Literature

PTL 1: Japanese Patent Unexamined Publication No. 2005-106521
PTL 2: Japanese Patent Unexamined Publication No. 2008-232920

SUMMARY OF THE INVENTION

According to this disclosure, there is provided a substance detecting device including: a transmitter that emits first invisible light to the inside and the outside of a detection region of a substance; a first receiver that receives second invisible light which is reflected light of the first invisible light from the substance, inside the detection region; a detector that detects the substance, based on wavelength characteristics of the second invisible light; an actuator that changes an emitting direction of the first invisible light and a receiving direction of the second invisible light, inside and outside the detection region; a reference cell in which a detection target substance is stored, outside the detection region; a second receiver that receives third invisible light which is passing light of the first invisible light through the reference cell; and a wavelength controller that adjusts a temperature of the first invisible light and controls the wavelength of the first invisible light based on the wavelength characteristics of the third invisible light.

According to this disclosure, it is possible to easily detect the substance in the detection region.

In addition, according to this disclosure, there is provided a substance detecting device including: a transmitter that performs wavelength modulation and emits first invisible light to the inside of a detection region of a substance; a receiver that receives second invisible light which is reflected light of the first invisible light from the substance, inside the detection region; a detector that detects the substance, based on wavelength characteristics of the second invisible light; an actuator that changes an emitting direction of the first invisible light and a receiving direction of the second invisible light, inside the detection region; and a controller that changes a modulation frequency which is a frequency of wavelength modulation of the first invisible light and a detection frequency corresponding to the modulation frequency for detecting the substance by the detector.

According to this disclosure, it is possible to improve accuracy of the detection of the substance inside the detection region.

In addition, according to this disclosure, there is provided a substance detecting device including: a first light source that emits, to a detection area, first light having a wavelength for substance detection; a second light source that emits, to the detection area, second light having a wavelength for distance measurement; a distance measurer that measures a distance to an irradiation position, based on reflected light of the second light which is obtained after the second light is reflected at the irradiation position in the detection area; a gain adjustor that adjusts output gain of the first light in response to a measurement result from the distance measurer; and a substance detector that detects the presence or absence of the substance inside the detection area, based on the reflected light of the first light which is obtained after the first light subjected to adjustment of the output gain by the gain adjustor is reflected at the irradiation position. In scanning with the first light and the second light inside the detection area, an irradiation position that is irradiated with the second light is irradiated temporally ahead of an irradiation position that is irradiated with the first light.

According to this disclosure, it is possible to easily detect, with fine resolution, a substance that is difficult to be visible through imaging with visible light in the detection region, without significant effort of a user.

BRIEF DESCRIPTION OF DRAWINGS

FIG. 26 is a schematic diagram illustrating an input signal and an output signal of laser light in a case where the laser light emitted from a laser diode has the optimal wavelength with respect to absorption spectra of a specific substance.

FIG. 28 is a diagram for illustrating an example of spot detection in a substance detecting operation.

FIG. 29 is a schematic diagram for illustrating an example of area detection in a case where there is no background change in the substance detecting operation.

FIG. 30 is a schematic diagram for illustrating an example of area detection in a case where there is a background change in the substance detecting operation.

FIG. 42 is a diagram illustrating an example of driving of the collimator lens when viewed from above (in a −z direction) in FIG. 41.

FIG. 48 is a timing chart for illustrating an example of a distance detecting method in the detection camera of the fifth embodiment.

DESCRIPTION OF EMBODIMENTS

Hereinafter, embodiments of this disclosure will be described in detail with reference to the accompanying figures. However, the detailed description that is more than necessary is omitted in some cases. For example, the detailed description of a well-known subject or repetitive description of the same configuration is omitted in some cases, in order to avoid unnecessarily redundant description and in order for those skilled in the art to achieve easy understanding. The accompanying figures and the following description are provided to make those skilled in the art sufficiently understand this disclosure and are not provided to limit subjects according to claims.

Substance detecting devices of embodiments detect a substance by using an invisible light sensor. This disclosure can also be represented as a substance detecting method in which the invisible light sensor performs operations.

First Embodiment

Figure 1:
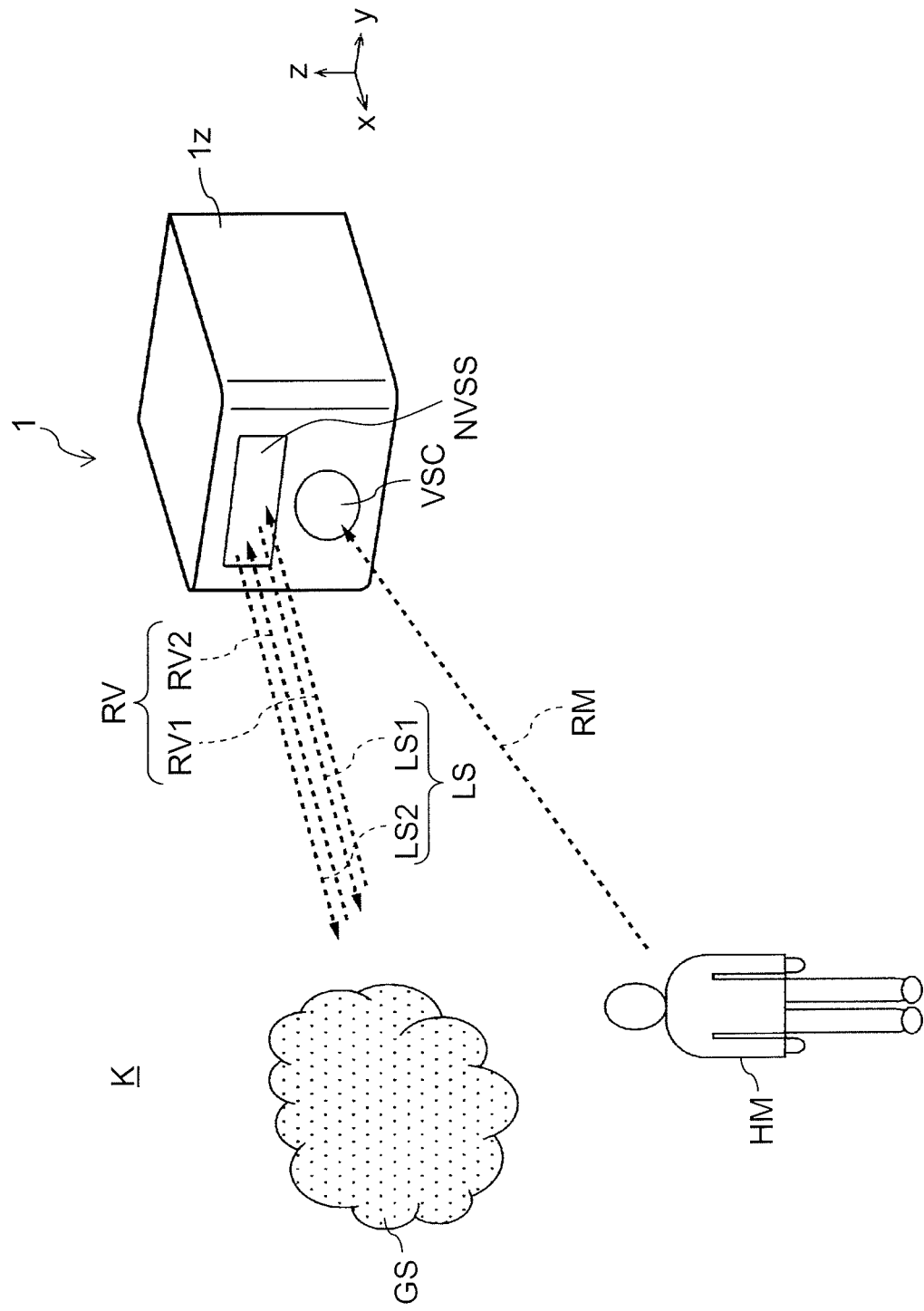
FIG. 1 is a schematic diagram illustrating an outline of a detection camera including an invisible light sensor of a first embodiment.

FIG. 1 is a schematic diagram illustrating an outline of detection camera 1 including invisible light sensor NVSS of a first embodiment. Detection camera 1 is configured to include visible light camera VSC and invisible light sensor NVSS.

For example, similar to an existing inspection camera, visible light camera VSC captures a human HM or an object that is present in detection space K as an example of a predetermined detection area by using reflected light RM which is visible light having a predetermined wavelength (for example, 0.4 to 0.7 μm). Hereinafter, image data obtained from capturing by visible light camera VSC is referred to as "visible light camera image data". As described above, detection camera 1 includes both configurations of invisible light sensor NVSS that detects invisible light and visible light camera VSC that obtains the visible light camera image data from the capturing.

Invisible light sensor NVSS optically scans emission of laser light with which it is possible to irradiate a position (hereinafter, referred to as an irradiation position) having a finite area with a predetermined diameter in the same detection space K as that of visible light camera VSC, thereby projecting laser light LS which is invisible light (for example, infrared light) having a predetermined wavelength. Projected laser light LS is light having a wavelength in a wavelength band that is easily absorbed into a detection target substance (referred to as a specific substance), specifically, having a wavelength in a wavelength band that is easily absorbed into detection target gas in a fifth embodiment.

Invisible light sensor NVSS receives reflected light of laser light LS from a detection target object (for example, gas GS such as methane gas as the specific substance) or reflected light (that is, reflected light RV) from a reflective object in a detection space after passing through the detection target object and determines whether or not a specific substance (for example, a gas) is detected in detection space K, based on a received light intensity of the reflected light RV which is received.

The specific substance, of which detection is determined by invisible light sensor NVSS, is a substance that is difficult to be discriminated by visible light camera VSC based on the visible light camera image data (that is, a substance that is unlikely to be visible by a person from capturing by the existing inspection camera). The specific substance may be a transparent liquid such as water or a transparent solid such as ice, in addition to a gas, and there is no particular limitation to the specific substance. As described above, a case where the detection target substance is gas GS will be described, hereinafter.

In addition, detection camera 1 generates and outputs display data obtained by synthesizing output image data (hereinafter, referred to as "substance position image data") including determination results of the detection of the specific substance which is generated by invisible light sensor NVSS or information (a name or the like of a substance) associated with the substance position image data to the visible light camera image data captured by visible light camera VSC.

Figure 45:
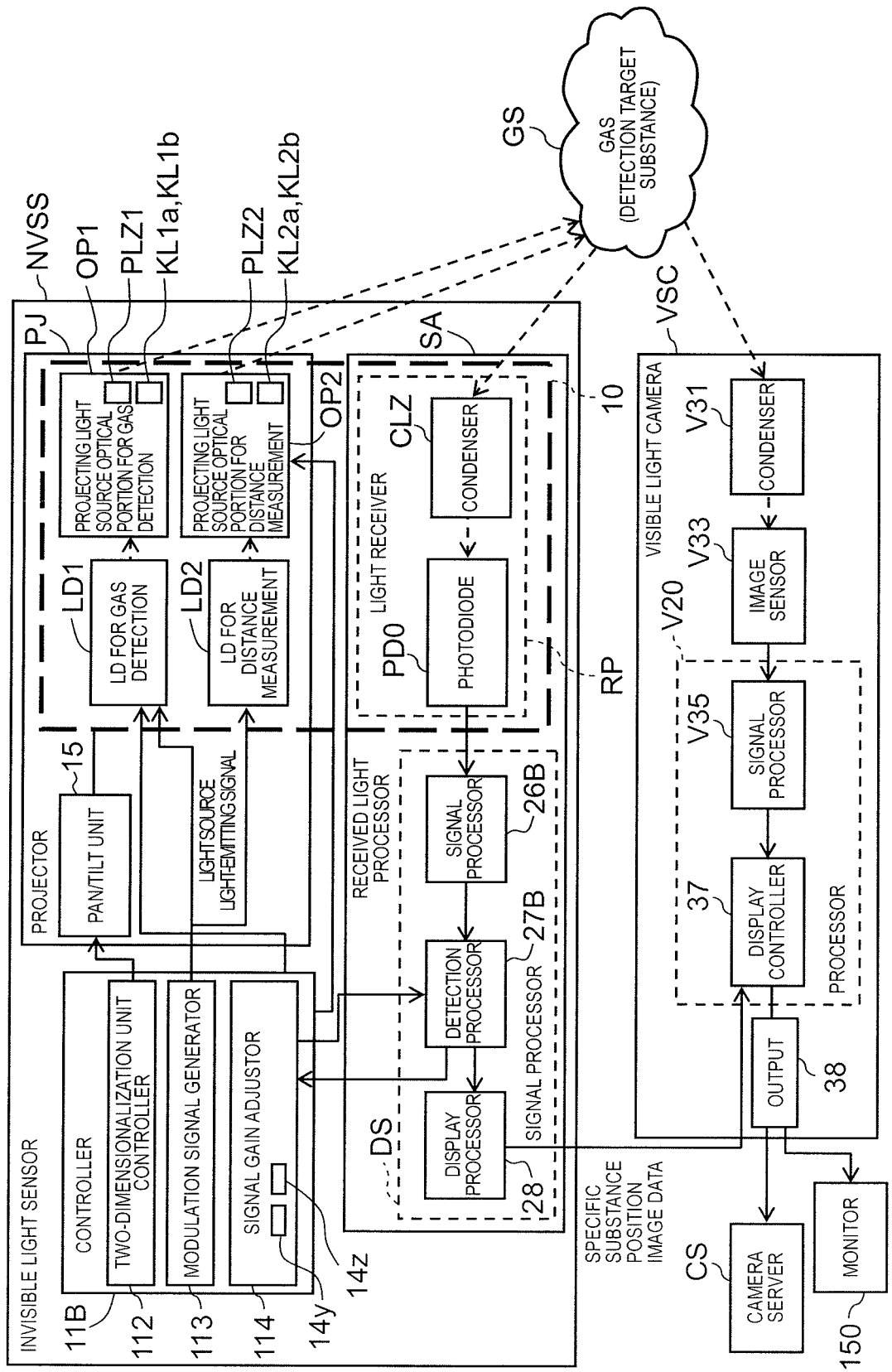
FIG. 45 is a block diagram illustrating an example of an internal configuration of the detection camera in the fifth embodiment in detail.

An output target of the display data from detection camera 1 is an externally connected device that is connected to detection camera 1 via a network and, for example, camera server CS or monitor 150 illustrated in FIG. 45. A gas detecting system of the fifth embodiment may be configured to include detection camera 1 and monitor 150 or may be configured to include detection camera 1 and camera server CS. Here, the network may be a wired network (for example, Intranet or Internet) or may be a wireless network (for example, a wireless local area network (LAN)).

Figure 2:
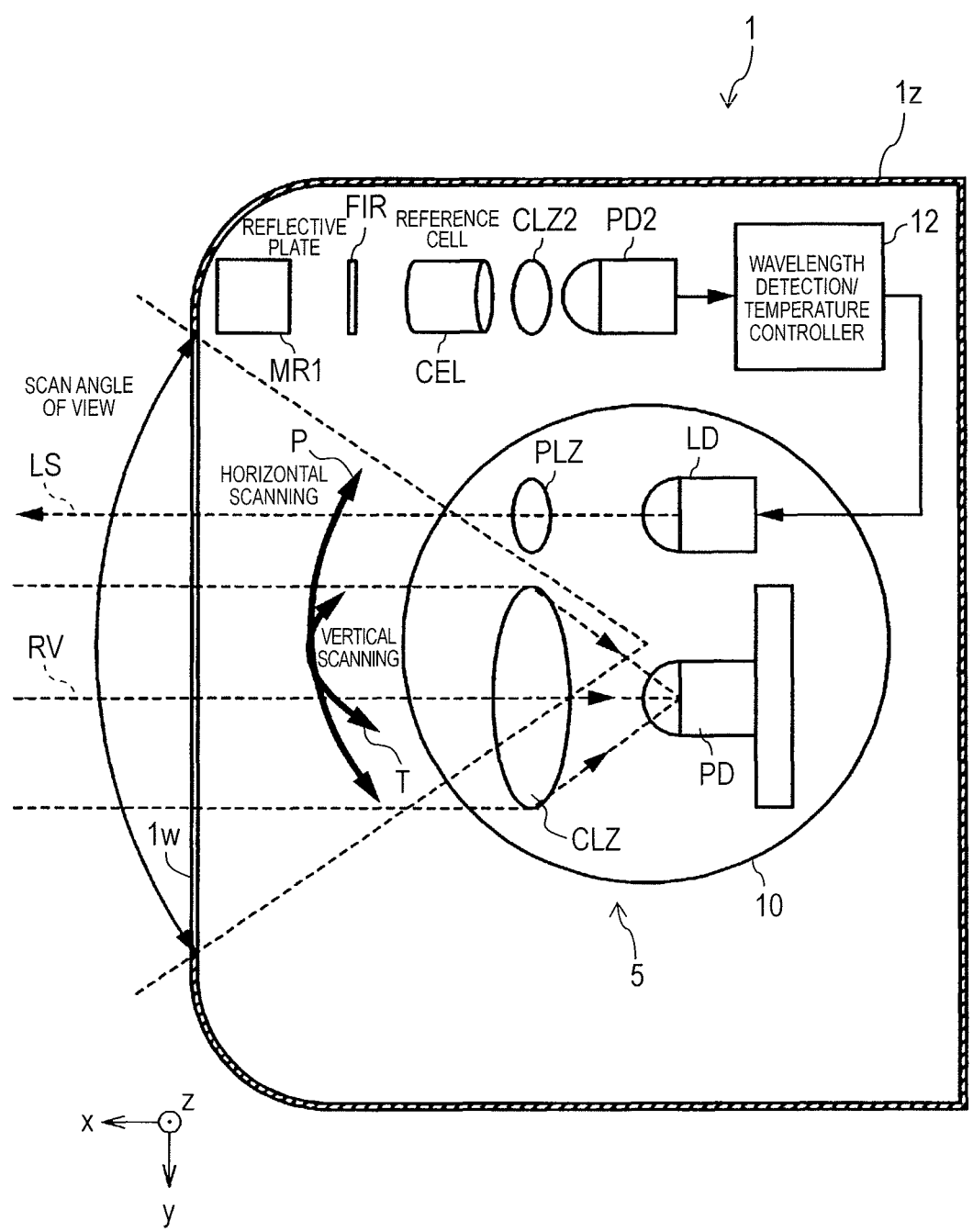
FIG. 2 is a schematic diagram illustrating an example of an internal configuration of the detection camera.

FIG. 2 is a schematic diagram illustrating an internal configuration of detection camera 1. FIG. 2 illustrates the internal configuration of detection camera 1 when viewed from above in FIG. 1 (downward in a z-axis direction).

For example, detection camera 1 includes box-shaped housing 1z. Opening 1w for invisible light sensor NVSS is formed in a side surface of housing 1z. Transparent glass or resin may be fit in opening 1w for water proof/dust proof. In addition, condenser V31 of visible light camera VSC is exposed from the side surface of housing 1z.

Sensor scanning unit 5 is provided inside housing 1z. Sensor scanning unit 5 has camera platform 10, which freely swivels in a pan direction (direction parallel to an xy plane in the figure) represented by an arrow P in the figure and in a tilt direction (z-axis direction in the figure) represented by an arrow T in the figure, and pan/tilt unit 15 including a motor mechanism that drives camera platform 10.

On camera platform 10, laser diode LD, collimator lens PLZ, photodiode PD, and condenser CLZ are mounted. Pan/tilt unit 15 causes camera platform 10 to swivel in the pan direction and the tilt direction, thereby making it possible to perform two-dimensional scanning (horizontal scanning and vertical scanning) in detection region SAR by using laser light that is emitted from laser diode LD.

Laser light LS emitted from laser diode LD is transmitted through collimator lens PLZ so as to be parallel light and is emitted toward detection space K. Laser light (reflected light) RV reflected from gas GS in detection space K is incident through opening 1w formed in housing 1z of detection camera 1, is condensed by condenser CLZ, and is received by photodiode PD.

The presence or absence of gas GS as the detection target substance which is present in detection space K is determined from absorption spectra (absorption characteristic) of the laser light received by photodiode PD. For example, detection region SAR that is a range (scan angle of view) in which it is possible to perform scanning in detection space K with laser light LS emitted from laser diode LD is set depending on the shape of opening 1w formed in housing 1z.

Here, laser diode LD is likely to be influenced by a temperature, and a wavelength of the laser light which is emitted from laser diode LD is shifted due to a slight change in temperature. Therefore, invisible light sensor NVSS performs temperature control (control for regulating a temperature) such that the wavelength (center wavelength in wavelength modulation) of the laser light is not changed during an operation of gas detection and the temperature of laser diode LD is maintained to be constant.

In order to perform the temperature control, reflective plate MR1, reference cell CEL, condenser CLZ2, photodiode PD2 for temperature control, and wavelength detection/temperature controller 12 are disposed inside housing 1z. Neutral density filter (ND filter) FIR may be disposed between reflective plate MR1 and reference cell CEL, and intensity of the laser light that is transmitted through reference cell CEL and is received by photodiode PD2 for the temperature control may be attenuated.

Figure 3:
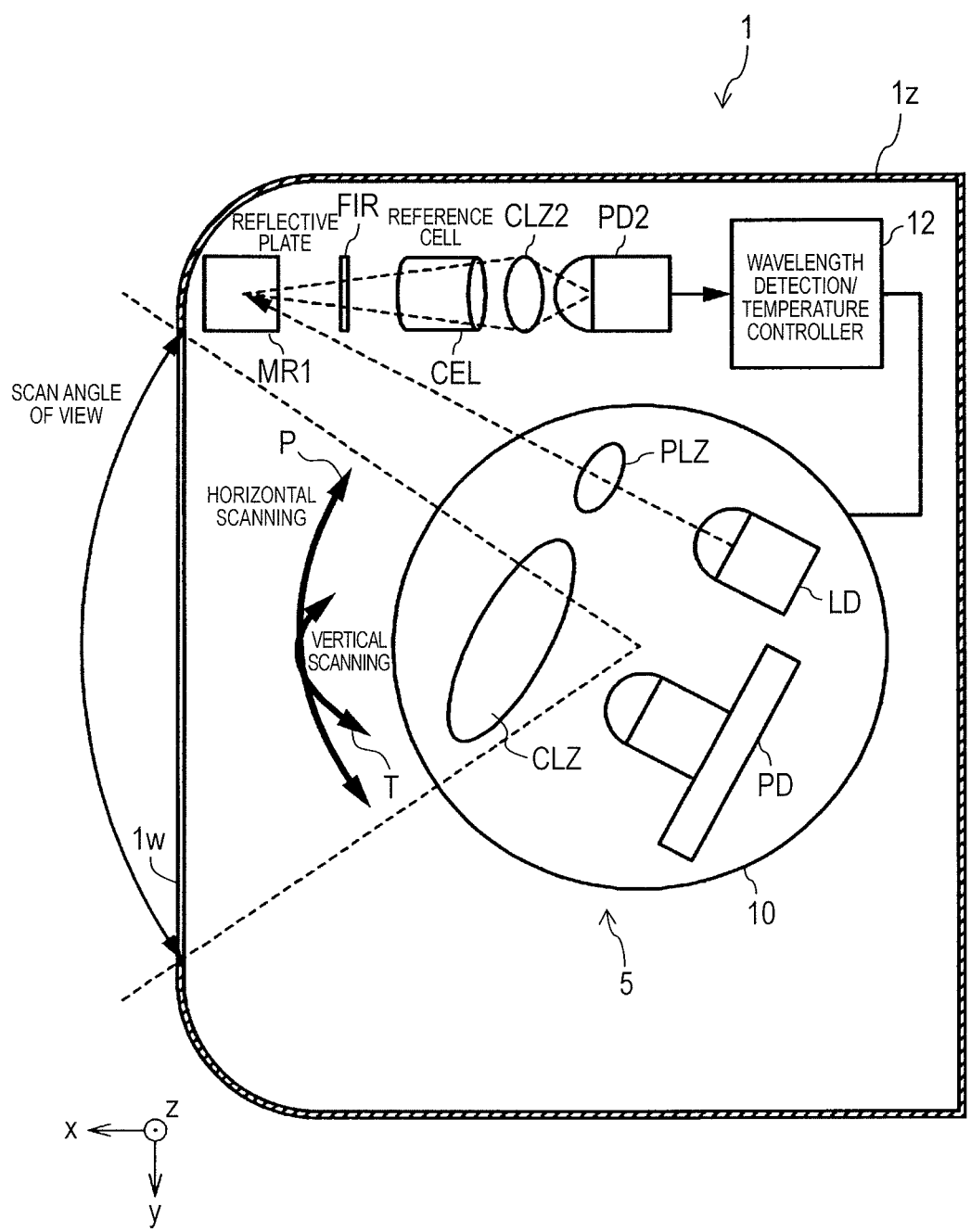
FIG. 3 is a schematic diagram illustrating an example of an internal operation of the detection camera during temperature control.

FIG. 3 is a schematic diagram illustrating an internal operation of detection camera 1 during temperature control.

In the temperature control, camera platform 10 significantly swivels in the pan direction, and the laser light emitted from laser diode LD travels toward reflective plate MR1. When laser diode LD mounted on camera platform 10 performs scanning with the laser light, reflective plate MR1 is disposed at a position out of a range in which photodiode PD can receive the light, that is, out of the scan angle of view. Here, reflective plate MR1 is positioned to be close to opening 1w on the rear side of housing 1z. As described above, the range in which photodiode PD can receive the light is determined depending on the shape of opening 1w formed in housing 1z. In other words, reflected laser light RV through opening 1w in the scan angle of view is received by photodiode PD.

Figure 4:
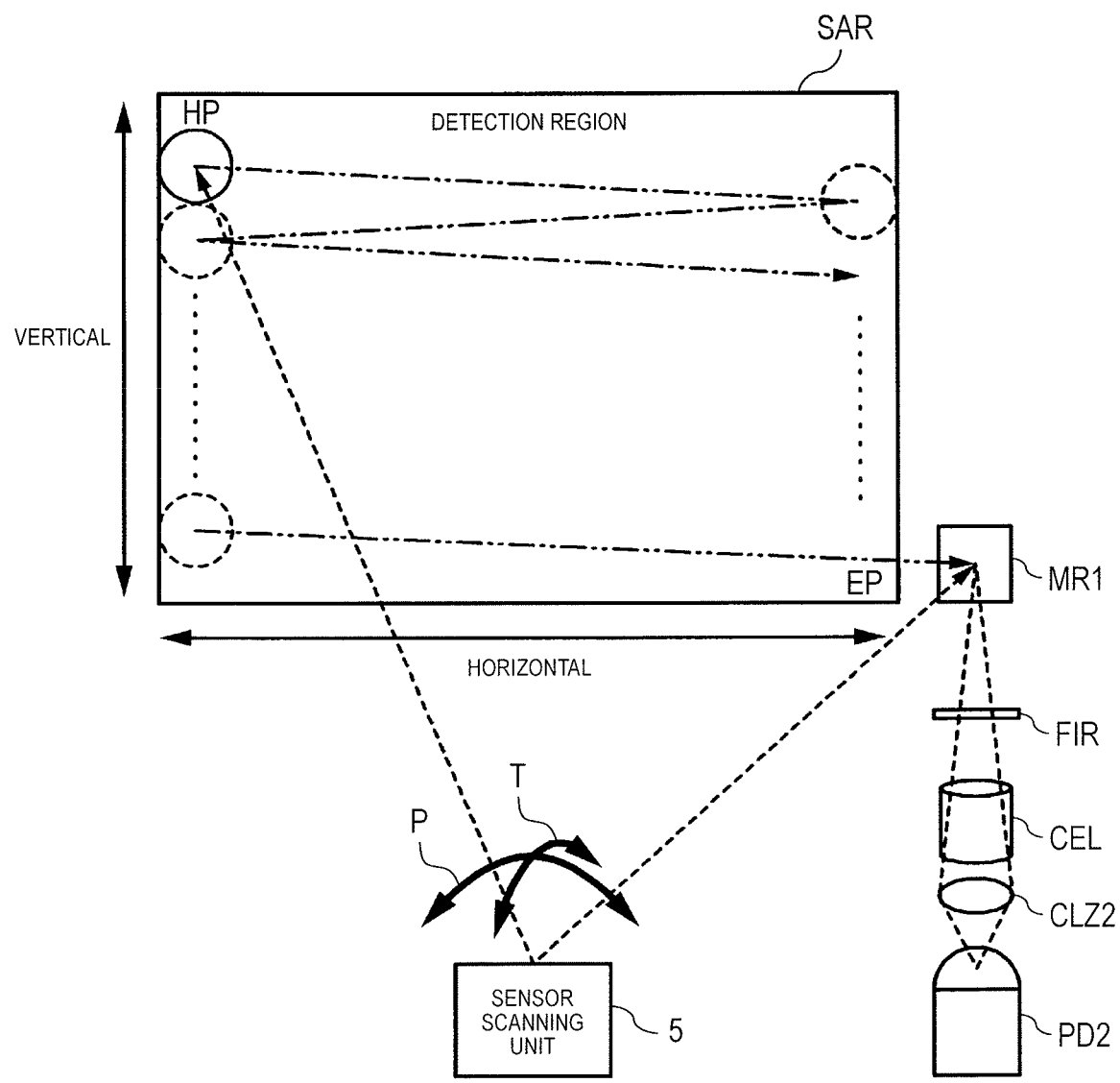
FIG. 4 is a schematic diagram illustrating an example of scanning a region including a detection region by a sensor scanning unit.

FIG. 4 is a schematic diagram illustrating the scanning of a region including detection region SAR by sensor scanning unit 5.

The swivel of camera platform 10 enables sensor scanning unit 5 to scan a space within the scan angle of view (detection region SAR) in the pan direction (horizontal direction) and the tilt direction (vertical direction) by using laser light LS emitted from laser diode LD mounted on camera platform 10. Reflective plate MR1 is disposed at a position beyond scan end position EP in the horizontal direction, at which one scan of the inside of detection region SAR with the laser light is ended and the laser light has yet to return to initial position HP.

In the temperature control, the laser light emitted from laser diode LD is reflected from reflective plate MR1 and passes through ND filter FIR. The laser light is transmitted through reference cell CEL, in which gas that is the detection target substance is sealed (stored), is condensed by condenser CLZ2, and is received by photodiode PD2 for temperature control. The gas sealed in reference cell CEL has the same components as those of the detection target gas GS.

Figure 6:
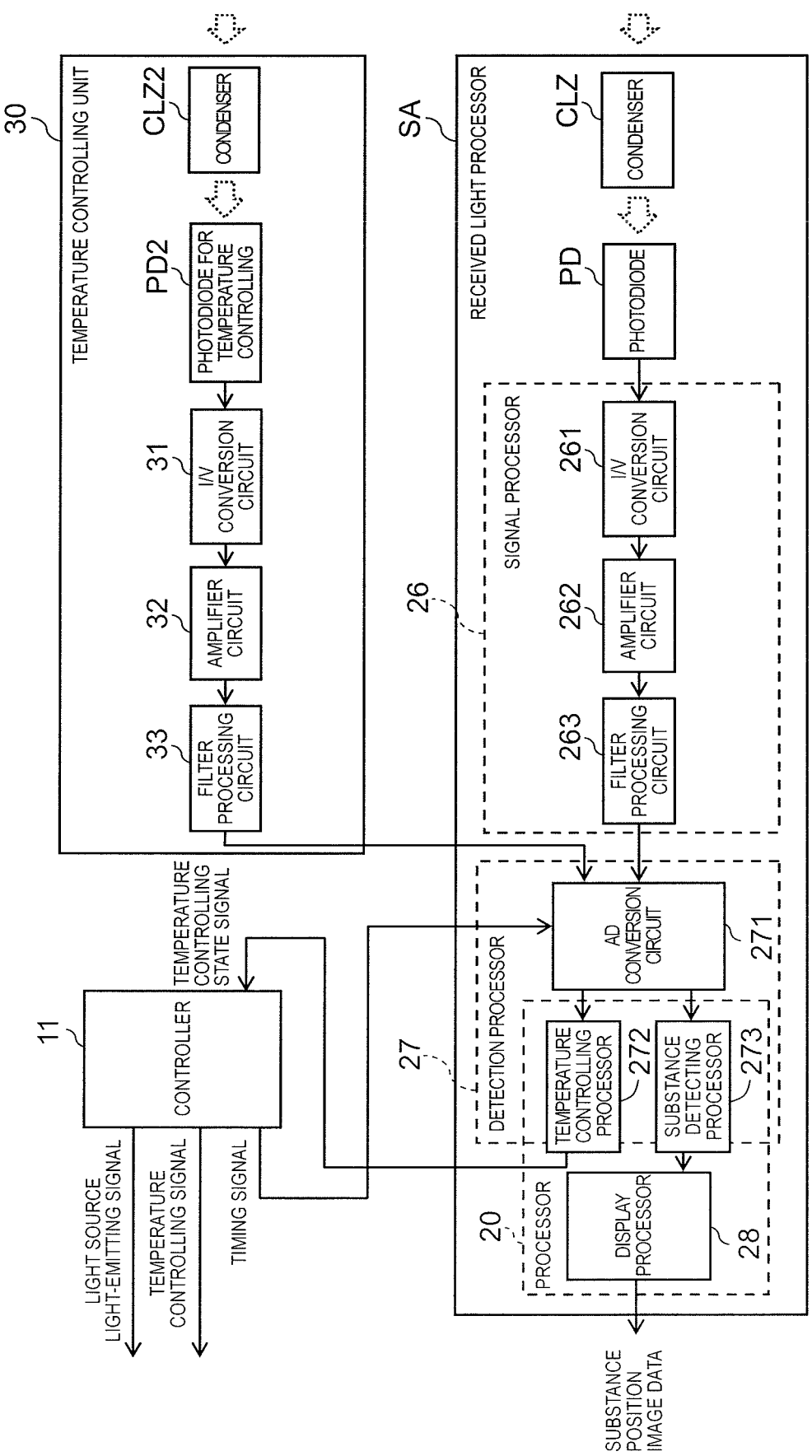
FIG. 6 is a block diagram illustrating an example of a configuration of a temperature controlling unit and a received light processor.

For example, wavelength detection/temperature controller 12 includes AD conversion circuit 271 and temperature controlling processor 272 in detection processor 27 and controller 11 illustrated in FIG. 6. Wavelength detection/temperature controller 12 detects the center wavelength of the laser light that is subjected to wavelength modulation to a predetermined width, based on a detection signal output from photodiode PD2 for the temperature control, and controls the temperature of laser diode LD at a constant temperature such that the center wavelength is not shifted.

Laser diode LD includes Peltier element Pt that absorbs and emits heat. Wavelength detection/temperature controller 12 may regulate the temperature of laser diode LD by supplying a predetermined current to Peltier element Pt internally provided in laser diode LD.

Laser diode LD may include a thermistor. In this case, wavelength detection/temperature controller 12 may regulate the temperature of laser diode LD by using the thermistor or by using Peltier element Pt and the thermistor.

In addition, in housing 1z, an electronic board is internally provided as a part of invisible light sensor NVSS, in which a processor 20 and controller 11 that collectively controls members are installed.

Figure 5:
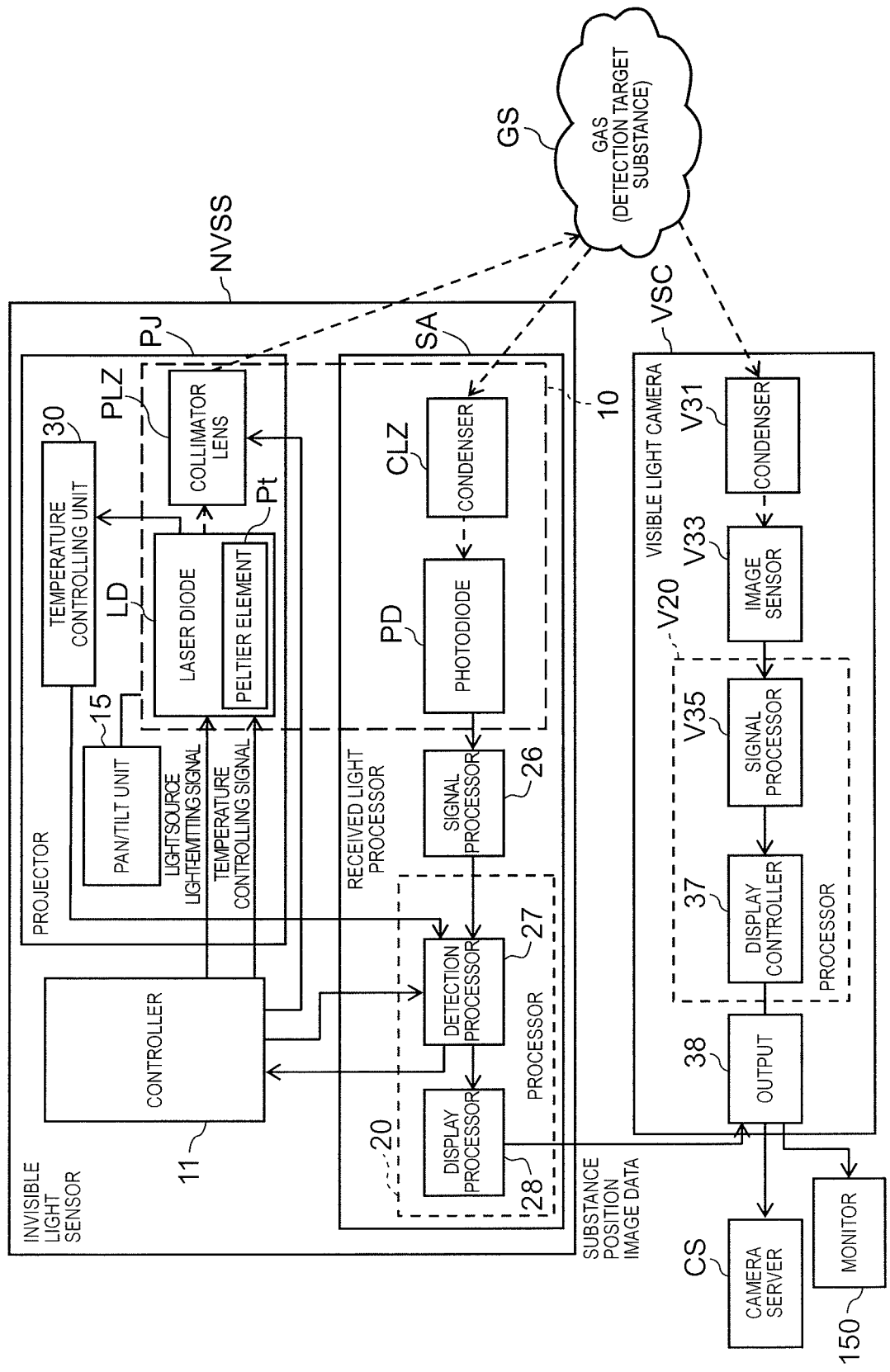
FIG. 5 is a block diagram illustrating an example of a configuration of the detection camera.

FIG. 5 is a block diagram illustrating a configuration of detection camera 1. As described above, detection camera 1 is configured to include invisible light sensor NVSS and visible light camera VSC. Invisible light sensor NVSS is configured to include controller 11, projector PJ, and received light processor SA.

Controller 11 is configured by using a central processing unit (CPU), a micro processing unit (MPU), or a digital signal processor (DSP). For example, controller 11 performs signal processing for overall control of operation control of the members of invisible light sensor NVSS, input/output processing of data with the other members, arithmetic processing of data, and storage processing of data. In addition, controller 11 sets, to detection processor 27, detection threshold M for detecting the specific substance as the detection target of invisible light sensor NVSS.

In addition, controller 11 transmits a timing signal for performing AD conversion to detection processor 27. Controller 11 transmits, to laser diode LD, a light source controlling signal for modulating the laser light that is emitted from laser diode LD.
Controller 11 transmits, to laser diode LD, a temperature controlling signal for controlling the temperature of laser diode LD.

Projector PJ includes laser diode LD, collimator lens PLZ, pan/tilt unit 15, and temperature controlling unit 30.

Laser diode LD emits laser light having an adjusted wavelength such that the wavelength of the laser light is equal to the peak of an absorption wavelength band of gas GS which is the detection target substance. Here, an example of the gas which is the detection target substance includes methane gas (CH4).

The wavelength is adjusted by using various types of methods.
For example, controller 11 modulates a drive current of laser diode LD in response to the light source controlling signal described above, thereby performing wavelength modulation of the laser light that is emitted from laser diode LD. In addition, Peltier element Pt provided in laser diode LD absorbs or emits heat in response to the temperature controlling signal from controller 11 and changes the temperature of laser diode LD, thereby adjusting the center wavelength of the wavelength modulation of the laser light.

Collimator lens PLZ changes laser light LS emitted from laser diode LD into parallel light.

Pan/tilt unit 15 swivels camera platform 10 in the pan direction and the tilt direction, on which laser diode LD, collimator lens PLZ, condenser CLZ, and photodiode PD are mounted. Pan/tilt unit 15 performs two-dimensional scanning within a scanning range including detection region SAR by using the laser light that is emitted from laser diode LD.

FIG. 6 is a block diagram illustrating a configuration of temperature controlling unit 30 and received light processor SA.

Temperature controlling unit 30 includes condenser CLZ2, photodiode PD2, I/V conversion circuit 31, an amplifier circuit 32, and a filter processing circuit 33.

Condenser CLZ2 condenses laser light which is emitted from laser diode LD, is reflected from reflective plate MR1, and is transmitted through reference cell CEL, and the laser light is received by photodiode PD2. Photodiode PD2 generates electric charges corresponding to the intensity of the received laser light and outputs the electric charges as a current signal.

I/V conversion circuit 31 converts the current signal output from photodiode PD2 into a voltage signal. Amplifier circuit 32 amplifies the voltage signal output from I/V conversion circuit 31. Filter processing circuit 33 performs filter processing on the signal amplified in amplifier circuit 32, and the filtered signal is output as a signal, which is used for the temperature control, to AD conversion circuit 271 in detection processor 27.

Received light processor SA includes condenser CLZ, photodiode PD, signal processing unit 26, detection processor 27, and display processor 28. Signal processing unit 26 includes I/V conversion circuit 261, amplifier circuit 262, and filter processing circuit 263.
Detection processor 27 includes AD conversion circuit 271, temperature controlling processor 272, and substance detection processor 273. Processor 20 executes a program stored in the memory, and thereby the functions of temperature controlling processor 272 and substance detection processor 273 of detection processor 27 and display processor 28 are realized.

Condenser CLZ condenses laser light which is emitted from laser diode LD and is reflected from a specific substance in detection region SAR, and the condensed laser light is received by photodiode PD. Photodiode PD generates electric charges corresponding to the intensity of the received laser light and outputs the electric charges as a current signal.

I/V conversion circuit 261 converts the current signal output from photodiode PD into a voltage signal. Amplifier circuit 262 amplifies the voltage signal output from I/V conversion circuit 261. Filter processing circuit 263 performs filter processing on the signal amplified in amplifier circuit 262, and the filtered signal is output as a signal, which is used for the substance detection, to AD conversion circuit 271 in detection processor 27.

AD conversion circuit 271 in detection processor 27 converts a signal input from temperature controlling unit 30 and a signal input from signal processing unit 26 into a digital signal.

Temperature controlling processor 272 generates a signal (temperature controlling state signal) indicating a temperature controlling state and outputs the signal to controller 11, based on a value that is output from temperature controlling unit 30 and converted into the digital value in AD conversion circuit 271.

The temperature controlling state signal is a signal indicating a level of a signal (signal level) of frequency (2f) twice a signal (frequency 1f) of the laser light that is emitted from laser diode LD and is subjected to the wavelength modulation. The signal having the frequency (frequency 2f) twice frequency 1f is converted into a digital value by AD conversion circuit 271 and, then, is extracted.

Figure 10:
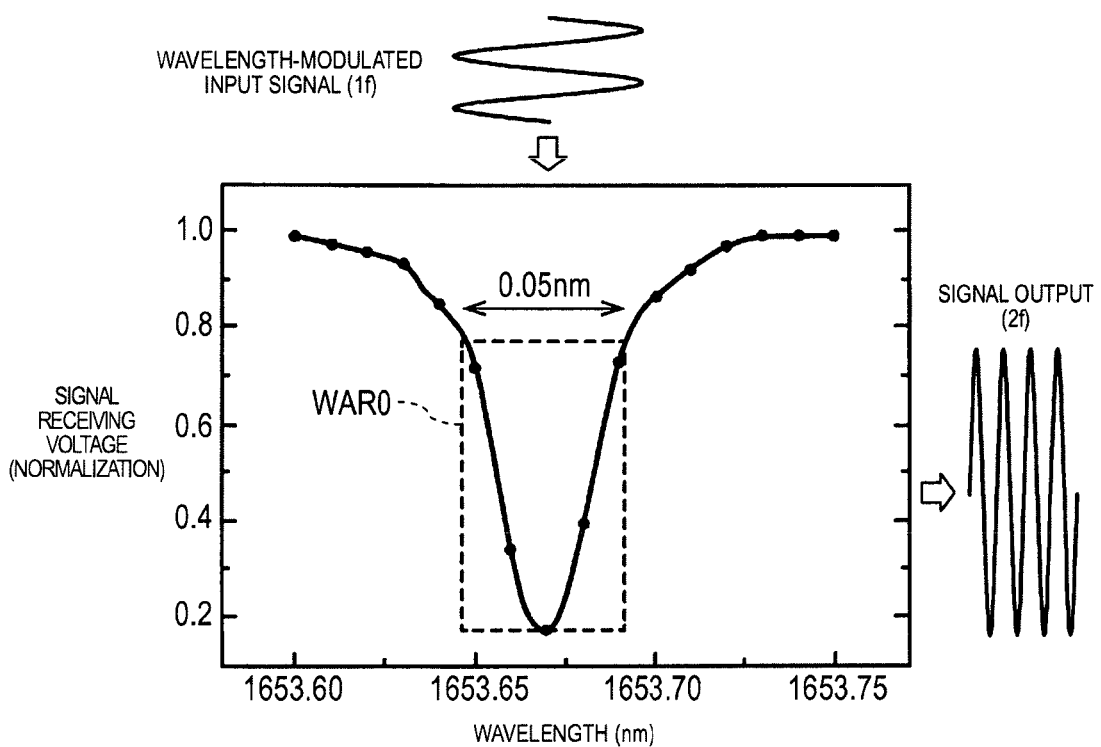
FIG. 10 is a schematic diagram illustrating an input signal and an output signal of laser light in a temperature controlling state in a case where an oscillation frequency of a laser diode is optimal with respect to absorption spectra of a specific substance.

The temperature of laser diode LD is not changed, and a modulation wavelength width of the laser light that is emitted from laser diode LD is not shifted from an absorption wavelength band of the specific substance (a modulation wavelength range WAR0 in FIG. 10). In this case, the temperature controlling state signal is a sine wave signal having a constant frequency, which is obtained based on the signal from photodiode PD2.

The temperature of laser diode LD is changed, and the modulation wavelength width of the laser light that is emitted from laser diode LD is shifted from the absorption wavelength band of the specific substance. In this case, the temperature controlling state signal is obtained based on the signal from photodiode PD2, and is decreased in level of the signal (signal level) of frequency (2f) twice frequency 1f.

Substance detection processor 273 detects the specific substance based on a value that is output from signal processing unit 26 in received light processor SA and is converted into a digital value in AD conversion circuit 271, and a signal indicating the detected specific substance is output to display processor 28.

Display processor 28, from invisible light sensor NVSS, generates substance position image data indicating a two-dimensional position of the specific substance in detection region SAR. The substance position image data includes image data indicating the specific substance and two-dimensional position information (for example, a pan angle and a tilt angle of camera platform 10) in detection region SAR. Display processor 28 outputs the substance position image data to display controller 37 of visible light camera VSC.

For example, in embodiments including the present embodiment, display processor 28 may transmit the substance position image data to monitor 150, or camera server CS, which will be described below, or a communication terminal, instead of transmitting the data to display controller 37 in visible light camera VSC.

As described above, information associated with the specific substance which is obtained by detection processor 27 is synthesized with the visible light image data in detection region SAR and the obtained data is displayed and output. Hence, invisible light sensor NVSS can visually and clearly show a user where the specific substance is present in detection region SAR.

As illustrated in FIG. 5, visible light camera VSC includes condenser V31, image sensor V33, signal processor V35, display controller 37, and output 38. Processor V20 executes a program stored in the memory, and thereby the functions of signal processor V35 and display controller 37 are realized.

Condenser V31 condenses incident light (reflected light RM) from outside in a range including detection region SAR, as a range of an angle of view, by invisible light sensor NVSS, and forms an image on a capturing surface of image sensor V33.

Image sensor V33 has the peak of spectral sensitivity with respect to a wavelength (for example, 0.4 μm to 0.7 μm) of visible light. Image sensor V33 converts an optical image formed on the capturing surface into an electric signal. Output from image sensor V33 is input as the electric signal into signal processor V35.

Signal processor V35 generates visible light image data defined by RGB (red, green, and blue), YUV (luminance/color difference), or the like by using the electric signal output from image sensor V33. In this manner, visible light image data captured by visible light camera VSC is generated. Signal processor V35 outputs the visible light image data to display controller 37.

For example, in a case where the specific substance is detected at a predetermined position from the visible light image data, display controller 37 synthesizes the visible light image data output from signal processor V35 with the substance position image data output from display processor 28 and generates display data. The display data is an example of information associated with the specific substance.

Output 38 outputs the display data to external devices (for example, camera server CS and monitor 150).

Camera server CS transmits, to a communication terminal or one or more externally connected devices, the display data output from display controller 37 and promotes display of the display data on a display screen of the communication terminal or one or more externally connected devices. Monitor 150 displays the display data output from display controller 37.

Next, an operation of detection camera 1 will be described.

Figure 7:
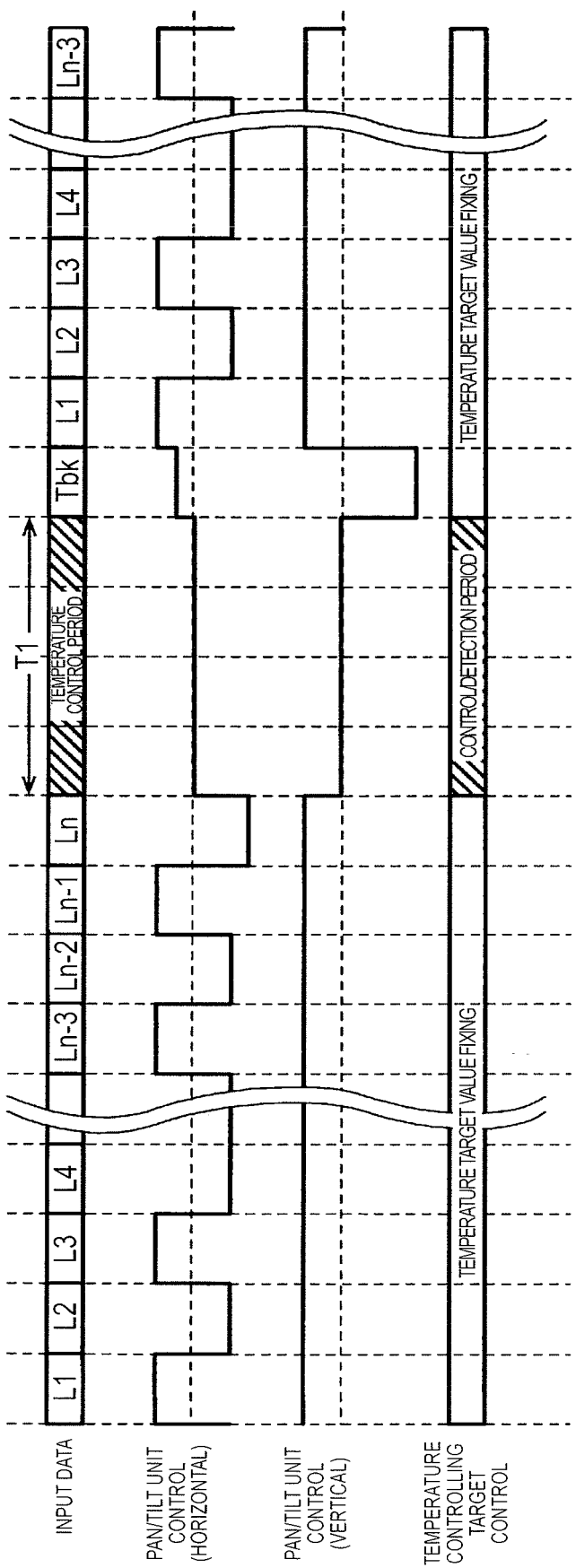
FIG. 7 is a timing chart illustrating an example of an operation of an invisible light sensor.
Figure 8:
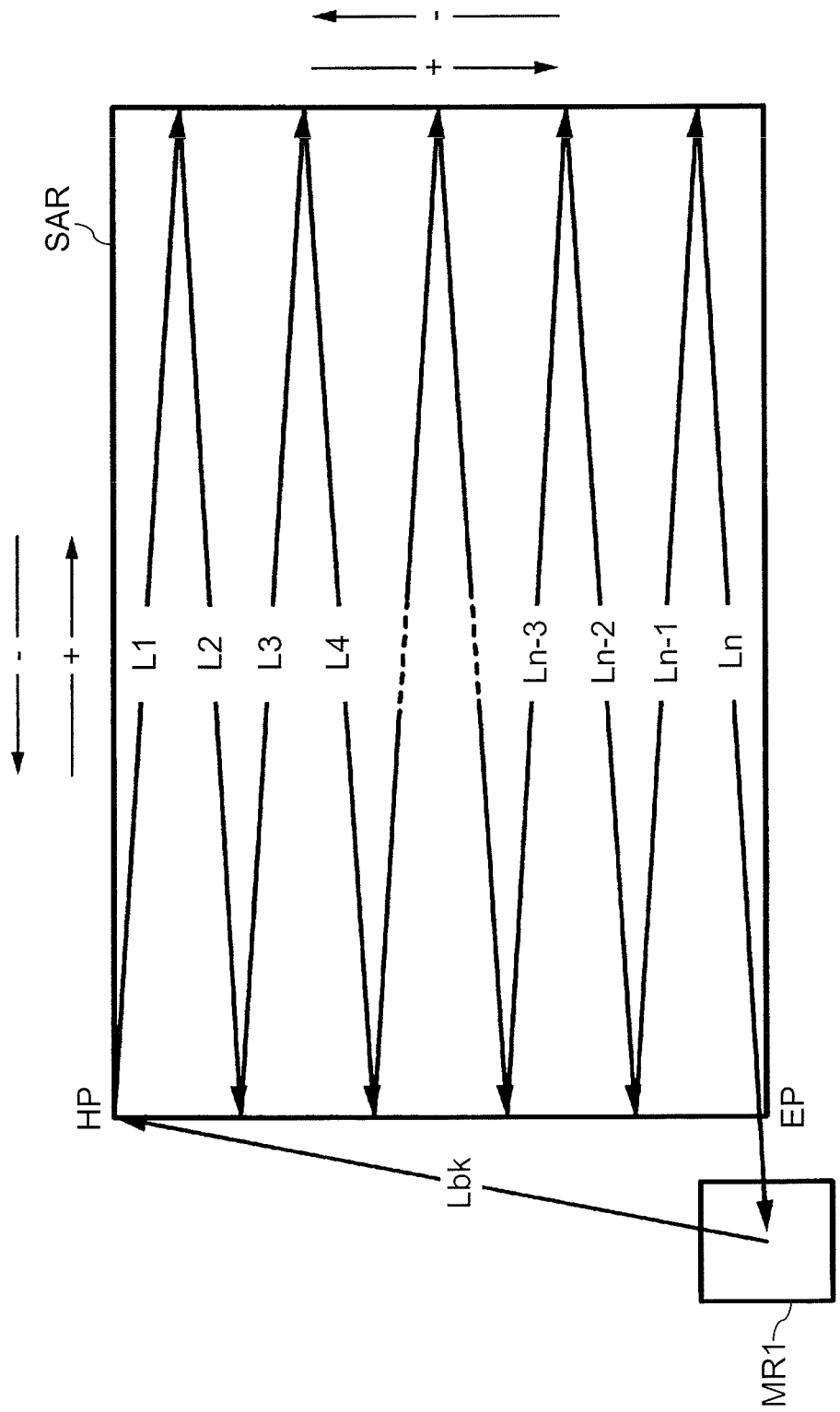
FIG. 8 is a schematic diagram illustrating an example of a scanning range of the invisible light sensor.

FIG. 7 is a timing chart illustrating an operation of invisible light sensor NVSS. FIG. 8 is a schematic diagram illustrating a scanning range of invisible light sensor NVSS. Pan/tilt unit 15 drives laser diode LD mounted on camera platform 10 in the pan direction and the tilt direction, thereby scanning detection region SAR (scanning range) by using laser light that is emitted from laser diode LD.

On first line (L1) in the horizontal (pan) direction, pan/tilt unit 15 changes the irradiation position of the laser light emitted from laser diode LD while adding an angle from initial position (HP) in the horizontal direction and the vertical direction to a plus (+).

When the irradiation position of the laser light reaches the end in the scanning range in the horizontal direction, pan/tilt unit 15 moves to second line (L2), add (+) an angle in the vertical direction while subtracting (−) an angle in the horizontal direction, and changes the irradiation position of the laser light emitted from laser diode LD.

Hereinafter, scanning with the laser light is performed to the Ln-th line in a similar manner. When the scanning of the Ln line is ended, scanning one time (one scan) in detection region SAR is ended. The irradiation position of the laser light moves beyond scan end position EP on a lower left corner in the scanning range (scan angle of view) and moves to reflective plate MR1.

In predetermined period T1 in which the irradiation position of the laser light stays on reflective plate MR1, wavelength detection/temperature controller 12 performs temperature control of regulating the temperature of laser diode LD such that the level of the signal (signal level) of frequency (2f) twice modulation frequency 1f is the maximum. In predetermined period T1, pan/tilt unit 15 stops driving (swivel operation) of camera platform 10 and fixes the position of laser diode LD. Predetermined period T1 includes a period for performing the temperature control. The temperature control is described in detail.

When predetermined period T1 elapses, pan/tilt unit 15 restarts to drive camera platform 10 in blank period Tbk, and the irradiation position of the laser light returns to initial position HP. Pan/tilt unit 15 changes the irradiation position of laser diode LD again while adding the angle from initial position (HP) in the horizontal direction and the vertical direction to a plus (+) on first line L1 in the horizontal direction, and the pan/tilt unit starts to perform scanning with the laser light.

Figure 9:
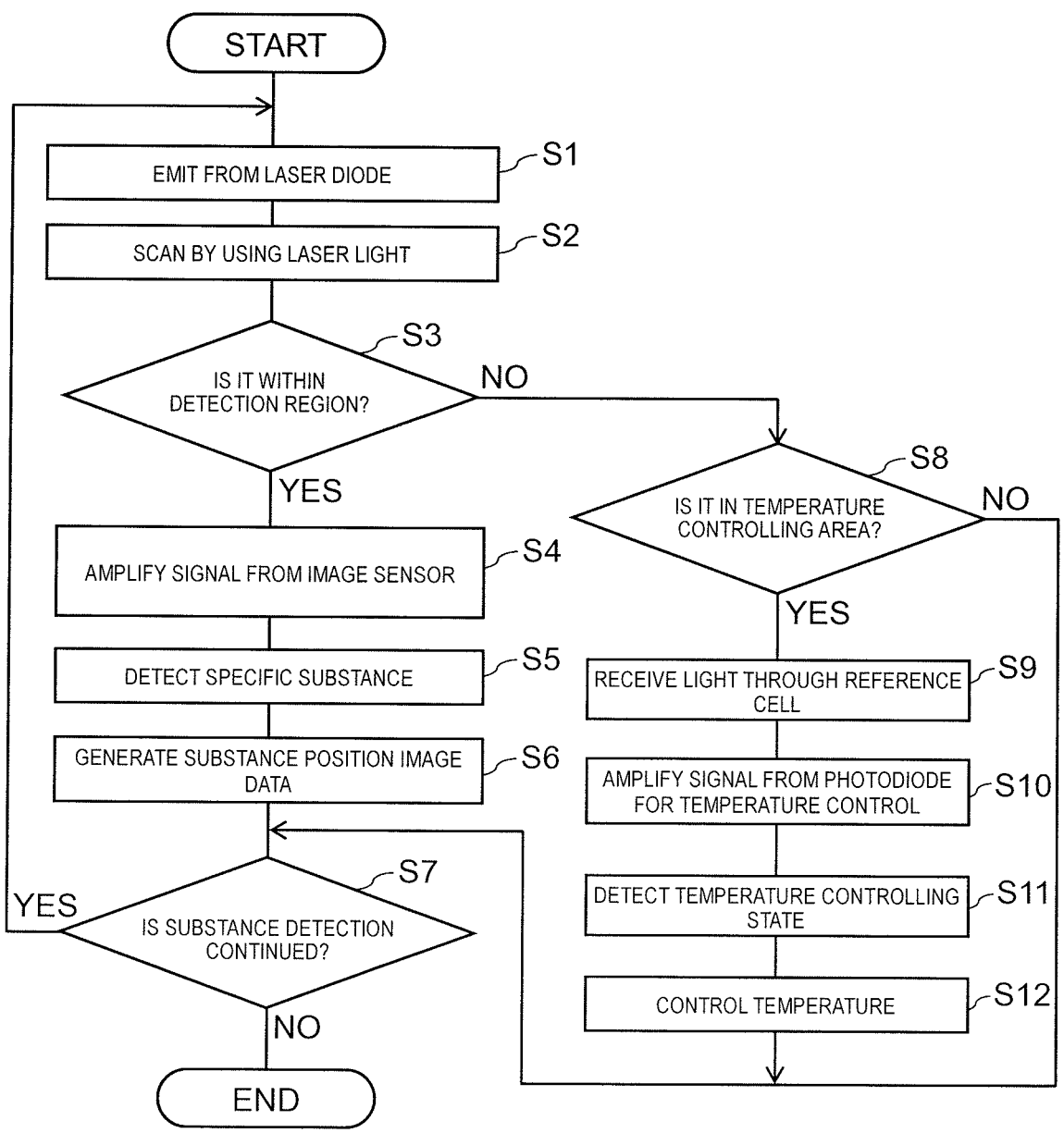
FIG. 9 is a flowchart illustrating an example of a signal processing procedure of the invisible light sensor.

FIG. 9 is a flowchart illustrating a signal processing procedure of invisible light sensor NVSS.

When laser diode LD receives a light source light-emitting signal from controller 11, laser diode LD emits the laser light (S1).

Pan/tilt unit 15 drives camera platform 10 and performs the scanning by using the laser light that is emitted from laser diode LD (S2).

Controller 11 determines whether or not the irradiation position of the laser light is present in detection region SAR (S3).

In a case where the irradiation position is present in detection region SAR, signal processing unit 26 amplifies an imaging signal input from photodiode PD (S4).

Detection processor 27 extracts the signal of frequency 2f from signals amplified by signal processing unit 26 and detects the presence or absence of the specific substance (here, methane gas (CH4)) (S5). For example, the presence or absence of gas GS is determined by whether or not the signal of frequency 2f (sine wave signal having a constant frequency) is equal to or higher than detection threshold M.

Display processor 28 generates the substance position image data, based on the image of the specific substance and the position information of the specific substance (S6). For example, the position information of the specific substance is obtained from a pan angle and a tilt angle of camera platform 10 that is driven by pan/tilt unit 15. Display processor 28 transmits the generated substance position image data to display controller 37 in visible light camera VSC. Display controller 37 superimposes the substance position image data acquired from display processor 28 on the image data captured by image sensor V33 in visible light camera VSC, generates display data, and outputs the generated data to camera server CS and monitor 150.

Controller 11 determines whether or not invisible light sensor NVSS continues to perform a substance detecting operation (S7). In a case where the substance detecting operation continues to be performed, controller 11 makes the procedure return to the process in S1. On the other hand, in a case where the substance detecting operation is stopped, controller 11 ends the operation.

On the other hand, in a case where the irradiation position of the laser light is present in detection region SAR in S3, controller 11 determines whether or not the irradiation position of the laser light is present in a temperature controlling area (region for controlling temperature), that is, on the inner side of reflective plate MR1 (S8). In a case where the irradiation position is present in the temperature controlling area, that is, in a case where the irradiation position of the laser light is present on a route from scan end position EP of detection region SAR to the temperature controlling area or on a route from the temperature controlling area to initial position HP, controller 11 makes the procedure proceed to the process in S7.

On the other hand, in a case where the irradiation position of the laser light is present in the temperature controlling area in S8, photodiode PD2 receives light that is reflected from reflective plate MR1 and is transmitted (passes) through reference cell CEL (S9). As described above, gas GS (for example, methane gas) which is the detection target substance is sealed in reference cell CEL.

I/V conversion circuit 31, an amplifier circuit 32, and a filter processing circuit 33 in temperature controlling unit 30 performs amplification processing on the signal from photodiode PD2 for temperature control (S10).

Detection processor 27 acquires the signal from temperature controlling unit 30, converts the signal into a digital value in AD conversion circuit 271, and detects the value as a value indicating the temperature controlling state (S11). Detection processor 27 generates the temperature controlling state signal including the detection results and transmits the signal to controller 11.

Controller 11 performs temperature control of regulating the temperature of laser diode LD such that the level of the signal (signal level) of frequency (2f) twice modulation frequency 1f is the maximum, based on the temperature controlling state signal (S12). Then, controller 11 makes the procedure proceed to the process in S7.

FIG. 10 is a schematic diagram illustrating an input signal and an output signal of the laser light in a case where the laser light emitted from laser diode LD has the optimal wavelength with respect to the absorption spectra of the specific substance. The input signal of the laser light is input to photodiodes PD and PD2. The output signal of the laser light is output to photodiodes PD and PD2.

Figure 11:
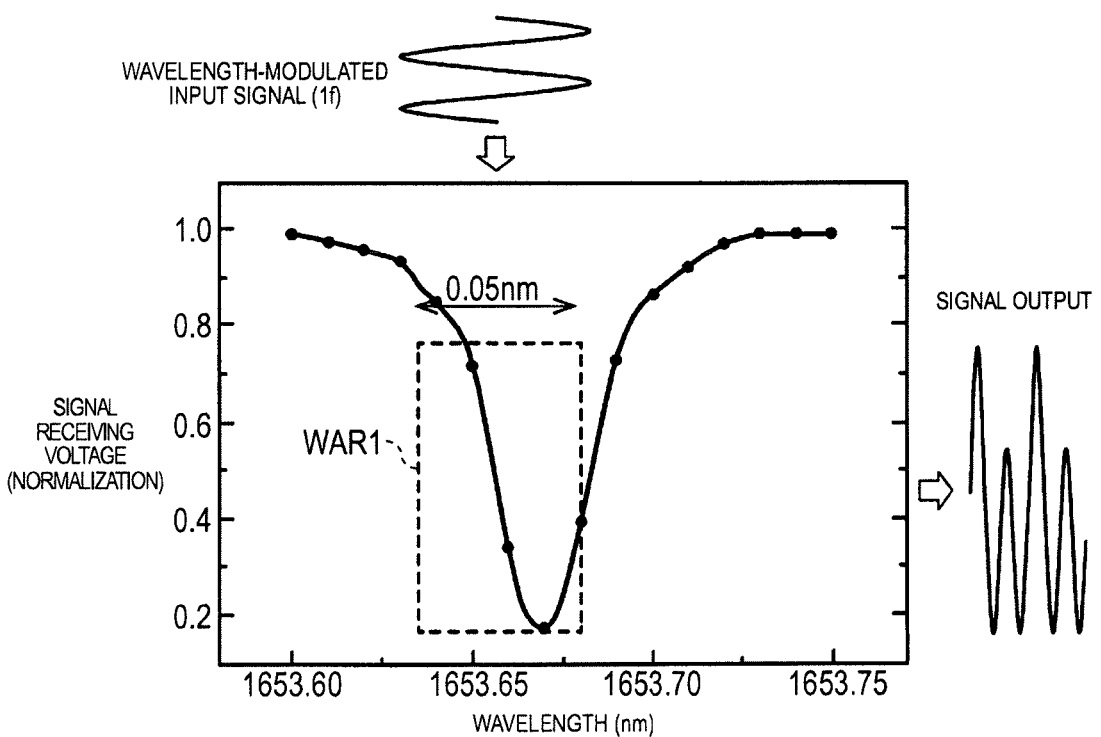
FIG. 11 is a schematic diagram illustrating the input signal and the output signal of the laser light in a temperature controlling state in a case where the laser light obtained by oscillation of the laser diode is shifted to the side of a short wavelength with respect to the absorption spectra of the specific substance.
Figure 12:
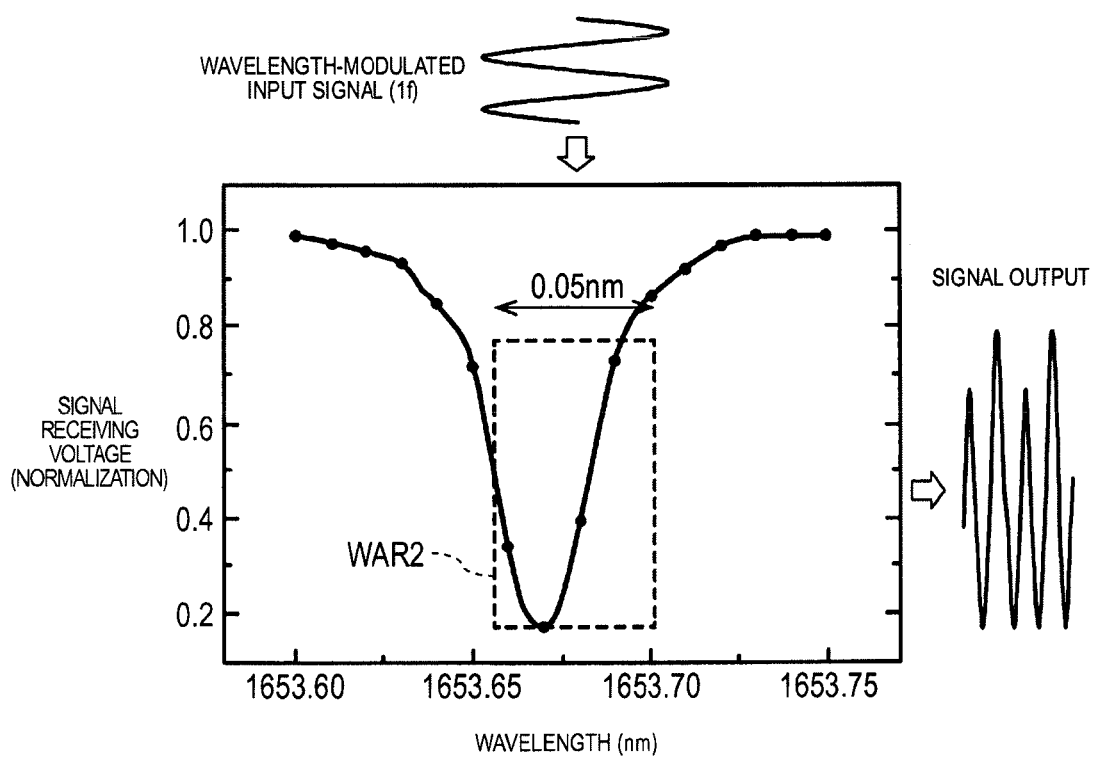
FIG. 12 is a schematic diagram illustrating the input signal and the output signal of the laser light in a temperature controlling state in a case where the oscillation frequency of the laser diode is shifted to a side of a long wavelength with respect to the absorption spectra of the specific substance.

FIGS. 10 to 12 illustrate methane gas (CH4) as an example of the gas which is the detection target substance. In FIGS. 10 to 12, the vertical axis represents voltage (unit is a normalized value) received by photodiodes PD and PD2, and the horizontal axis represents a wavelength (nm) of the laser light which is received by photodiodes PD and PD2. The lower the received voltage, the higher the absorption rate of the laser light by the specific substance. Absorption characteristics of a substance are determined depending on the substance.

In FIG. 10, the absorption spectra of the specific substance have a wavelength band having the center thereof at 1,653.67 nm. On the other hand, the laser light emitted from laser diode LD is modulated in a modulation width of 0.05 nm in which the center wavelength is at 1,653.67 nm as shown in wavelength modulating range WAR0.

As described above, the laser light emitted from laser diode LD and the laser light reflected from the specific substance in detection region SAR is detected as a signal having the frequency twice the signal of first laser light. In this case, the sine wave signal having the constant frequency is output.

FIG. 11 is a schematic diagram illustrating the input signal and the output signal of the laser light in a case where the wavelength of the laser light emitted from laser diode LD is shifted to the side of a short wavelength with respect to the absorption spectra of the specific substance.

In FIG. 11, for example, the laser light is subjected to the wavelength modulation in the modulation width of 0.05 nm in which the center wavelength is at 1,653.66 nm as shown in wavelength modulating range WAR1.

FIG. 12 is a schematic diagram illustrating the input signal and the output signal of the laser light in a case where the wavelength of the laser light emitted from laser diode LD is shifted to the side of a long wavelength with respect to the absorption spectra of the specific substance.

In FIG. 12, for example, the laser light is subjected to the wavelength modulation in the modulation width of 0.05 nm in which the center wavelength is at 1,653.68 nm as shown in wavelength modulating range WAR2.

As described above, in a case where the wavelength of the laser light emitted from laser diode LD is shifted to the side of the short wavelength or the side of the long wavelength, a signal having a change in frequency is output. The temperature control is performed such that the output signal becomes the sine wave signal having the constant frequency. Since the detection camera 1 is able to detect the sine wave signal having the constant frequency by using the laser light for substance detection by the temperature control, it is possible to improve accuracy of the substance detection.

Figure 13:
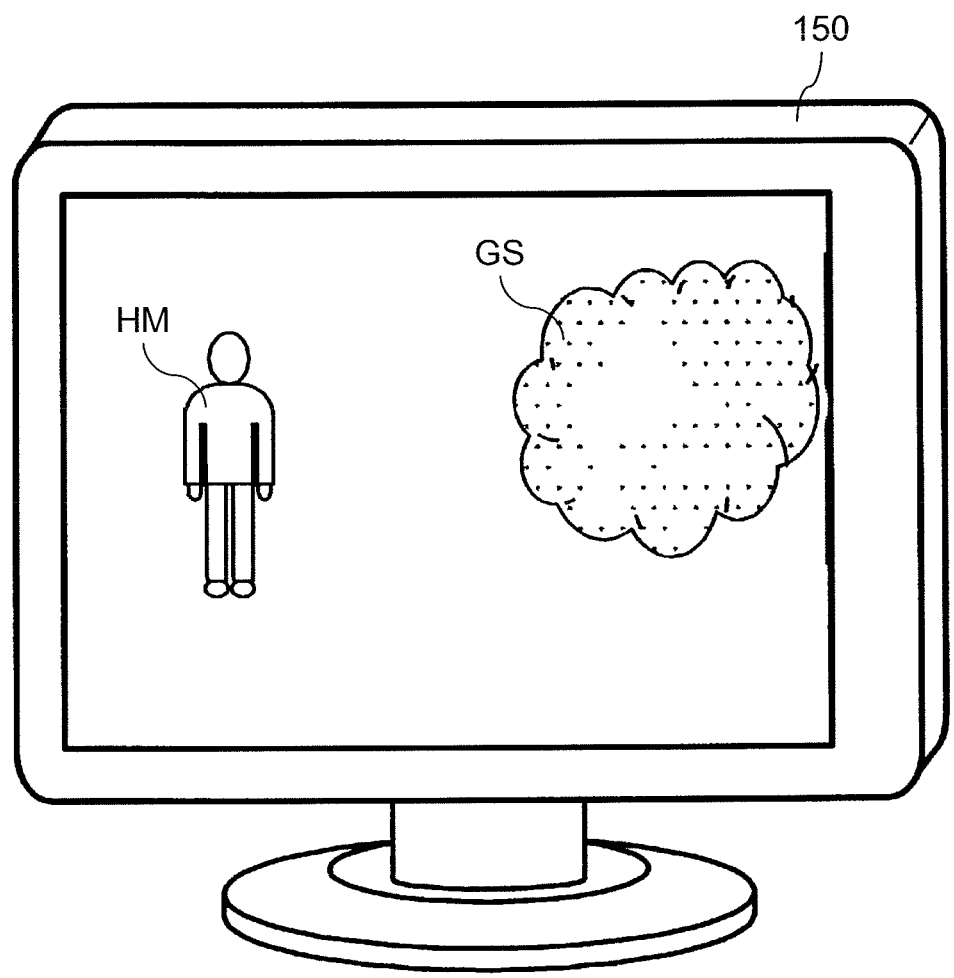
FIG. 13 is a schematic diagram illustrating an example of a display screen of a monitor.

FIG. 13 is a schematic diagram illustrating a display screen of monitor 150. Monitor 150 superimposes an image showing gas GS which is the specific substance detected by invisible light sensor NVSS on the image captured by visible light camera VSC and displays the superimposed image. In this manner, a user can visually recognize gas GS displayed on monitor 150.

As described above, in detection camera 1, laser diode LD emits the first laser light to the inside and the outside of detection region SAR of the substance. Photodiode PD receives second laser light which is reflected light of the first laser light from gas GS in detection region SAR. Detection processor 27 detects gas GS, based on the wavelength characteristics of the second laser light. Pan/tilt unit 15 changes an emitting direction of the first laser light and a receiving direction of the second laser light, inside and outside detection region SAR. Reference cell CEL, in which gas GS is sealed, is disposed outside detection region SAR. Photodiode PD2 for temperature control receives third laser light which is passing light of the first laser light through reference cell CEL. Wavelength detection/temperature controller 12 adjusts the temperature of the first laser light and controls the wavelength of the first laser light based on the wavelength characteristics of the third laser light.

Detection camera 1 is an example of the substance detecting device. Laser diode LD is an example of a transmitter. Photodiode PD is an example of a first receiver. Detection processor 27 is an example of a detector. Pan/tilt unit 15 is an example of an actuator. Photodiode PD2 for temperature control is an example of a second receiver. Wavelength detection/temperature controller 12 is an example of a wavelength controller. The first laser light is an example of first invisible light. The second laser light is an example of second invisible light. The third laser light is an example of third invisible light. Gas GS is an example of the detection target substance.

In this manner, detection camera 1 scans to detect gas GS which is the detection target substance in detection region SAR, and thus time and effort to manually change an orientation of detection camera 1 is saved. Hence, detection camera 1 is capable of easily detecting gas GS which is the detection target substance in detection region SAR. In addition, there is no need to provide a half mirror for causing the laser light to diverge in detection camera 1, and thus it is possible to reduce detection camera 1 in size.

In addition, laser diode LD and photodiode PD may be fixed to camera platform 10. Pan/tilt unit 15 changes the orientation of camera platform 10, and thereby laser diode LD may scan the inside and outside of detection region SAR by using the first laser light. Camera platform 10 is an example of a base.

In this manner, even when the orientation of camera platform 10 is changed, detection camera 1 can achieve the improvement in detection accuracy of the second laser light after first laser light emitted from laser diode LD is reflected from gas GS inside detection region SAR.

In addition, reflective plate MR1 disposed outside detection region SAR may reflect the first laser light. ND filter FIR may attenuate the third laser light after the first laser light is reflected from reflective plate MR1. Photodiode PD2 may receive the attenuated third laser light. Reflective plate MR1 is an example of a reflector. ND filter FIR is an example of a filter.

In this manner, the intensity of the third laser light received by photodiode PD2 is decreased, and thereby detection camera 1 can reduce degradation of accuracy of temperature control due to a significant intensity of the third laser light.

In addition, the driving of pan/tilt unit 15 may cause laser diode LD to emit the first laser light to the outside of detection region SAR after emitting the first laser light to every position inside detection region SAR.

In this manner, since detection camera 1 does not emit the first laser light to the outside of detection region SAR during the scanning, substance detection time is shortened, and thus it is possible to control the first laser light such that the first laser light has the constant center wavelength.

In addition, image sensor V33 may capture an image toward detection space K. A capturing range, within which image sensor V33 captures the image, may include detection region SAR of gas GS. The image toward detection space K is an example of a first image.

In this manner, detection camera 1 is capable of visually showing a position at which gas GS is detected and detecting the presence or absence of the substance within the capturing range.

In addition, processors 20 and V20 may visualize the position inside detection region SAR of detected gas GS and may generate a synthesized image obtained by superimposing (synthesizing) the visualized information on the image captured by image sensor V33. Output 38 may output the synthesized image. Output 38 is an example of an output device. The synthesized image is an example of a second image.

In this manner, as a video using augmented reality (AR) as an example, detection camera 1 is capable of displaying two-dimensional position information of the detected substance on the captured image, and thus it is possible to improve convenience for a user.

In addition, a substance detecting system may be configured to include detection camera 1 and monitor 150 that displays the synthesized image output from detection camera 1.

In this manner, the substance detecting system can be configured of detection camera 1 and monitor 150. According to the substance detecting system, the user can visually recognize the presence or absence of the specific substance from the synthesized image displayed on monitor 150.

Detection camera 1 may include a diffuser plate that is disposed outside detection region SAR and diffuses the first laser light, instead of reflective plate MR1. Photodiode PD2 may receive the diffused third laser light of the first laser light by the diffuser plate. The diffuser plate is an example of a diffuser.

In this manner, detection camera 1 does not need to attenuate the light and can control the temperature without ND filter FIR.

Second Embodiment

In the first embodiment, in the case where the temperature control of laser diode LD is performed, reflective plate MR1 is disposed in housing 1z, the laser light emitted from laser diode LD is reflected from reflective plate MR1, and then photodiode PD2 for temperature control receives the laser light. In the second embodiment, a case where, instead of reflective plate MR1, the diffuser plate is disposed and photodiode PD for substance detection receives light is described. In this manner, photodiode PD2 for temperature control is omitted.

Figure 14:
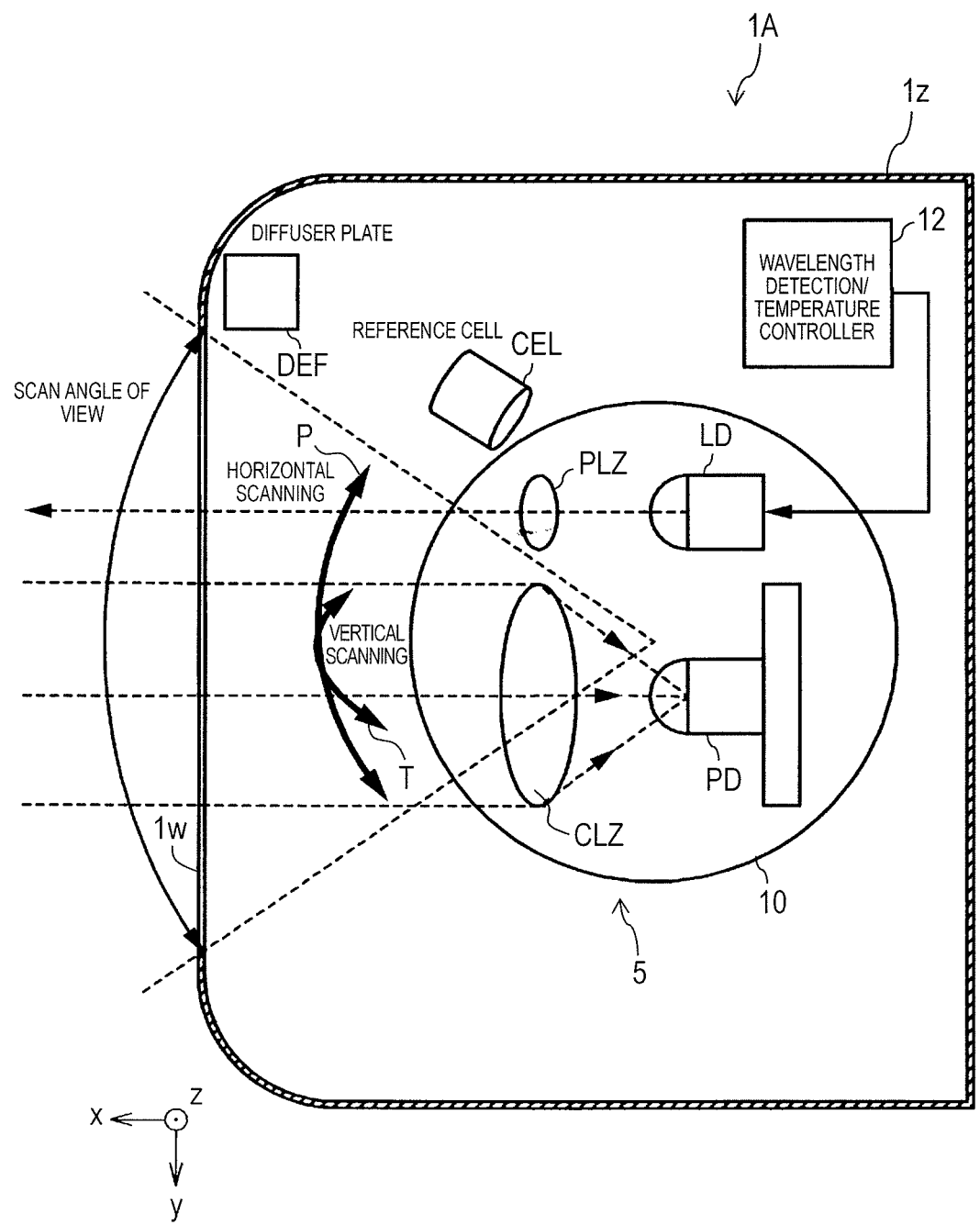
FIG. 14 is a schematic diagram illustrating an example of an internal configuration of a detection camera in a second embodiment.

FIG. 14 is a schematic diagram illustrating an internal configuration of detection camera 1A in the second embodiment. Since detection camera 1A of the second embodiment has substantially the same configuration as that of detection camera 1 of the first embodiment, the same reference marks are assigned to the same constituent elements as those of the first embodiment, and thus the description thereof is omitted.

As described above, diffuser plate DEF is disposed outside detection region SAR close to opening 1w of housing 1z. In addition, condenser CLZ2 and photodiode PD2 for temperature control are omitted. In addition, reference cell CEL is disposed between diffuser plate DEF and laser diode LD.

Figure 15:
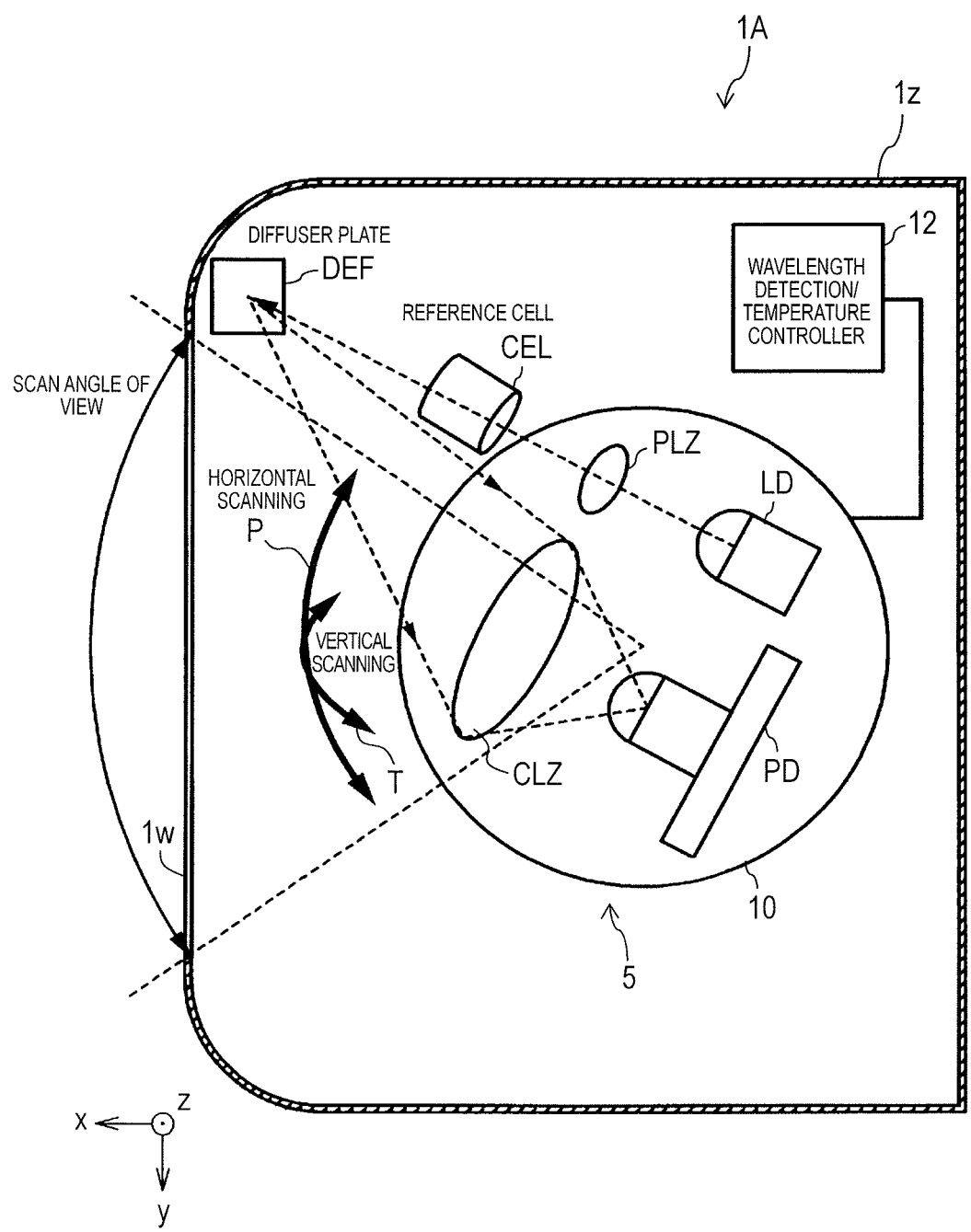
FIG. 15 is a schematic diagram illustrating an example of an internal operation of the detection camera during temperature control.

FIG. 15 is a schematic diagram illustrating an internal operation of detection camera 1A during the temperature control.

In the temperature control, the laser light emitted from laser diode LD is transmitted through reference cell CEL and is diffused by diffuser plate DEF. A part of the diffused laser light is received by photodiode PD for substance detection through condenser CLZ. Hence, there is no need to provide photodiode PD2 for temperature control and condenser CLZ2.

In addition, since diffuser plate DEF diffuses the laser light, the intensity of the laser light received by photodiode PD is more reduced than the intensity of the laser light reflected from reflective plate. In this manner, there is no need to provide the ND filter that attenuates the intensity of the laser light.

In addition, since diffuser plate DEF is disposed at the same position as that of reflective plate MR1 of the first embodiment, a timing to perform the temperature control may be the same as that of the first embodiment. In addition, the operation of detecting the specific substance is the same as that of the first embodiment.

Figure 16:
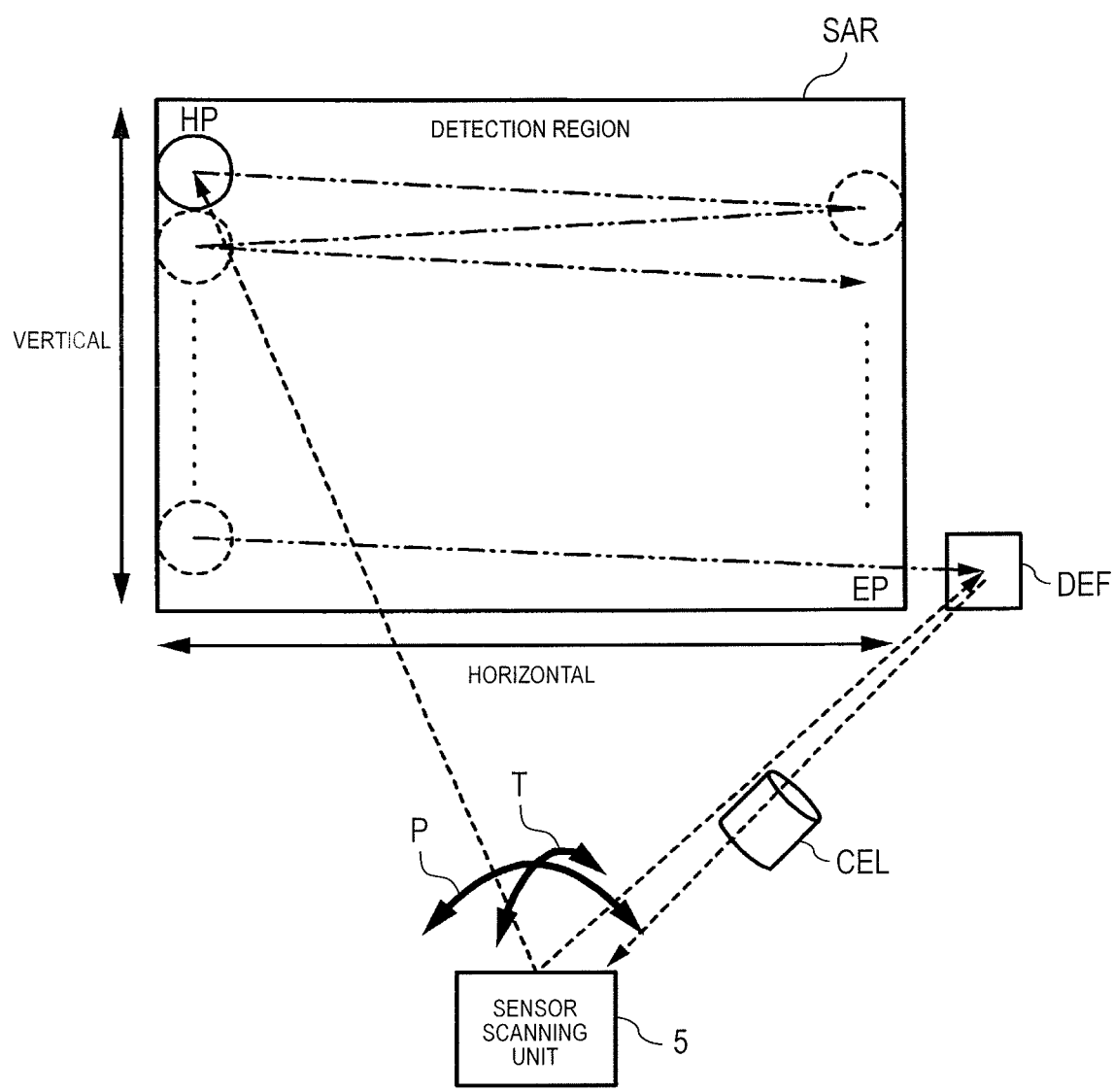
FIG. 16 is a schematic diagram illustrating an example of scanning a region including a detection region by a sensor scanning unit.

FIG. 16 is a schematic diagram illustrating the scanning of a region including detection region SAR by sensor scanning unit 5.

The swivel of camera platform 10 enables sensor scanning unit 5 to scan a space within the scan angle of view (detection region SAR) in the pan direction and the tilt direction by using laser light LS emitted from laser diode LD mounted on camera platform 10. Diffuser plate DEF is disposed at a position beyond scan end position EP in the horizontal direction, at which one scan with the laser light is ended and the laser light has yet to return to initial position HP.

In the temperature control, the laser light emitted from laser diode LD is diffused by diffuser plate DEF, is transmitted through reference cell CEL, in which gas that is the detection target substance is sealed, is condensed by condenser CLZ for substance detection, and is received by photodiode PD for substance detection.

Figure 17:
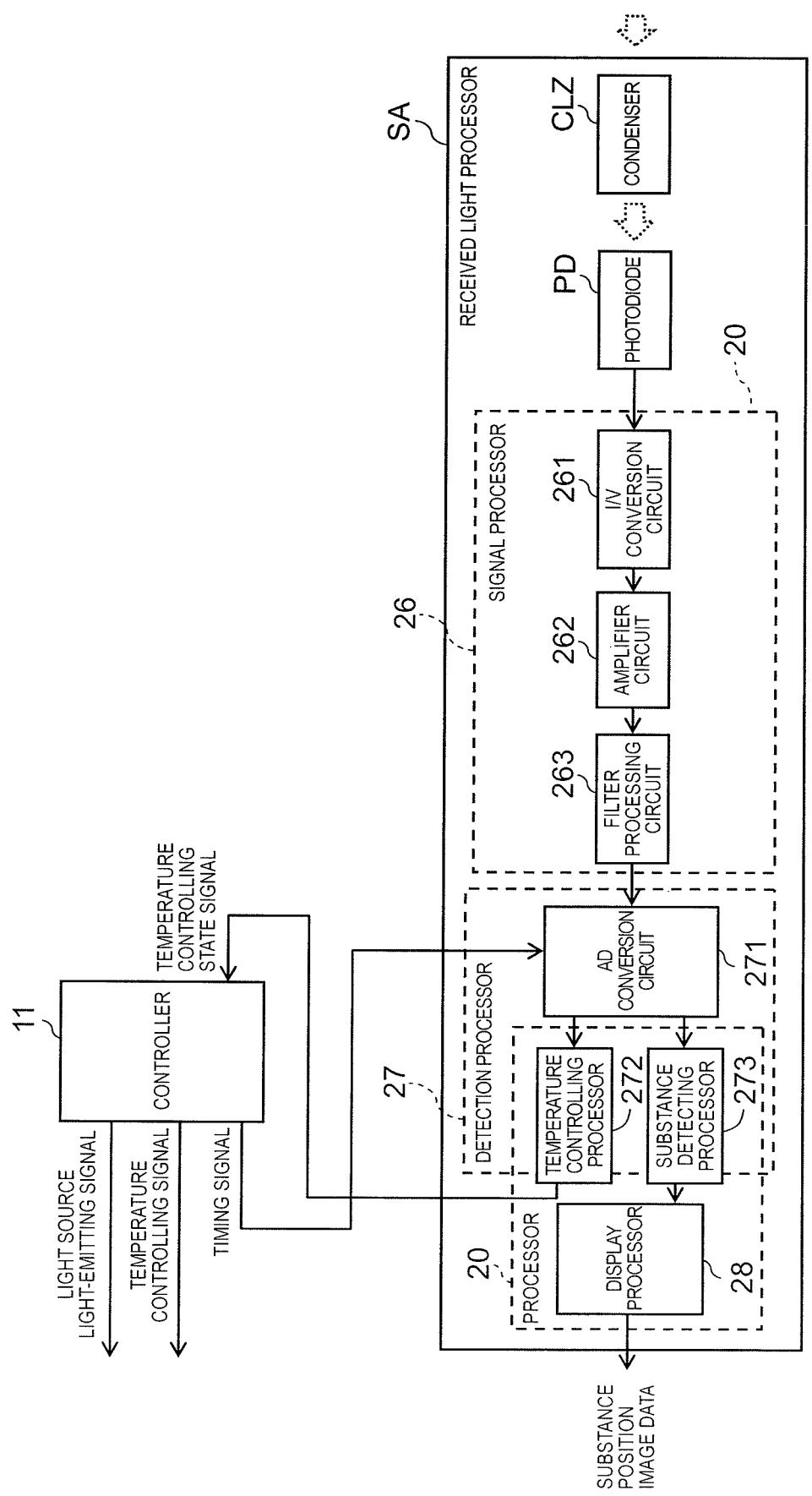
FIG. 17 is a block diagram illustrating an example of a configuration of the detection camera.

FIG. 17 is a block diagram illustrating a configuration of detection camera 1A.

Detection camera 1A has the same configuration as that of the first embodiment, but has a configuration in which temperature controlling unit 30 is omitted, unlike to the first embodiment. In other words, in the temperature control, photodiode PD receives the laser light that is diffused by diffuser plate DEF and is condensed by condenser CLZ. The operations after the light reception are the same as those of the first embodiment.

In the second embodiment, diffuser plate DEF disposed outside detection region SAR diffuses the first laser light emitted from laser diode LD. Photodiode PD receives the laser light obtained after the laser light from laser diode LD is diffused by diffuser plate DEF. Hence, even when the first laser light has high intensity, the third laser light is diffused by diffuser plate DEF. Therefore, photodiode PD is capable of receiving the third laser light without causing the third light to pass through the ND filter.

As described above, in detection camera 1A of the present embodiment, photodiode PD may operate as photodiode PD2 of the first embodiment and receive the third laser light.

In this manner, in detection camera 1A, it is possible to omit photodiode PD2 for temperature control, and thus it is possible to reduce the housing of detection camera 1A in size, to reduce the number of components, and to reduce costs.

Detection camera 1A may include ND filter FIR and reflective plate MR1 reflecting the first laser light, which are disposed outside detection region SAR, instead of diffuser plate DEF.

Third Embodiment

In the first and second embodiments, the photodiode for temperature control is an example of a device that receives the laser light that is emitted from laser diode LD and is reflected from the reflective plate or the diffuser plate. In the third embodiment, a case where the photodiode for temperature control directly receives the laser light via ND filter FIR is described.

Figure 18:
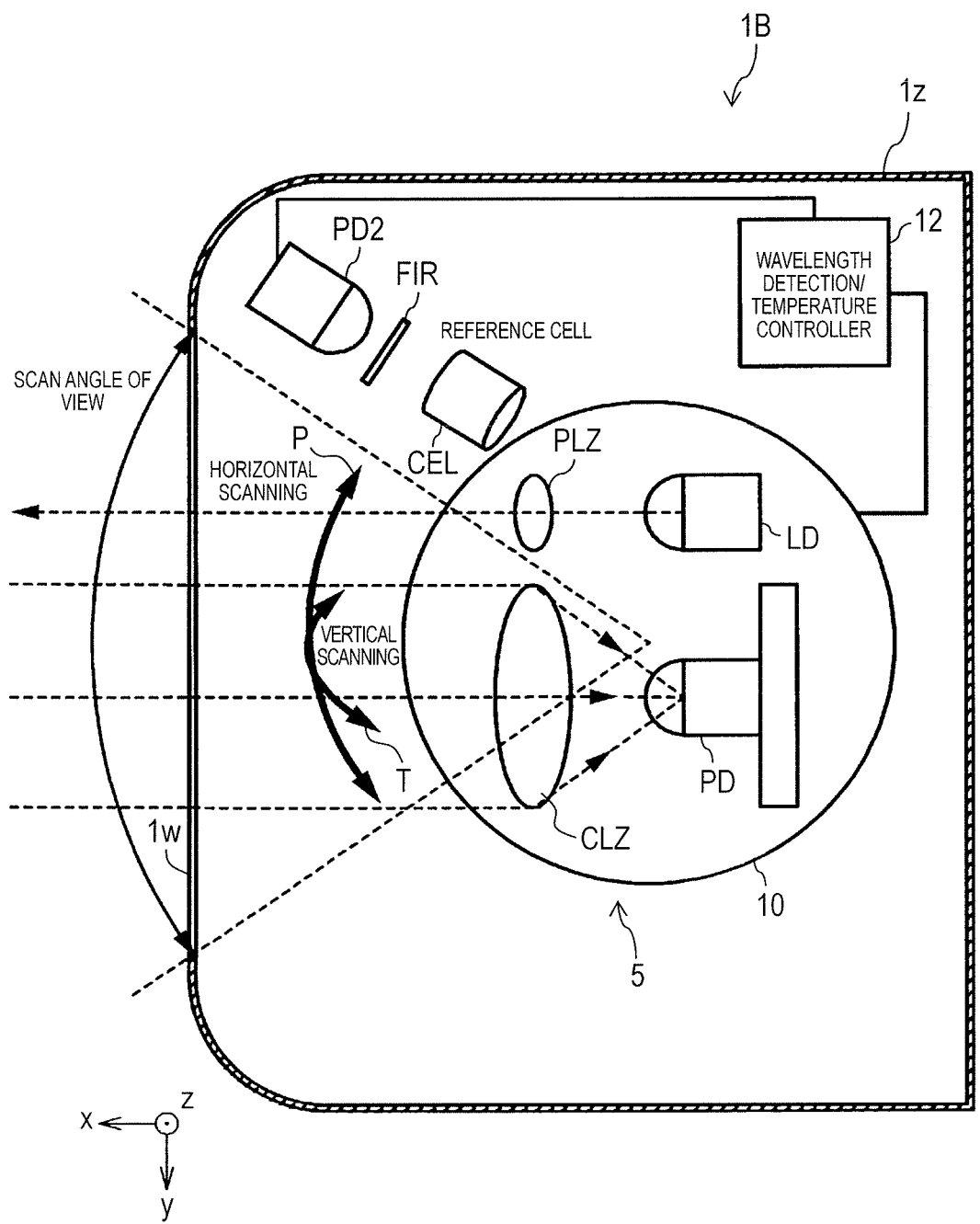
FIG. 18 is a schematic diagram illustrating an example of an internal configuration of a detection camera in a third embodiment.

FIG. 18 is a schematic diagram illustrating an internal configuration of detection camera 1B in the third embodiment. Since detection camera 1B of the third embodiment has substantially the same configuration as the configurations of detection cameras 1 and 1A of the first and second embodiments, the same reference marks are assigned to the same constituent elements as those of the first and second embodiments, and thus the description thereof is omitted.

As described above, photodiode PD2 for temperature control is disposed at a position outside detection region SAR close to opening 1w of housing 1z. Here, condenser CLZ2 is omitted. In addition, ND filter FIR is disposed between reference cell CEL and photodiode PD2 for temperature control.

Figure 19:
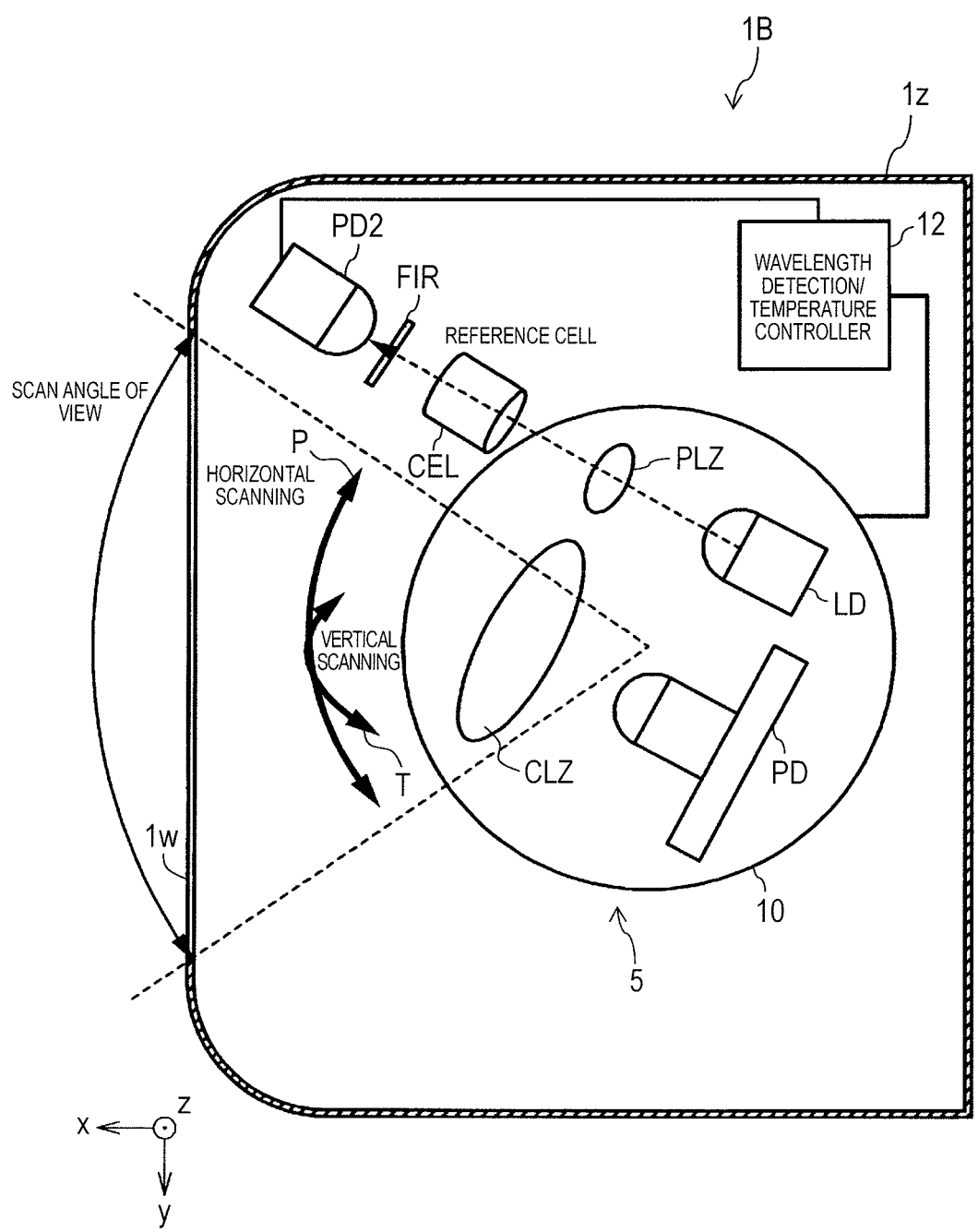
FIG. 19 is a schematic diagram illustrating an example of an internal operation of the detection camera during temperature control.

FIG. 19 is a schematic diagram illustrating an internal operation of detection camera 1B during the temperature control.

In the temperature control, the laser light emitted from laser diode LD is transmitted through reference cell CEL, passes through ND filter FIR, and is directly received by photodiode PD2 for temperature control. In a case of direct reception, the intensity of the laser light emitted from laser diode LD is high. Therefore, ND filter FIR is disposed and the intensity of the laser light is attenuated.

In addition, since photodiode PD2 for temperature control is disposed at the same position as the position of diffuser plate DEF or reflective plate MR1, a timing to perform the temperature control may be the same as that of the first or second embodiment. In addition, the operation of detecting the specific substance is the same as that of the first embodiment.

Figure 20:
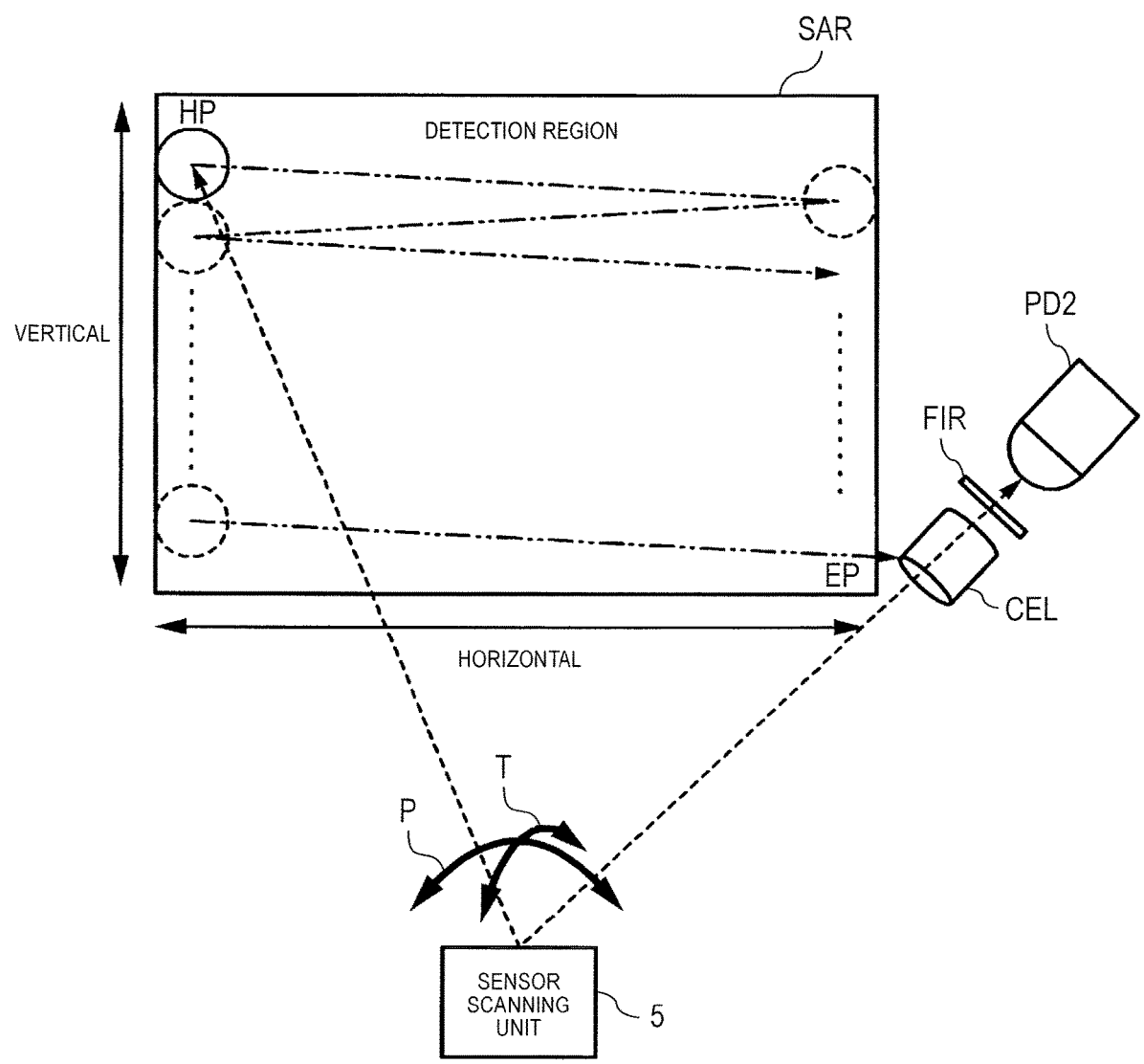
FIG. 20 is a schematic diagram illustrating an example of scanning a region including a detection region by a sensor scanning unit.

FIG. 20 is a schematic diagram illustrating the scanning of a region including detection region SAR by sensor scanning unit 5.

The swivel of camera platform 10 enables sensor scanning unit 5 to scan a space within the scan angle of view (detection region SAR) in the pan direction and the tilt direction by using laser light LS emitted from laser diode LD mounted on camera platform 10. Photodiode PD2 for temperature control is disposed at a position beyond scan end position EP in the horizontal direction, at which one scan with the laser light is ended and the laser light has yet to return to initial position HP.

In the temperature control, the laser light emitted from laser diode LD is transmitted through reference cell CEL in which the gas that is the detection target substance is sealed, is attenuated by through ND filter FIR, and is received by photodiode PD2 for temperature control.

In the third embodiment, reflective plate MR1 or diffuser plate DEF is not present inside housing 1z, and photodiode PD2 for temperature control may be disposed at the position thereof. In this manner, it is possible to dispose components densely in detection camera 1, and thus it is possible to reduce detection camera 1 in size.

Modification Examples of First to Third Embodiments

As described above, the first to third embodiments are described as examples of the technology according to this disclosure. However, the technology according to this disclosure is not limited thereto, and may be applied to an embodiment in which modification, replacement, addition, omission, or the like is performed.

In the first to third embodiments, an example in which invisible light sensor NVSS receives the laser light transmitted through reference cell CEL at a timing when the laser light reaches the temperature controlling area is described. In other words, after one scan of detection region SAR is performed, temperature control is performed one time; however, the temperature control may be also performed during the scanning.

Figure 21:
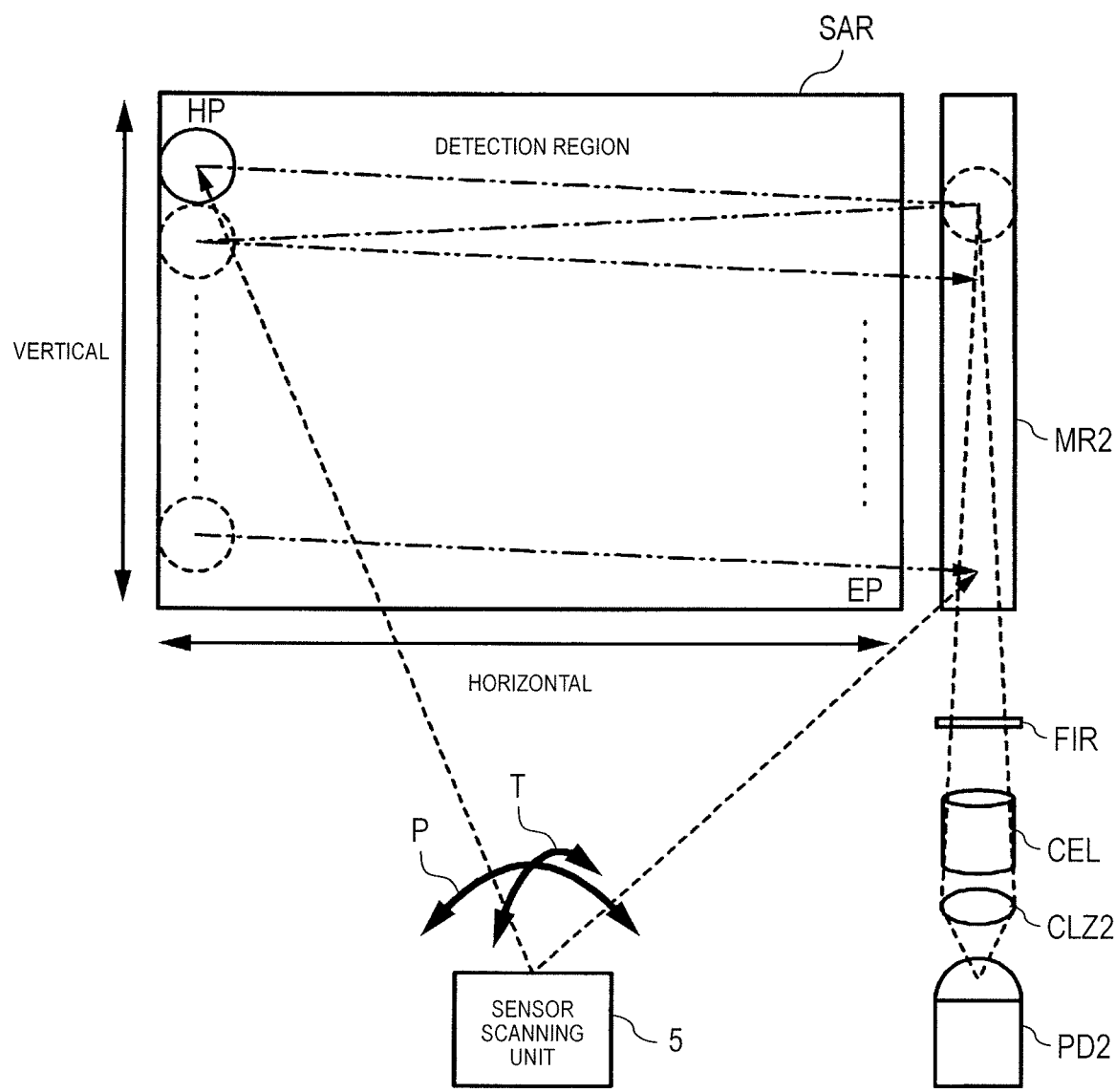
FIG. 21 is a schematic diagram illustrating an example of scanning performed on a region including a detection region by a sensor scanning unit in another embodiment.

FIG. 21 is a schematic diagram illustrating the scanning of a region including detection region SAR by a sensor scanning unit in another embodiment. In FIG. 21, the length of reflective plate MR2 is longer in the vertical direction of detection region SAR, compared to reflective plate MR1 described above. In other words, a configuration in which the laser light can be reflected in the temperature control for each line is employed.

Reflective plate MR2 is disposed at a position beyond the position at which scanning of every one line of detection region SAR with the laser light emitted from laser diode LD is ended. Sensor scanning unit 5 causes reflective plate MR2 to reflect the laser light emitted from laser diode LD after scanning of one line is ended such that the laser light travels toward photodiode PD2 for temperature control.

In other words, in the other embodiments, the driving of pan/tilt unit 15 causes laser diode LD to emit the first laser light to positions adjacent to each other in a predetermined direction (horizontal direction in FIG. 21) in detection region SAR and, then to emit the first laser light to the outside of detection region SAR (here, reflective plate MR2).

In this manner, detection camera 1 can also perform the temperature control during one scan, the number of adjustment of the temperature of laser diode LD is increased, and the number of control of the wavelength of the first laser light is increased. As described above, in detection camera 1, the first laser light is more frequently adjusted to have the constant center wavelength, and thereby it is possible to improve the detection accuracy of the substance.

In the first to third embodiments, the infrared light is used as the invisible light; however, ultraviolet light may be used depending on the absorption spectra of the detection target substance.

In this manner, detection camera 1 can increase a range in which a substance can be detected.

In the first to third embodiments, a processor or a controller may be configured to be physically present. In addition, when a programmable processor or controller is used, it is possible to change process content by changing a program, and thus it is possible to increase flexibility of design of the processor or the controller. The processor or the controller may be configured of one semiconductor chip or may be physically configured of a plurality of semiconductor chips. In a case where the processor or the controller is configured of the plurality of semiconductor chips, various types of control of the first to third embodiments may be realized by respectively different semiconductor chips. In this case, it is possible to consider that one processor or controller is configured of the plurality of semiconductor chips. In addition, the processor or controller may be configured of the semiconductor chip and members (condenser or the like) having other functions. In addition, one semiconductor chip may be configured to realize the function of the processor or the controller and functions other than the functions thereof.

Fourth Embodiment

When an LD module of gas detecting device emits laser light subjected to wavelength modulation having an arbitrary wavelength at the center, a photodiode receives the laser light reflected from the detection region, and the reflectance is uniform except for the detection target object in the detection region, a frequency twice the frequency of wavelength modulation by the LD module becomes an output signal of the photodiode in a case where the detection target substance is detected, and a frequency twice the frequency of wavelength modulation does not become an output signal of the photodiode in a case where the detection target substance is not detected. A state of uniform reflectance means a state in which the background in the detection region is in one color.

On the other hand, in a state in which the reflectance is not uniform except for the detection target object in the detection region, an output signal is changed in response to an input signal of the photodiode even when the detection target object is not present. For example, in a case where the background is in a two-color stripe state, a frequency of the reflectance of the background approximates twice a frequency of an input signal, an output signal having a frequency twice an input signal is generated even when no detection target object is present, and there is a possibility of false detection when the detection target is present. In this case, the detection accuracy of the substance is low.

Hereinafter, a substance detecting device and a substance detecting method in which it is possible to improve the detection accuracy of the substance in the detection region will be described.

[Configuration and the Like]

A schematic diagram illustrating an outline of detection camera 1 including invisible light sensor NVSS in a fourth embodiment is the same as FIG. 1 in the first to third embodiments, and thus the detailed description is omitted. Detection camera 1 is configured to include visible light camera VSC and invisible light sensor NVSS.

Figure 22:
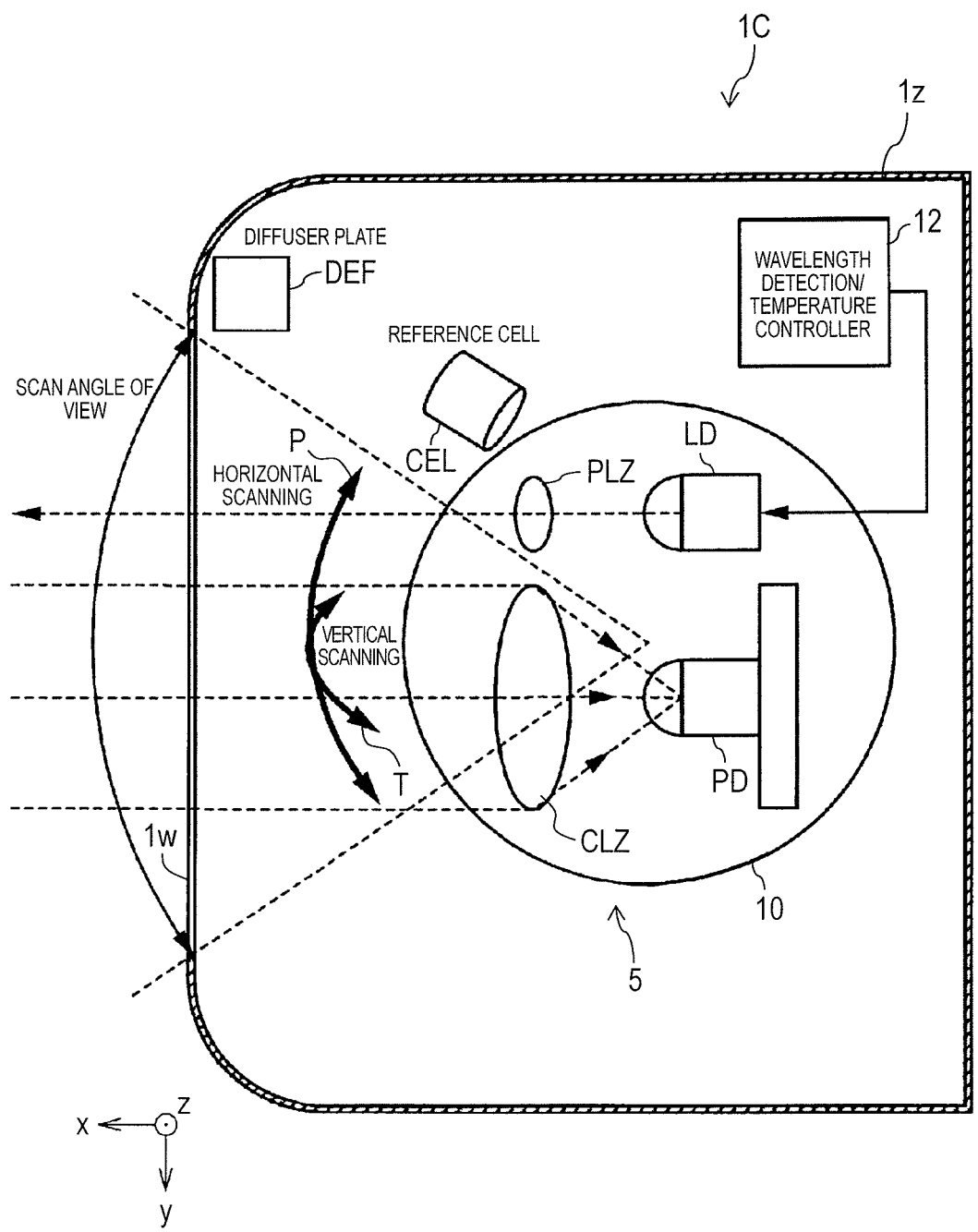
FIG. 22 is a schematic diagram illustrating an example of an internal configuration of a detection camera in a fourth embodiment.

FIG. 22 is a schematic diagram illustrating an internal configuration of detection camera 1 in the fourth embodiment. FIG. 22 illustrates the internal configuration of detection camera 1 when viewed from above in FIG. 1 (downward in the z-axis direction).

For example, detection camera 1 includes box-shaped housing 1z. Opening 1w for invisible light sensor NVSS is formed in a side surface of housing 1z. Transparent glass or resin may be fit in opening 1w for water proof/dust proof. In addition, capturing lens V31 of visible light camera VSC is exposed from the side surface of housing 1z.

Sensor scanning unit 5 is provided inside housing 1z. Sensor scanning unit 5 includes camera platform 10 and pan/tilt unit 15. Camera platform 10 freely swivels in the pan direction (direction parallel to the xy plane in the figure) represented by the arrow P in FIG. 22 and in the tilt direction (z-axis direction in the figure) represented by the arrow T in the figure. Pan/tilt unit 15 includes a motor mechanism that drives camera platform 10.

On camera platform 10, laser diode LD, collimator lens PLZ, photodiode PD, and condenser CLZ are mounted. Pan/tilt unit 15 causes camera platform 10 to swivel in the pan direction and the tilt direction, thereby making it possible to perform two-dimensional scanning (horizontal scanning and vertical scanning) in detection region SAR by using laser light LS that is emitted from laser diode LD.

Laser light LS emitted from laser diode LD is transmitted through collimator lens PLZ so as to be parallel light and is emitted toward detection space K. The laser light RV reflected from gas GS in detection space K is incident through opening 1w formed in housing 1z of detection camera 1, is condensed by condenser CLZ, and is received by photodiode PD.

The presence or absence of gas GS, as the detection target substance, which is present in detection space K is determined from absorption spectra (absorption characteristic) of the laser light RV received by photodiode PD. Detection region SAR is set depending on the shape of opening 1w formed in housing 1z. Detection region SAR corresponds to a range (scan angle of view) in which it is possible to perform scanning in detection space K with laser light LS emitted from laser diode LD.

Here, laser diode LD is likely to be influenced by a temperature, and a wavelength of laser light LS which is emitted from laser diode LD is shifted due to a slight change in temperature. Therefore, invisible light sensor NVSS performs temperature control (control for regulating a temperature) such that the wavelength (center wavelength in wavelength modulation) of laser light LS is not changed during an operation of gas detection and the temperature of laser light LS that is emitted from laser diode LD is maintained to be constant.

In order to perform the temperature control of laser light LS that is emitted from laser diode LD, diffuser plate DEF is disposed outside detection region SAR close to opening 1w of housing 1z. In addition, reference cell CEL is disposed between diffuser plate DEF and laser diode LD. Gas having the same components as those of the specific substance (here, methane gas) is sealed in reference cell CEL.

In the temperature control, laser light LS emitted from laser diode LD is transmitted through reference cell CEL, is diffused by diffuser plate DEF, and then is received by photodiode PD for substance detection with a part of diffused light passing through condenser CLZ. In addition, since diffuser plate DEF diffuses laser light LS, the intensity of laser light RV received by photodiode PD is reduced, and the intensity satisfies a range of an allowable light receiving amount of photodiode PD.

Figure 23:
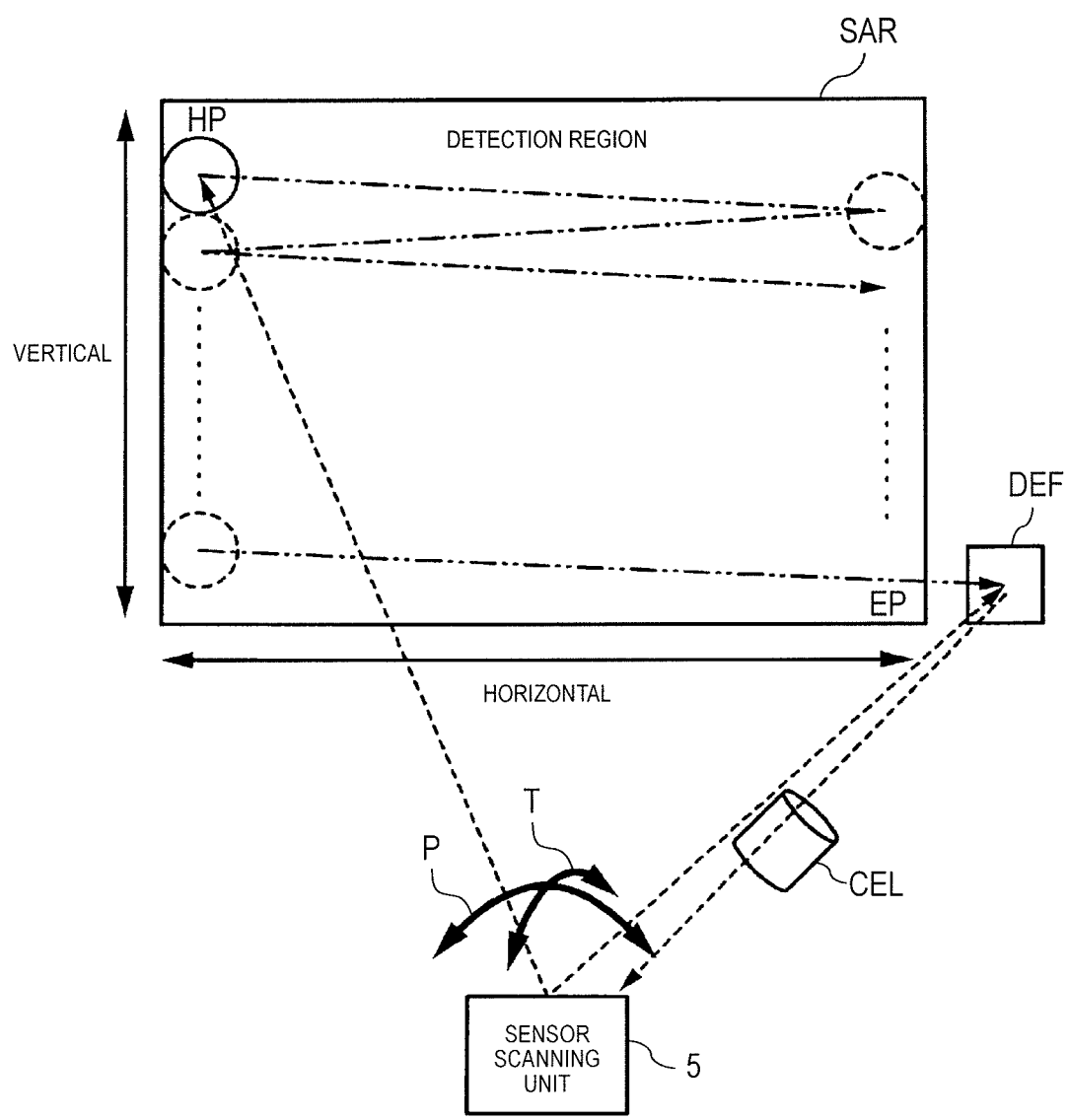
FIG. 23 is a schematic diagram illustrating an example of scanning a detection region by a sensor scanning unit in the fourth embodiment.

FIG. 23 is a schematic diagram illustrating an example of the scanning of a region including detection region SAR by sensor scanning unit 5 in the fourth embodiment. The swivel of camera platform 10 of sensor scanning unit 5 enables the scanning to be performed on a space within the scan angle of view (detection region SAR) in the pan direction (horizontal direction) and the tilt direction (vertical direction) by using laser light LS emitted from laser diode LD mounted on camera platform 10. In addition, in FIG. 23, diffuser plate DEF is disposed at a position beyond scan end position EP in the horizontal direction, at which one scan with laser light LS is ended and laser light LS has yet to return to initial position HP.

In the temperature control, laser light LS emitted from laser diode LD is diffused by diffuser plate DEF, is transmitted through reference cell CEL, in which gas that is the detection target substance is sealed, is condensed by condenser CLZ for substance detection, and is received by photodiode PD for substance detection.

Figure 24:
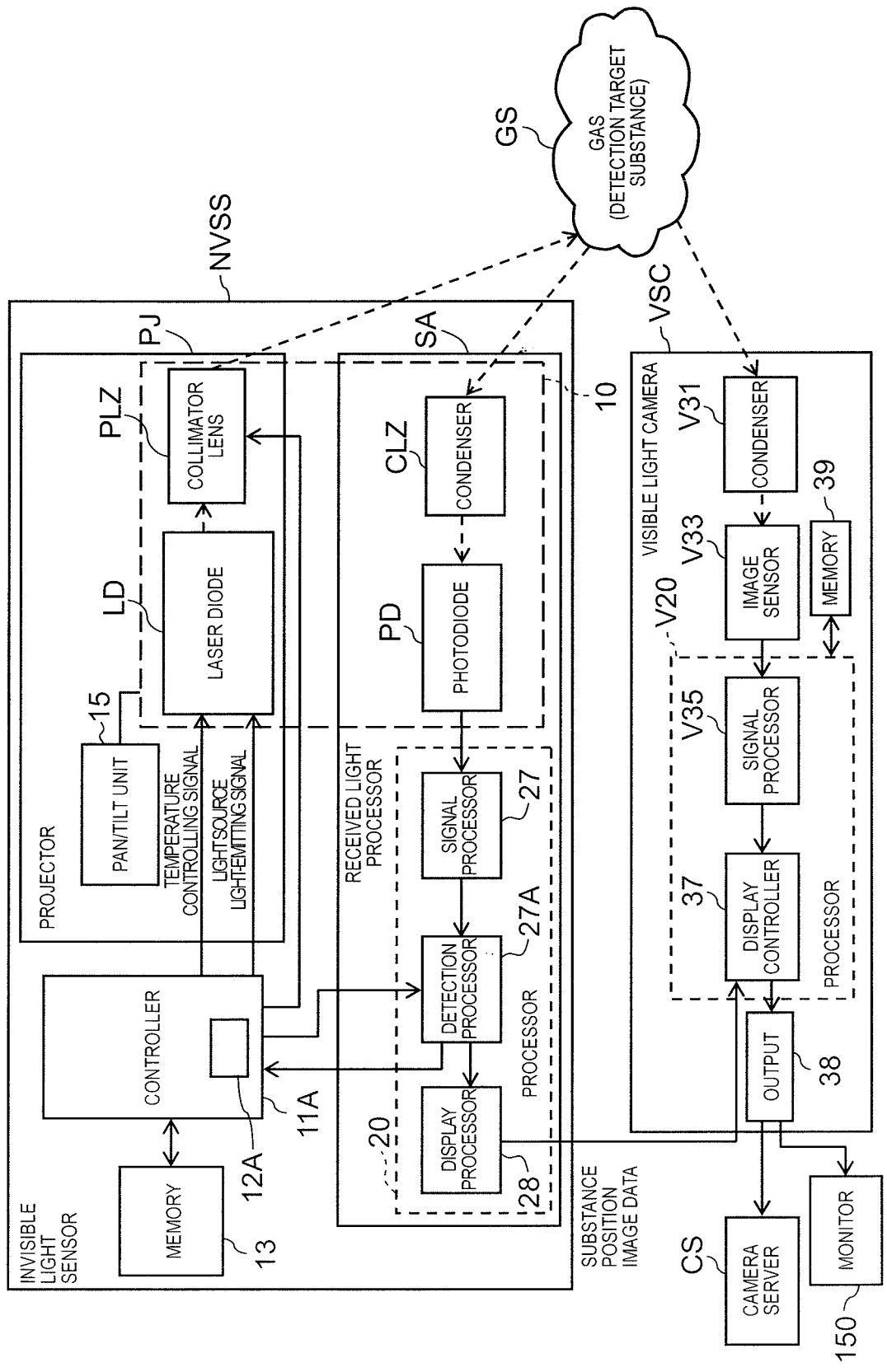
FIG. 24 is a block diagram illustrating an example of a configuration of the detection camera in the fourth embodiment.

FIG. 24 is a block diagram illustrating a configuration of detection camera 1 in the fourth embodiment.

As described above, detection camera 1 is configured to include invisible light sensor NVSS and visible light camera VSC. Invisible light sensor NVSS is configured to include controller 11A, projector PJ, and received light processor SA.

Controller 11A is configured by using a central processing unit (CPU), a micro processing unit (MPU), or a digital signal processor (DSP). For example, controller 11A performs signal processing for overall control of operation control of the members of invisible light sensor NVSS, input/output processing of data with the other members, arithmetic processing of data, and storage processing of data. In addition, controller 11A sets, to detection processor 27A, detection threshold M for detecting the specific substance as the detection target of invisible light sensor NVSS.

In addition, controller 11A transmits a timing signal for performing AD conversion to detection processor 27A. Controller 11A transmits, to laser diode LD, the light source light-emitting signal for modulating laser light LS that is emitted from laser diode LD.

Controller 11A includes wavelength detection/temperature controller 12A, inputs a temperature controlling state signal to be described below from detection processor 27A, generates a temperature controlling signal, and transmits the temperature controlling signal to laser diode LD. The temperature controlling signal is a signal for regulating the temperature of laser light LS that is emitted from laser diode LD and is a signal indicating heat absorption or heat emission with respect to a Peltier element included in laser diode LD. Laser diode LD changes the center wavelength of the wavelengths of laser light LS that is emitted, depending on a change in temperature.

In addition, controller 11A switches wavelength-modulation frequencies (modulation frequencies) of laser light LS. Controller 11A switches frequencies (detection frequencies) for detecting reflected laser light RV of laser light LS from the specific substance depending on the switch of modulation frequency. The detection frequency is twice modulation frequency. In addition, controller 11A switches the modulation frequencies or modulation frequencies with reference to setting information (for example, information of which timing the modulation frequencies or detection frequencies are switched or the like) stored in memory 13. Information of modulation frequency is included in the light source light-emitting signal and is transmitted to laser diode LD. Information of detection frequency is transmitted to detection processor 27A.

Projector PJ includes laser diode LD, collimator lens PLZ, and pan/tilt unit 15.

Laser diode LD emits laser light LS having an adjusted wavelength such that the wavelength of laser light LS is equal to the peak of an absorption wavelength band of gas GS which is the detection target substance. Here, an example of the gas which is the detection target substance includes methane gas ($CH_4$).

The wavelength is adjusted by using various types of methods.

For example, controller 11A modulates a drive current of laser diode LD as a semiconductor diode, thereby performing wavelength modulation of laser light LS that is emitted from laser diode LD. The drive current is an input signal of the semiconductor diode, and the frequency of the drive current is the modulation frequency. In addition, Peltier element Pt provided in laser diode LD absorbs or emits heat in response to the temperature controlling signal from controller 11A and changes the temperature of laser diode LD, thereby adjusting the center wavelength of the wavelength modulation of laser light LS.

Collimator lens PLZ changes laser light LS emitted from laser diode LD into parallel light.

Pan/tilt unit 15 swivels camera platform 10 in the pan direction and the tilt direction, on which laser diode LD, collimator lens PLZ, condenser CLZ, and photodiode PD are mounted. Pan/tilt unit 15 performs two-dimensional scanning within a scanning range including detection region SAR by using laser light LS that is emitted from laser diode LD.

Figure 25:
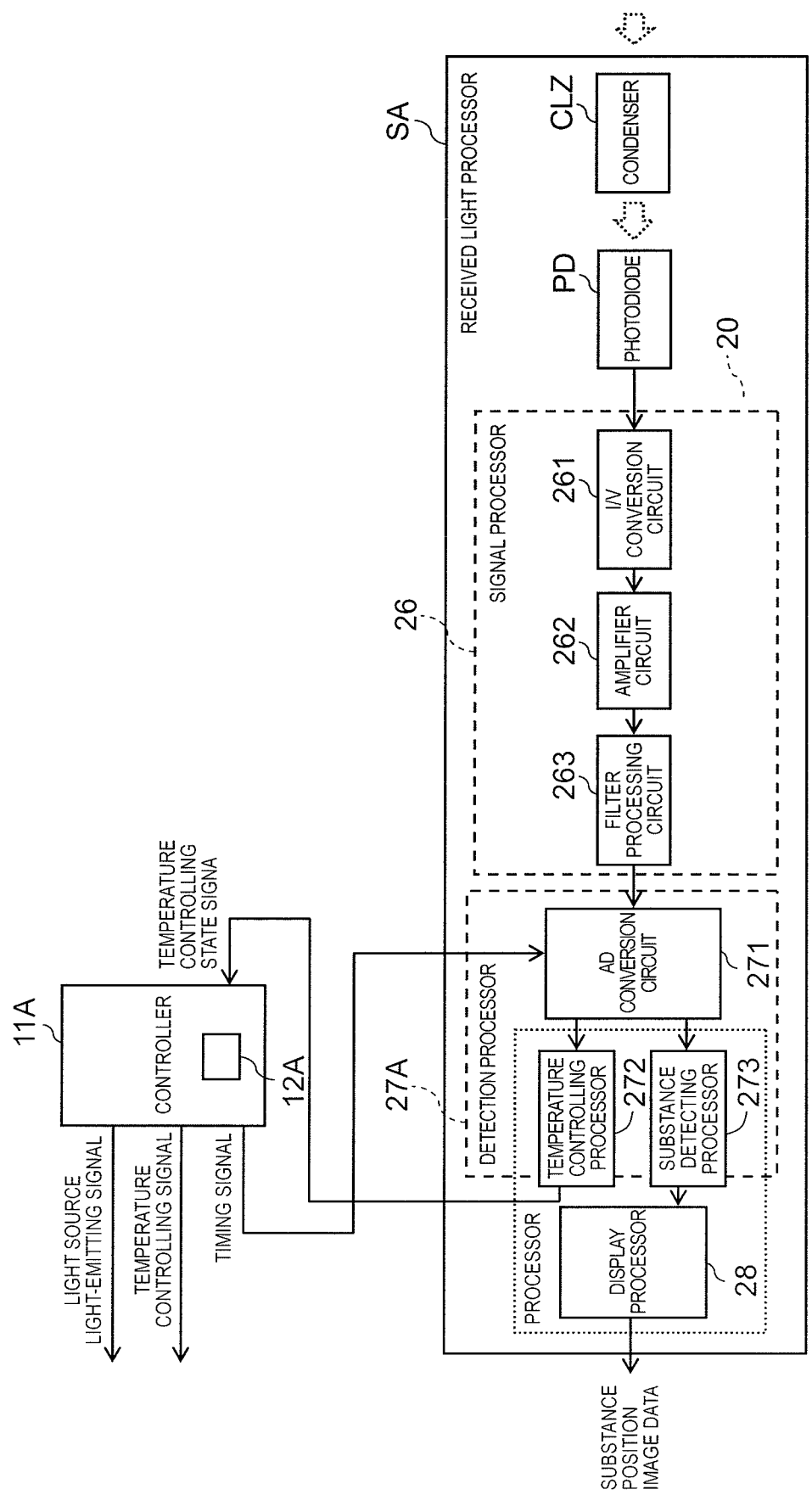
FIG. 25 is a block diagram illustrating an example of a configuration of a received light processor in the fourth embodiment.

FIG. 25 is a block diagram illustrating a configuration of received light processor SA in the fourth embodiment.

Received light processor SA includes condenser CLZ, photodiode PD, signal processing unit 26, detection processor 27A, and display processor 28. Signal processing unit 26 includes I/V conversion circuit 261, amplifier circuit 262, and filter processing circuit 263. Detection processor 27A includes AD conversion circuit 271, temperature controlling processor 272, and substance detection processor 273.

Processor 20 executes a program stored in memory 13, and thereby the functions of temperature controlling processor 272 and substance detection processor 273 and display processor 28 of detection processor 27A are realized.

Condenser CLZ condenses laser light RV which is emitted from laser diode LD and is reflected from the specific substance in detection region SAR, and the condensed laser light is received by photodiode PD. Photodiode PD generates electric charges corresponding to the intensity of received laser light RV and outputs the electric charges as a current signal.

I/V conversion circuit 261 converts the current signal output from photodiode PD into a voltage signal. Amplifier circuit 262 amplifies the voltage signal output from I/V conversion circuit 261. Filter processing circuit 263 performs filter processing on the signal amplified in amplifier circuit 262, and the filtered signal is output as a signal, which is used for the substance detection, to AD conversion circuit 271 in detection processor 27A.

AD conversion circuit 271 in detection processor 27A converts a signal input from signal processing unit 26 into a digital signal during the detection of the specific substance or the temperature control of laser diode LD.

Temperature controlling processor 272 generates a signal (temperature controlling state signal) indicating a temperature controlling state and outputs the signal to controller 11A, based on a value that is converted into the digital value in AD conversion circuit 271 in the temperature controlling operation. The temperature controlling state signal is a signal indicating a level of a signal (signal level) of frequency (2f) twice a signal (frequency 1f) of laser light LS that is emitted from laser diode LD and is subjected to the wavelength modulation.

The temperature of laser diode LD is not changed, and the modulation wavelength width of laser light LS that is emitted from laser diode LD is not shifted from the absorption wavelength band of the specific substance. In this case, the temperature controlling state signal is increased in level of the signal (signal level) of frequency (2f) twice frequency 1f.

The temperature of laser diode LD is changed, and the modulation wavelength width of laser light LS that is emitted from laser diode LD is shifted from the absorption wavelength band of the specific substance. In this case, the temperature controlling state signal becomes a signal having a change in frequency, is obtained based on the signal from photodiode PD2, and is decreased in level of the signal (signal level) of frequency (2f) twice frequency 1f is low.

Substance detection processor 273 detects the specific substance based on a value that is output from signal processing unit 26 in received light processor SA in the substance detecting operation and is converted into a digital value in AD conversion circuit 271, and a signal indicating a detection result of the specific substance is output to display processor 28.

Similar to the temperature controlling state signal, substance detection processor 273 obtains a signal indicating a level of a signal (signal level) of frequency (2f) twice the signal (frequency 1f) of laser light LS that is emitted from laser diode LD and is subjected to the wavelength modulation, based on the value converted into the digital value by AD conversion circuit 271. Substance detection processor 273 generates a signal indicating a detection result of the specific substance, based on the signal representing the size of the signal (signal level) of frequency (2f) twice the signal.

Display processor 28, from invisible light sensor NVSS, generates substance position image data indicating the two-dimensional position of the specific substance in detection region SAR. The substance position image data includes image data indicating the specific substance and two-dimensional position information (for example, the pan angle and the tilt angle of camera platform 10) in detection region SAR. Display processor 28 outputs the substance position image data to display controller 37 of visible light camera VSC.

As described above, information associated to the specific substance which is obtained by detection processor 27A is synthesized with the visible light image data in detection region SAR and the obtained data is displayed and output. Hence, invisible light sensor NVSS can visually and clearly show a user where the specific substance is present in detection region SAR.

For example, in the embodiments, display processor 28 may transmit the substance position image data to monitor 150, or camera server CS, which will be described below, or a communication terminal, instead of transmitting the data to display controller 37 in visible light camera VSC.

As illustrated in FIG. 24, visible light camera VSC includes condenser V31, image sensor V33, signal processor V35, display controller 37, and output 38. Processor V20 executes a program stored in memory 39, and thereby the functions of signal processor V35 and display controller 37 are realized.

Condenser V31 condenses incident light (reflected light RM) from outside with a range including detection region SAR, by invisible light sensor NVSS, and forms an image on a capturing surface of image sensor V33.

Image sensor V33 has the peak of spectral sensitivity with respect to a wavelength (for example, 0.4 μm to 0.7 μm) of visible light. Image sensor V33 converts an optical image formed on the capturing surface into an electric signal. Output from image sensor V33 is input as the electric signal into signal processor V35.

Signal processor V35 generates visible light image data defined by RGB (red, green, and blue), YUV (luminance/color difference), or the like by using the electric signal output from image sensor V33. In this manner, visible light image data captured by visible light camera VSC is generated. Signal processor V35 outputs the visible light image data to display controller 37.

In a case where the specific substance is detected at a predetermined position from the visible light image data, display controller 37 synthesizes the visible light image data output from signal processor V35 with the substance position image data output from display processor 28 and generates display data. The display data is an example of information associated with the specific substance.

Output 38 outputs the display data to external devices (for example, camera server CS and monitor 150).

Camera server CS transmits, to a communication terminal or one or more externally connected devices, the display data output from display controller 37 and promotes display of the display data on a display screen of the communication terminal or one or more externally connected devices.

Monitor 150 displays the display data output from display controller 37.

[Absorption Characteristics of Specific Substance]

FIG. 26 is a schematic diagram illustrating an input signal and an output signal of photodiode PD in a case where laser light LS emitted from laser diode LD has the optimal wavelength with respect to absorption spectra of the specific substance.

FIG. 26 illustrates methane gas (CH4) as an example of the gas which is the detection target substance. In FIG. 26, the vertical axis represents voltage (unit is a normalized value) received by photodiode PD, and the horizontal axis represents a wavelength (nm) of the laser light RV which is received by photodiode PD. The lower the received voltage, the higher the absorption rate of laser light LS by the specific substance. Absorption characteristics of a substance are determined depending on the substance.

In FIG. 26, the absorption spectra of the specific substance have a wavelength band having the center thereof at 1,653.67 nm. On the other hand, the laser light emitted from laser diode LD is modulated in a modulation width of 0.05 nm in which the center wavelength is at 1,653.67 nm as shown in wavelength modulating range WAR0.

As described above, laser light LS emitted from laser diode LD and laser light RV (input signal) reflected from the specific substance in detection region SAR is detected as a signal (output signal) having the frequency twice the signal of laser light RV by photodiode PD. In this case, the sine wave signal having the constant frequency is output.

In addition, controller 11A switches the modulation frequency to one of two frequencies of first modulation frequency (f1) and second modulation frequency (f2) and emits the laser light. Three or more modulation frequencies may be provided and switching to any one of the modulation frequencies may be performed.

In addition, controller 11A switches the detection frequency to one of two frequencies of first detection frequency (2×f1) and second detection frequency (2×f2) according to the switching of the modulation frequency. Three or more detection frequencies may be provided and switching to any one of the detection frequencies may be performed.

In other words, in photodiode PD, first output signal (2×f1) having a frequency twice first wavelength-modulated input signal (1×f1) is obtained. In addition, second output signal (2×f2) having a frequency twice second wavelength-modulated input signal (1×f2) is obtained.

Figure 27:
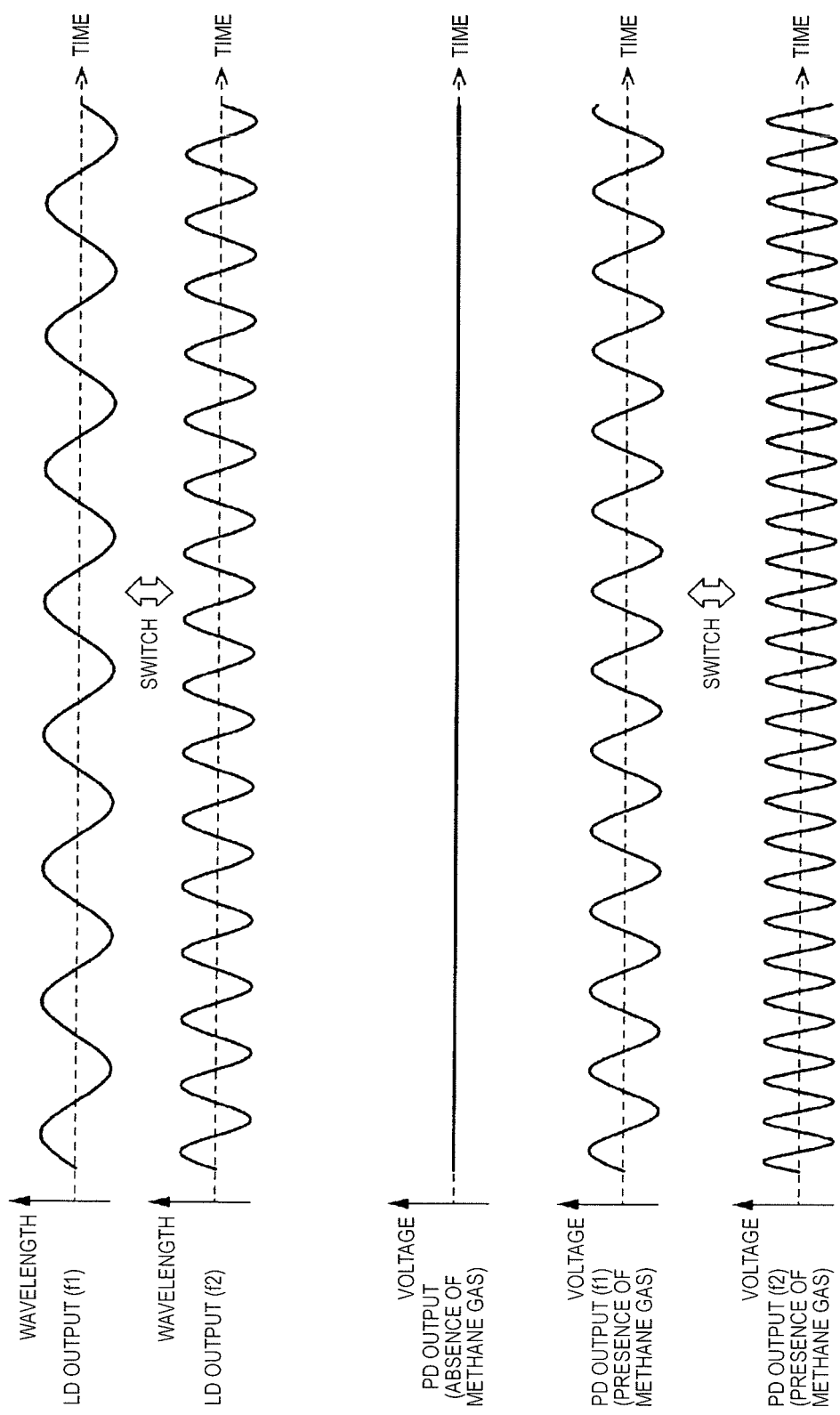
FIG. 27 is a graph illustrating an example of a time change of an output signal of a laser diode and an output signal of a photodiode.

FIG. 27 is a graph illustrating an example of a time change of the output signal and the output signal of photodiode PD. In FIG. 27, an "LD output" represents a signal of an output (that is, laser light LS) of laser diode LD, and the vertical axis represents a wavelength. In addition, a "PD output" represents a signal that is output from photodiode PD (hereinafter, similar in FIGS. 28 to 30).

A signal that is received by photodiode PD (input to photodiode PD) has a frequency twice a modulation frequency of laser light LS that is emitted from laser diode LD in a case where the detection target object is present.

In addition, the frequency of the signal that is output from photodiode PD, that is, the detection frequency, is twice the modulation frequency. Hence, in a case where the modulation frequency of laser light LS is first modulation frequency f1, the first detection frequency for detecting laser light RV subjected to the wavelength modulation with first modulation frequency f1 is frequency (2×f1) twice first modulation frequency f1. In addition, in a case where the modulation frequency of laser light LS is second modulation frequency f2, the second detection frequency for detecting laser light RV subjected to the wavelength modulation with second modulation frequency f2 is frequency (2×f2) twice second modulation frequency f2.

For example, second modulation frequency f2 is set to 5/3 of first modulation frequency f1. 5/3 times is an example, and the frequency may be set to any other times. For example, first modulation frequency f1 is set to 1.5 Hz, and second modulation frequency f2 is set to 2.5 Hz. Second modulation frequency f2 may be set to be defined in a multiplying process of first modulation frequency f1.

In addition, laser light LS which is emitted from laser diode LD is reflected from a substance in detection region SAR, and the reflected laser light is received by photodiode PD. In this case, the signal level of the input signal to photodiode PD is a value of 0 in a case where gas (for example, methane gas: CH4) that is the specific substance is not found in detection region SAR (no presence). Therefore, the signal level of the output signal of laser diode LD also is the value of 0.

In a case where gas is found in detection region SAR (presence), first detection frequency becomes frequency (f1×2) with respect to first modulation frequency f1, and thus a signal including a signal having the frequency is obtained. Similarly, the second detection frequency is a frequency (f2×2) with respect second modulation frequency f2, and thus a signal including a signal having the frequency is obtained. An example of using two modulation frequencies is described; however, three or more modulation frequencies may be used.

[Operation and the Like]

Next, an operation of detection camera 1 will be described.

In addition, three substance detecting operations are described.

FIG. 28 is a schematic diagram for illustrating spot detection in the substance detecting operation. In the spot detection, invisible light sensor NVSS irradiates one point in detection region SAR with laser light LS and detects the specific substance.

In a case of the spot detection, Invisible light sensor NVSS obtains signal sg1, as the output signal from photodiode PD, which does not have frequency (2f) twice the modulation frequency when the specific substance (for example, methane gas) is not present. On the other hand, when the specific substance is present, invisible light sensor NVSS obtains signal sg2, as an output signal from photodiode PD, which has frequency (2f) twice the modulation frequency.

FIG. 29 is a diagram for illustrating area detection in a case where there is no background change in the substance detecting operation. In the area detection, invisible light sensor NVSS performs line scanning in the horizontal direction and vertical direction in detection region SAR, irradiates the detection region with laser light LS, and detects the specific substance.

In a case of the area detection, Invisible light sensor NVSS obtains signal sg3, as the output signal from photodiode PD, which does not have frequency (2f) twice the modulation frequency when the specific substance is not present. On the other hand, when the specific substance is present, invisible light sensor NVSS obtains signal sg4, as an output signal from photodiode PD, which has frequency (2f) twice the modulation frequency.

FIG. 30 is a schematic diagram for illustrating the area detection in a case where there is a background change in the substance detecting operation. Examples of the background change include a stripe pattern of white and black applied on a wall surface. White has high reflectance of light and black has low reflectance of light.

In a case where scanning with the laser light is performed in a direction orthogonal to the stripe pattern in FIG. 30, invisible light sensor NVSS obtains signal sg10, as the output signal from photodiode PD, which changes along with the background change even when the specific substance is not present. Therefore, when a background change rate approximates first detection frequency (2×f1), invisible light sensor NVSS obtains a signal having a possibility that false detection of the presence of the specific substance is made. Here, the background change rate is the same as the reflectance of the laser light and is also referred to as background reflectance.

In addition, when the substance detection is performed by using second detection frequency (2×f2), the background change rate does not approximate second detection frequency (2×f2) in a case where the background change rate approximates first detection frequency (2×f1). Therefore, invisible light sensor NVSS obtains signal sg11, as the output signal from photodiode PD, which does not have second detection frequency (2×f2).

As described above, in a case where the specific substance is not present, at least one detection frequencies 2×f1, and 2×f2 does not approximate the background change rate. Therefore, invisible light sensor NVSS obtains different results of the substance detection. Hence, in a case where detected results obtained by using two modulation frequencies f1 and f2 are different from each other, invisible light sensor NVSS is capable of determining that one result is false and that the specific substance is not present.

On the other hand, in a case where the specific substance is present and the background change rate approximates first detection frequency (2×f1), a signal of first detection frequency (2×f1) and a signal indicating the background change rate are added to each other. Therefore, invisible light sensor NVSS obtains signal sg12, as the output signal from photodiode PD, which has first detection frequency (2×f1) and a high signal level.

In addition, when the substance detection is performed by using second detection frequency (2×f2), the background change rate does not approximate second detection frequency (2×f2) in a case where the background change rate approximates first detection frequency (2×f1). Therefore, a signal of second detection frequency (2×f2) is distinguished from a signal indicating the background change rate, and invisible light sensor NVSS obtains signal sg13, as the output signal from photodiode PD, which has second detection frequency (2×f2) and a normal signal level.

Hence, in the case where the specific substance is present, the results of the substance detection performed by using two modulation frequencies f1 and f2 are the same.

As described above, in the case where the specific substance is present, invisible light sensor NVSS outputs a signal of a frequency (1×2f or 2×2f) twice any one of the modulation frequencies even when one detection frequency 1×2f or 2×2f approximates the background change rate by using two modulation frequencies f1 and f2. Hence, invisible light sensor NVSS can determine that the specific substance is present without outputting a signal of false detection that the specific substance is not present.

Figure 31:
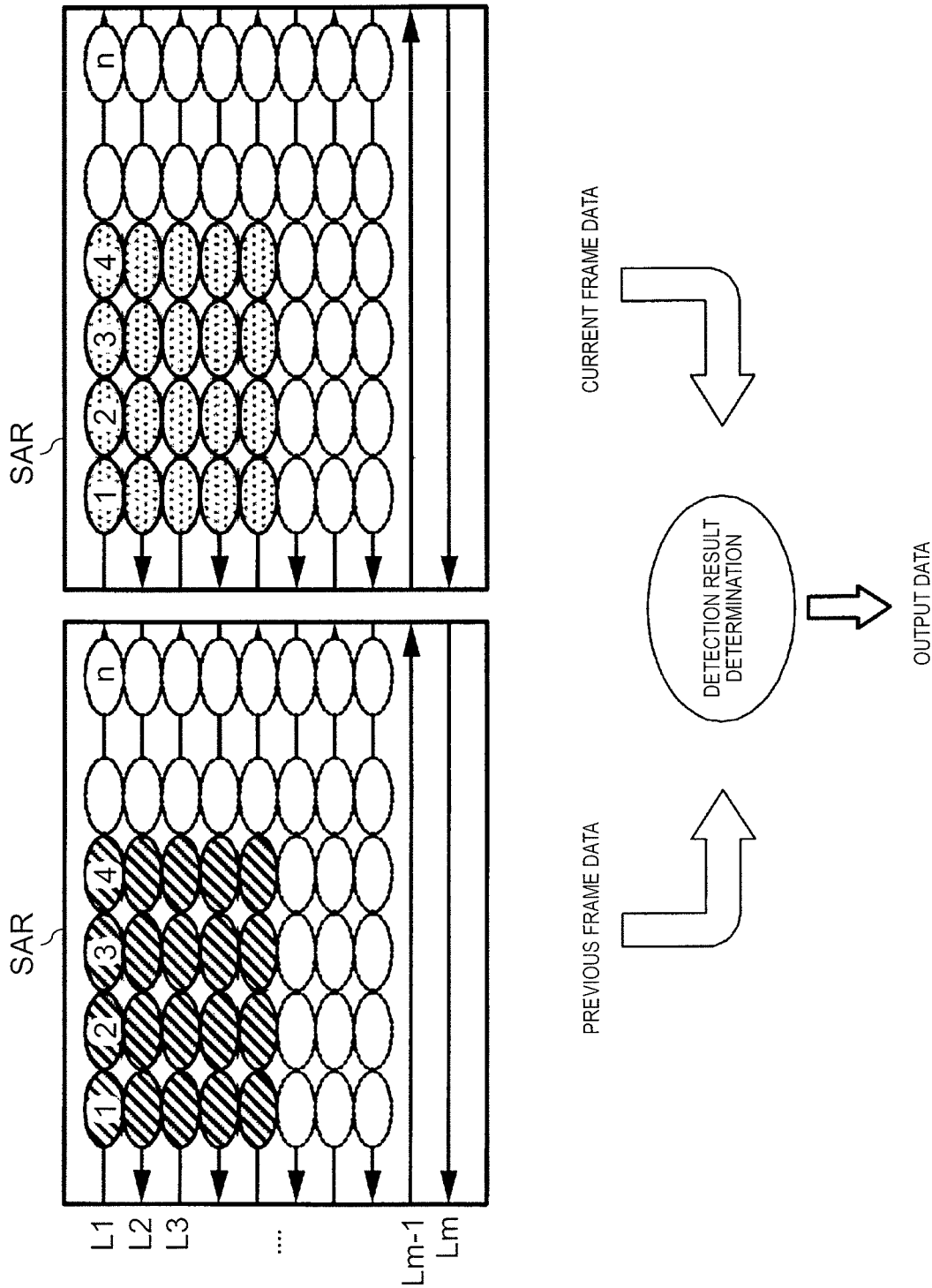
FIG. 31 is a schematic diagram for illustrating an example of determination of a substance detection result.

FIG. 31 is a schematic diagram for illustrating the determination of the substance detection result.

As described below, controller 11A of invisible light sensor NVSS switches the modulation frequency and the detection frequency in accordance with a predetermined condition (for example, per frame, per line, or per unit region). In FIG. 31, switching of the modulation frequency and the detection frequency per frame is illustrated.

The frame corresponds to entire detection region SAR which is scanned. The line is the same row (line) which is scanned. The unit region is the smallest region of a scanning target in detection region SAR. When scanning of one frame in detection region SAR is ended, scanning of the next frame in detection region SAR is performed.

For example, laser diode LD irradiates the previous frame (first frame) with laser light LS at first modulation frequency f1. Laser diode LD irradiates the current frame (second frame) with laser light LS at second modulation frequency f2.

In FIG. 31, Reference marks 1, 2, . . . , and n assigned to lines (L1, L2, and Lm) in detection region SAR represent irradiation positions of laser light LS. Detection processor 27A compares the detection results of the specific substance with the laser light of the modulation frequency f1 in the previous frame to the detection results of the specific substance with the laser light of the modulation frequency f2 in the current frame, for the irradiation positions.

In a case where both of the detection results do not match each other, false detection is generated, and detection processor 27A determines that the specific substance is not present. On the other hand, in a case where both of the detection results match each other, false detection is not generated, and detection processor 27A determines that the specific substance is present.

Figure 32:
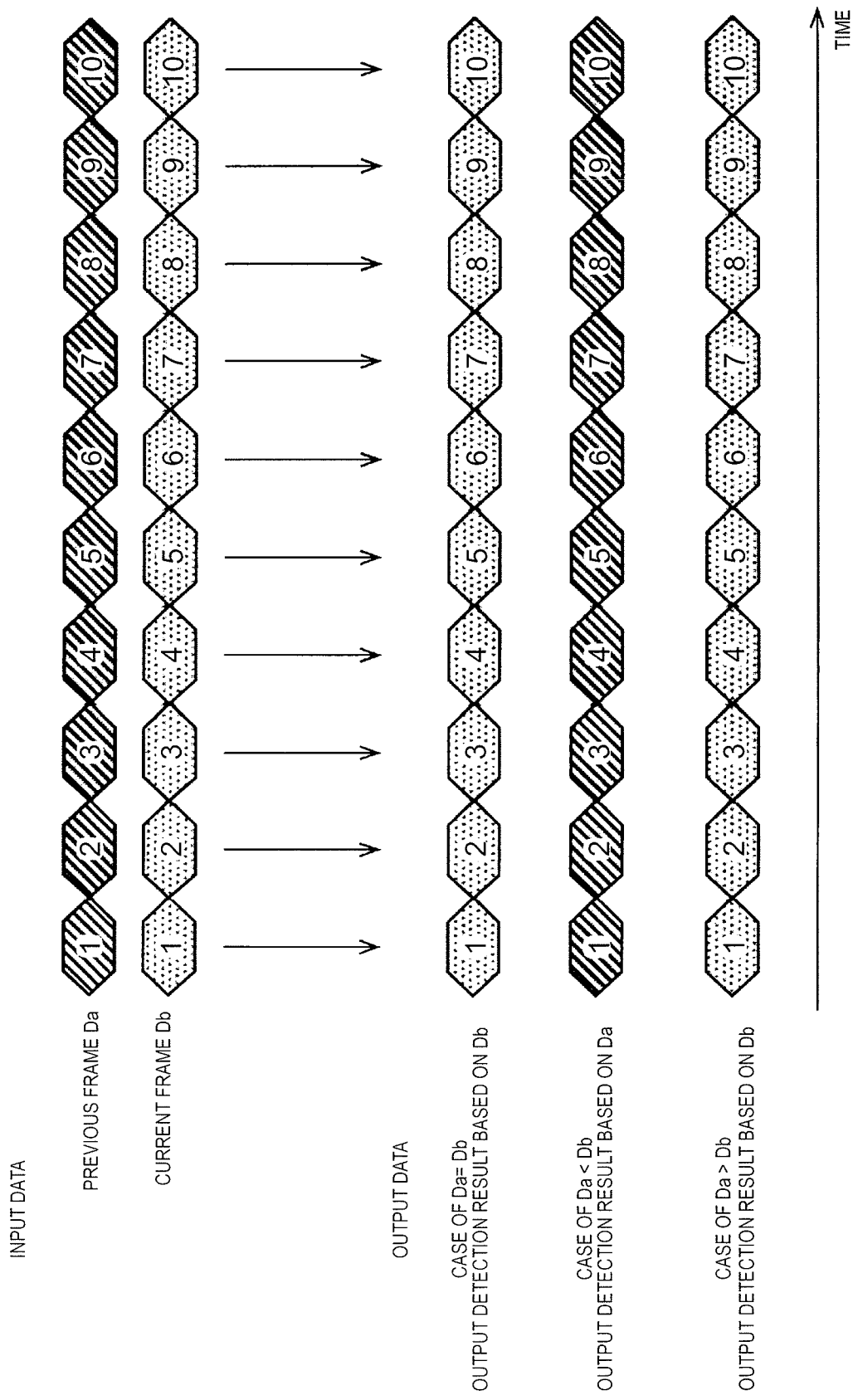
FIG. 32 is a schematic diagram for illustrating another example of determination of a substance detection result in detail.

FIG. 32 is a schematic diagram for illustrating determination of the substance detection result in detail. In FIG. 32, similar to FIG. 31, switching of the modulation frequency and the detection frequency per frame is illustrated.

"Input data" illustrated in FIG. 32 is data of the detection result of the specific substance with respect to one frame. The input data is stored in memory 13 so as to be compared to the detection result of the specific substance with respect to another frame. The input data includes information of the presence or absence of the specific substance and information of the signal level of the output signal from photodiode PD, which is acquired via signal processing unit 26. The information of the signal level of the output signal included in the input data is simply referred to as the signal level of the input data.

"Output data" illustrated in FIG. 32 is a detection result output by detection processor 27A as a result of comparison of the detection result of the specific substance with respect to one frame to the detection result of the specific substance with respect to another frame. For example, the output data includes the information of the presence or absence of the specific substance.

Detection processor 27A compares a plurality of items of input data and outputs the output data based on any input data.

In FIG. 32, Reference Marks 1, 2, . . . , and 10 represent the irradiation positions of laser light LS. As described above, in a case where the presence or absence of the specific substance included in input data Da of the previous frame is the same as the presence or absence of the specific substance included in input data Db of the current frame at the same irradiation position, detection processor 27A determines that the specific substance is present or is not present without false detection. Detection processor 27A outputs the information of the presence or absence of the specific substance, as the output data, based on input data Db of the current frame.

On the other hand, the presence or absence of the specific substance included in input data Da of the previous frame is different from the presence or absence of the specific substance included in input data Db of the current frame, and the signal level of input data Da is lower than the signal level of input data Db. In this case, detection processor 27A outputs the information of the presence or absence of the specific substance, as the output data, based on input data Da having the low signal level.

In addition, the presence or absence of the specific substance included in input data Da of the previous frame is different from the presence or absence of the specific substance included in input data Db of the current frame, and the signal level of input data Da is higher than the signal level of input data Db. In this case, detection processor 27A outputs the information of the presence or absence of the specific substance, as the output data, based on input data Db having the low signal level.

In other words, in a case where the presence or absence of the specific substance included in input data Da of the previous frame is different from the presence or absence of the specific substance included in input data Db of the current frame at the dame irradiation position, false detection occurs, and detection processor 27A determines that the specific substance is not present. Detection processor 27A outputs the information indicating that the specific substance is not present, as the output data, based on input data Da or Db having the low signal level.

Figure 33:
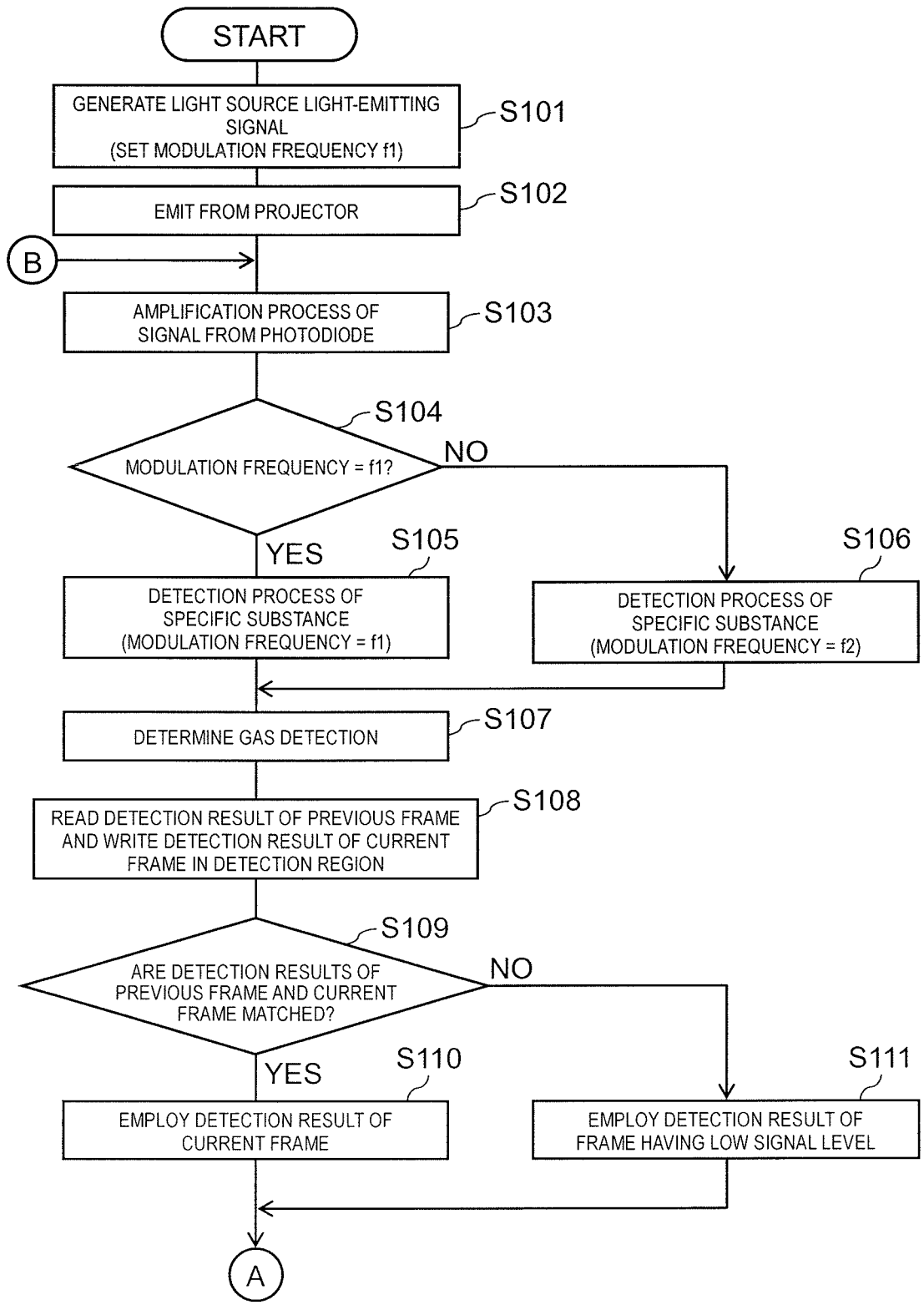
FIG. 33 is a flowchart illustrating an example of a substance detecting operation performed by the invisible light sensor.
Figure 34:
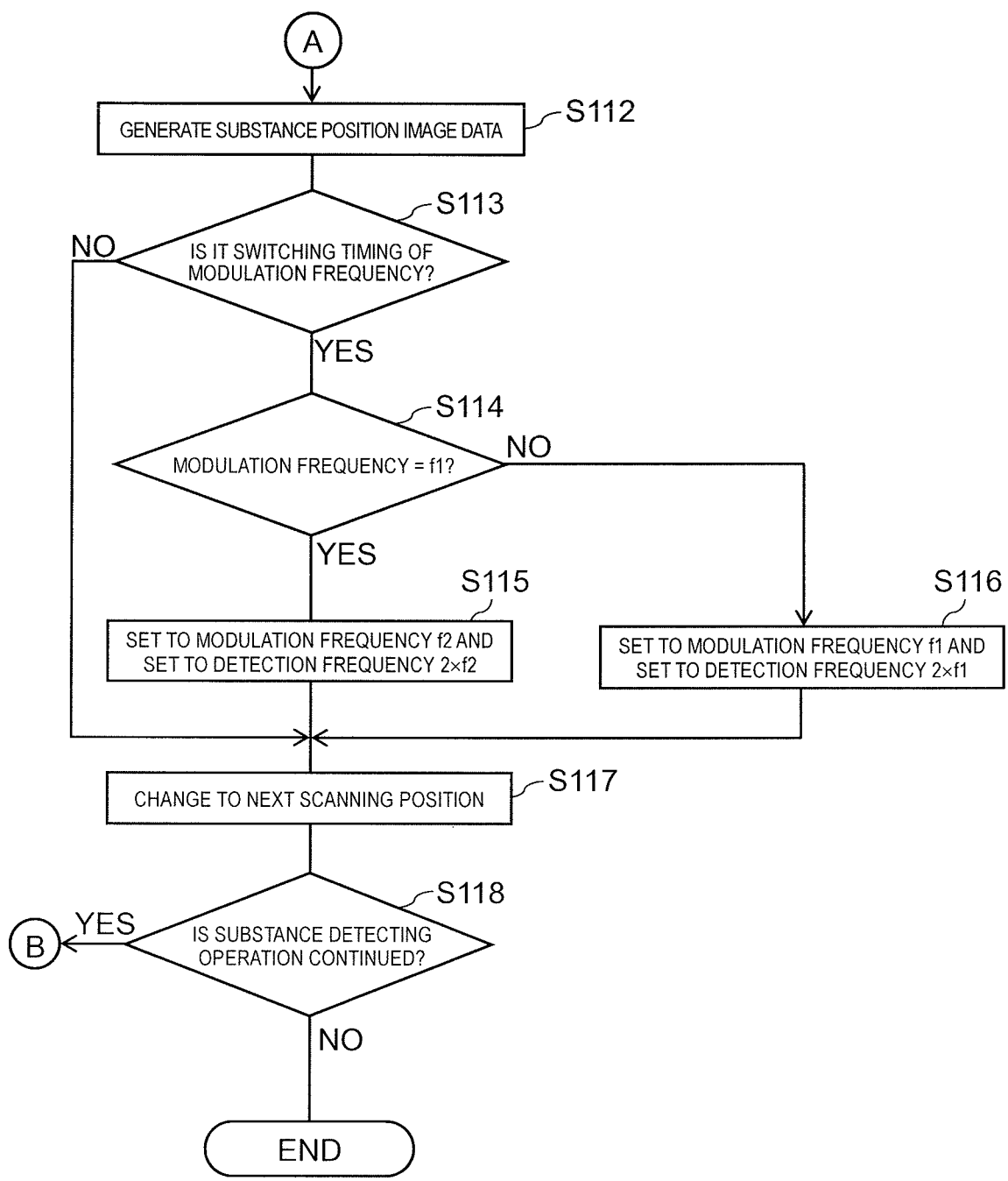
FIG. 34 is a flowchart (continued from FIG. 33) illustrating an example of the substance detecting operation performed by the invisible light sensor.

FIGS. 33 and 34 are flowcharts illustrating an example of the substance detecting operation performed by invisible light sensor NVSS.

Controller 11A determines the modulation frequency of laser light LS and performs initial setting of the light source light-emitting signal (S101). For example, the modulation frequency is set to first modulation frequency f1(<f2) in the initial setting. The set information (setting information) is stored in memory 13.

Projector PJ emits laser light LS depending on the modulation frequency set in the control by controller 11A (S102). Emitted laser light LS is reflected from a substance in detection region SAR, and laser light RV is incident to photodiode PD. Photodiode PD outputs a signal based on incident laser light RV.

Signal processing unit 26 inputs the signal (output signal from photodiode PD) from photodiode PD and amplifies the signal (S103).

Detection processor 27A determines whether or not the modulation frequency is first modulation frequency f1 with reference to the setting information stored in memory 13 (S104).

In a case where the modulation frequency is first modulation frequency f1, detection processor 27A performs a detection process of the specific substance by using first detection frequency (2×f1) (S105) and determines whether or not gas that is the specific substance is detected (S107). Here, detection processor 27A extracts the signal of first detection frequency (2×f1) from signals amplified by signal processing unit 26 and determines the presence or absence of the specific substance. For example, the presence or absence of gas GS is determined, depending on whether or not the signal of first detection frequency (2×f1) is equal to or higher than detection threshold M. The detection process of the specific substance is performed for each unit region.

Detection processor 27A reads, from memory 13, the detection results (corresponding to input data Da illustrated in FIG. 32) of the specific substance in the current frame in detection region SAR (S108). In addition, detection processor 27A writes, to memory 13, the detection results (corresponding to input data Db illustrated in FIG. 32) of the specific substance in the current frame (S108). The detection results of the specific substance in the current frame, which is stored in memory 13, and the detection results of the specific substance in the next frame are used in the next detection process of the specific substance.

Detection processor 27A determines whether or not the detection results (the presence or absence of the specific substance) related to the previous frame match the detection results (the presence or absence of the specific substance) related to the current frame (S109).

In a case where the detection results related to the previous frame match the detection results related to the current frame, detection processor 27A employs the detection results related to the current frame and transmits the detection results related to the current frame (here, information of the presence or absence of the specific substance) to display processor 28 (S110).

In a case where the detection results related to the previous frame do not match the detection results related to the current frame, detection processor 27A employs the detection results related to a frame, of which the signal level of the output signal from photodiode PD is lower, and transmits the detection results related to the corresponding frame (here, information of the presence or absence of the specific substance) to display processor 28 (S111).

In other words, in a case where data of the detection results related to a frame having a low light receiving level is output, detection processor 27A uses data of the detection, in which the specific substance is not detected, as data of correct detection results because false detection occurs.

In a case where the modulation frequency is second modulation frequency f2 in S4, detection processor 27A performs a detection process of the specific substance by using second detection frequency (2×f2) (S106) and determines whether or not gas that is the specific substance is detected (S107). Even in a case of using second detection frequency (2×f2), invisible light sensor NVSS performs processes of S8 to S11, similar to the case of using first detection frequency (1×f1).

Display processor 28 generates the substance position image data, based on the detection results of the specific substance from detection processor 27A and outputs the substance position image data to display controller 37 (S112). For example, in a case where gas GS which is the specific substance is present, the substance position image data includes an image showing a position (direction) of the specific substance. Display controller 37 superimposes the substance position image data on the image data captured by visible light camera VSC, generates display data, and outputs the generated data to camera server CS and monitor 150 via output 38.

Controller 11A determines whether or not it is a switching timing of the modulation frequency (S113). For example, controller 11A determines that it is the switching timing of the modulation frequency at a switching timing of the frame, the line, and the irradiation position (unit region).

In a case where it is not the switching timing, pan/tilt unit 15 changes the scanning position (S117). In other words, pan/tilt unit 15 drives camera platform 10 and causes every devices mounted on camera platform 10 to move to the next scanning position of laser light LS. The devices include laser diode LD, collimator lens PLZ, photodiode PD, and condenser CLZ.

Controller 11A determines whether or not the substance detecting operation is continued (S118). For example, whether or not the substance detecting operation is continued depends on the setting information stored in memory 13, a time point, a power on/off operation of detection camera 1 or invisible light sensor NVSS.

In a case where the substance detecting operation is continued, invisible light sensor NVSS proceeds to the process in S3. In a case where the substance detecting operation is not continued, invisible light sensor NVSS ends the processes illustrated in FIGS. 33 and 34.

In addition, in a case where it is the switching timing of the modulation frequency in S113, controller 11A determines whether or not the modulation frequency is set to first modulation frequency f1 with reference to memory 13 (S114).

In a case where the modulation frequency is set to first modulation frequency f1, controller 11A sets the modulation frequency to second modulation frequency f2 and stores the setting information in memory 13 (S115). On the other hand, in a case where the modulation frequency is set to second modulation frequency f2, controller 11A sets the modulation frequency to first modulation frequency f1 and stores the setting information in memory 13 (S116). After the processes in S115 and S116 are performed, invisible light sensor NVSS proceeds to the process in S117.

FIGS. 33 and 34 illustrate examples in which the modulation frequency can be set to any of the two frequencies; however, as described above, the modulation frequency may be set to any frequency of three or more frequencies. In this case, the modulation frequency after the switching may be set in a predetermined order or may be set in an arbitrary order.

[Details of Modulation Pattern]

Figure 35:
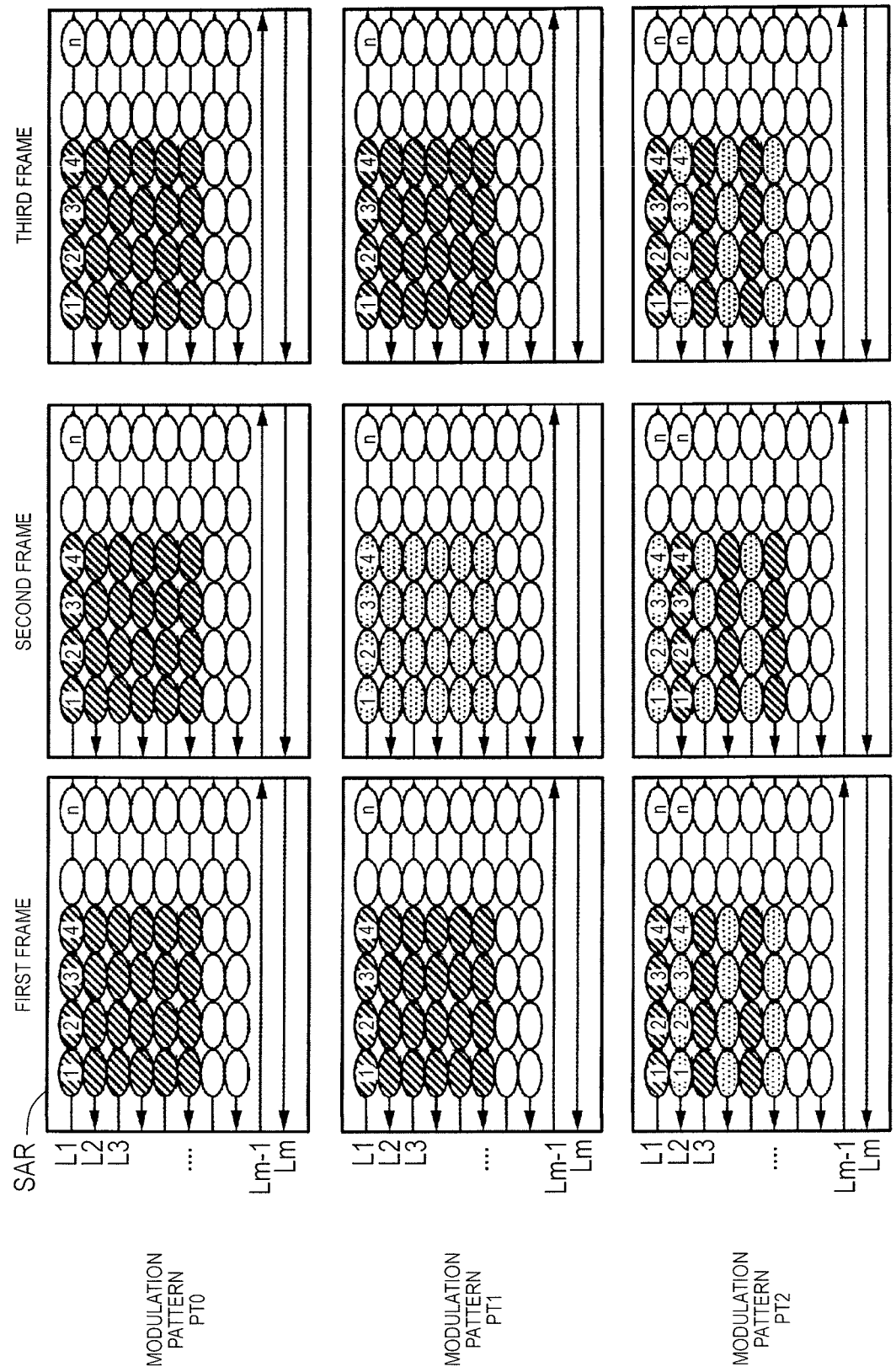
FIG. 35 is a schematic diagram illustrating an example of a modulation pattern.
Figure 36:
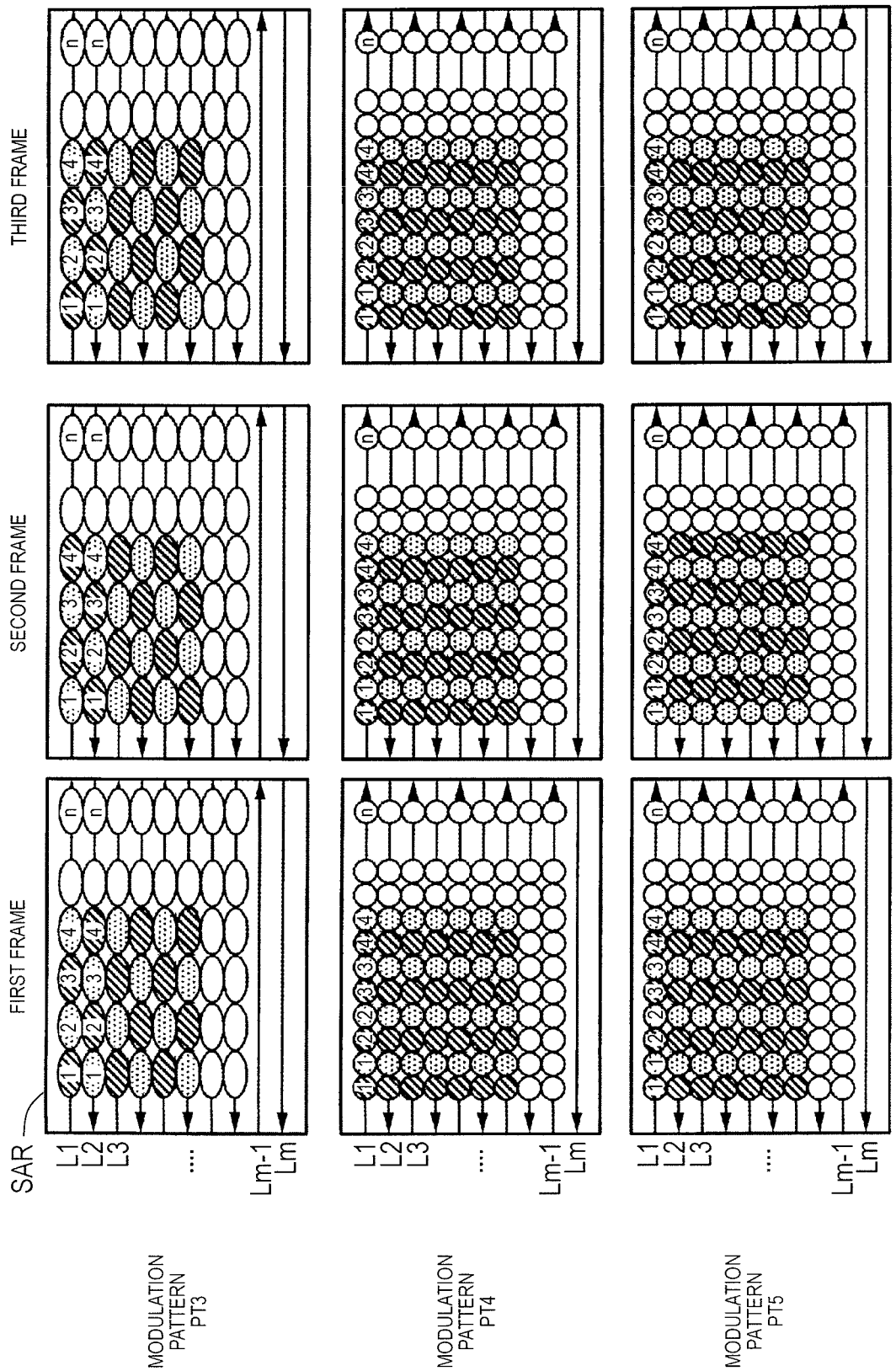
FIG. 36 is a schematic diagram illustrating another example of the modulation pattern.

As a method of switching the modulation frequencies, a plurality of variations (modulation patterns) are assumed. FIGS. 35 and 36 are schematic diagrams illustrating modulation patterns PT0 to PT5. In FIGS. 35 and 36, L1. L2, L3, . . . , and Lm represent line numbers in the horizontal direction. In addition, Reference marks 1, 2, 3, . . . , and n represent irradiation positions of laser light LS in detection region SAR. Information indicating which modulation pattern is set by controller 11A and whether the switching of the modulation frequencies is performed is stored in memory 13 in advance.

Also as a method of switching the detection frequencies, a plurality of variations (detection patterns) are assumed. Since the detection pattern is set corresponding to the modulation pattern in the same manner, the detailed description thereof is omitted.

In modulation pattern PT0, a case where controller 11A fixes the modulation frequencies without switching the modulation frequencies is described. In modulation pattern PT0, the modulation frequency is fixed as first modulation frequency f1 in any frame.

In modulation pattern PT1, a case where controller 11A switches the modulation frequencies alternately by frame unit (detection operation one time in entire detection region SAR) is described (frame order).

In the first frame, the modulation frequency is first modulation frequency f1. In the second frame, the modulation frequency is second modulation frequency f2. In the third frame, the modulation frequency is first modulation frequency f1.

In modulation pattern PT2, a case where controller 11A switches the modulation frequencies alternately for each line in the horizontal direction and a modulation frequency at a start position is changed for each frame is described (line order).

In the first frame, the modulation frequency is set to first modulation frequency f1 in the first line, and the modulation frequency is set to second modulation frequency f2 in the second line. Then, the modulation frequency is alternately set to first modulation frequency f1 or second modulation frequency f2 by line.

In the second frame, the modulation frequency is set to second modulation frequency f2 in the first line, and the modulation frequency is set to first modulation frequency f1 in the second line. Then, the modulation frequency is alternately set to first modulation frequency f1 or second modulation frequency f2 by line. From the third frame, the first frame and the second frame are repeated.

In modulation pattern PT3, controller 11A alternately switches the modulation frequencies for each irradiation position (unit region) (unit region order).

In the first line of the first frame, the modulation frequency is set to first modulation frequency f1 at a first irradiation position, and the modulation frequency is set to second modulation frequency f2 at a second irradiation position adjacent to the first irradiation position. Similar to the first irradiation position and the second irradiation position, the modulation frequencies are alternately switched at irradiation positions from the third irradiation position.

In the second line of the first frame, the modulation frequency is set to second modulation frequency f2 at the first irradiation position, and the modulation frequency is set to first modulation frequency f1 at the second irradiation position. Similar to the first irradiation position and the second irradiation position, the modulation frequencies are alternately switched at irradiation positions from the third irradiation position. From the third line, the first and second lines are repeated.

In the first line of the second frame, the modulation frequency is set to second modulation frequency f2 at the first irradiation position, and the modulation frequency is set to first modulation frequency f1 at the second irradiation position. Similar to the first irradiation position and the second irradiation position, the modulation frequencies are alternately switched at irradiation positions from the third irradiation position.

In the second line of the second frame, the modulation frequency is set to first modulation frequency f1 at the first irradiation position, and the modulation frequency is set to second modulation frequency f2 at the second irradiation position. Similar to the first irradiation position and the second irradiation position, the modulation frequencies are alternately switched at irradiation positions from the third irradiation position. From the third line, the first and second lines are repeated.

From the third frame, the first frame and the second frame are repeated.

In modulation patterns PT0 to PT3, controller 11A is assumed to irradiate the first irradiation position with laser light LS by one modulation frequency. In modulation patterns PT4 and PT5, controller 11A divides one irradiation position and irradiates the divided positions with laser light LS by two different modulation frequencies.

In modulation pattern PT4, controller 11A irradiates the irradiation positions on the entire line of the entire frame with the laser light in an order of first modulation frequency f1 and second modulation frequency f2. In other words, controller 11A sets the same phase in the same unit region without switching the modulation frequencies for each frame.

In modulation pattern PT5, controller 11A alternately switches the modulation frequencies for each frame at the irradiation positions in an order of modulation frequencies f1 and f2. In other words, the irradiation positions of the first frame are irradiated with the laser light in the order of first modulation frequency f1 and second modulation frequency f2, and the irradiation positions of the second frame are irradiated with the laser light in the order of first modulation frequency f1 and second modulation frequency f2. In other words, controller 11A switches the modulation frequencies for each frame and alternately switches phases in the same unit region.

As described above, invisible light sensor NVSS switches the modulation frequencies by line or by irradiation position, thereby controlling an influence of the background change rate and making it possible to detect the specific substance even in a portion in which a change in background is significant in detection region SAR. Similarly, the substance detection is performed in the same unit region by using a plurality of detection frequencies, and thereby it is possible to control the influence of the background change rate and to detect the specific substance even in a portion in which a change in background is significant in detection region SAR.

[Effects and the Like]

As described above, detection camera 1 includes laser diode LD, photodiode PD, detection processor 27A, pan/tilt unit 15, and controller 11A. Laser diode LD performs the wavelength modulation and emits laser light LS to the inside of detection region SAR of the substance. Photodiode PD receives laser light RV which is reflected light of laser light LS reflected from the substance in detection region SAR. Detection processor 27A detects the substance (for example, gas GS), based on the wavelength characteristics of laser light RV. Pan/tilt unit 15 changes the emitting direction of laser light LS and the receiving direction of laser light RV in detection region SAR. Controller 11A changes the modulation frequency which is the frequency of wavelength modulation of laser light LS and the detection frequency corresponding to the modulation frequency for detecting the substance by detection processor 27A.

Laser diode LD is an example of a transmitter. Photodiode PD is an example of a receiver. Detection processor 27A is an example of a detector. Pan/tilt unit 15 is an example of an actuator. Controller 11A is an example of a controller.

In this manner, controller 11A changes the modulation frequency and performs irradiation with the laser light from laser diode LD. Detection processor 27A detects the specific substance based on wavelength characteristics of laser light RV by using the detection frequency corresponding to the changed modulation frequency. Hence, even in a case where the background reflectance rate is not uniform, detection camera 1 can improve the detection accuracy of the substance. In addition, in a case where the modulation frequency and the detection frequency are switched by time division, detection camera 1 can change the specific substance (target) as the detection target object by time division.

In addition, laser diode LD may emit laser light LS a plurality of times in detection region SAR. Photodiode PD may receive laser light RV a plurality of times in detection region SAR. Detection processor 27A may repeat a detection operation for detecting gas GS which is the specific substance, a plurality of times in detection region SAR. Controller 11A may change the modulation frequency and the detection frequency for every detection operation in entire detection region SAR (frame), for each detection operation on the line parallel to a predetermined direction in detection region SAR, or for each unit region in detection region SAR.

In this manner, detection camera 1 can switch the modulation frequency and the detection frequency by various methods and it is possible to improve the detection accuracy of the substance. For example, even in a case where absorption characteristics in the wavelength modulation of one modulation frequency and the detection frequency and characteristics of the background change are similar to each other, detection camera 1 can perform setting in which the absorption characteristics in the wavelength modulation of one modulation frequency and the detection frequency and characteristics of the background change are distinguished from each other.

In addition, detection processor 27A may repeatedly perform detection of the substance by using first detection frequency (2×f1) and detection of the substance by using second detection frequency (2×f2), in an arbitrary region in detection region SAR.

In this manner, detection camera 1 can achieve at least one detection result of the substance by using the detection frequency that is different from the background reflectance in the same region at any timing, and can improve the detection accuracy of the substance.

In addition, detection processor 27A may perform, by one detection operation, detection of the substance by using first detection frequency (2×f1) and detection of the substance by using second detection frequency (2×f2), in the same unit region SAR.

In this manner, detection camera 1 can perform the substance detection by using a plurality of detection frequencies in the same unit region, and thus it is possible to improve detection of the substance.

In addition, detection processor 27A may determine that the specific substance is not present in any region in detection region SAR in a case where the detection results of the substance by using first detection frequency (2×f1) are different from the detection results of the substance by using second detection frequency (2×f2), in any region in detection region SAR.

In this manner, detection camera 1 can reduce the false detection of the specific substance, and thus it is possible to improve the detection accuracy of the substance.

Modification Example of Fourth Embodiment

As described above, the fourth embodiment is described as an example of the technology according to this disclosure.

However, the technology according to this disclosure is not limited thereto, and may be applied to an embodiment in which modification, replacement, addition, omission, or the like is performed.

In the fourth embodiment, the laser light transmitted through reference cell CEL is received by photodiode PD for substance detection and is processed by received light processor SA; however, a temperature controlling unit may be provided in the housing, separately from photodiode PD for substance detection. The temperature controlling unit includes a condenser, a photodiode, an I/V conversion circuit, an amplifier circuit, and a filter processing circuit. Temperature controlling unit performs temperature control of the laser light that is emitted from laser diode LD, based on the wavelength characteristics of reflected light received by photodiode PD for temperature control. In this manner, invisible light sensor NVSS can reduce a processing load of received light processor SA. In addition, the temperature control may be performed by another method.

In the fourth embodiment, the infrared light is used as the invisible light; however, ultraviolet light may be used depending on the absorption spectra of the detection target substance. In this manner, detection camera 1 can increase a range in which a substance can be detected.

In the fourth embodiment, a processor or a controller may be configured to be physically present. In addition, when a programmable processor or controller is used, it is possible to change process content by changing a program, and thus it is possible to increase flexibility of design of the processor or the controller. The processor or the controller may be configured of one semiconductor chip or may be physically configured of a plurality of semiconductor chips. In a case where the processor or the controller is configured of the plurality of semiconductor chips, various types of control of the fourth embodiment may be realized by respectively different semiconductor chips. In this case, it is possible to consider that one processor or controller is configured of the plurality of semiconductor chips. In addition, the processor or controller may be configured of the semiconductor chip and members (condenser or the like) having other functions. In addition, one semiconductor chip may be configured to realize the function of the processor or the controller and functions other than the functions thereof.

Fifth Embodiment

First, before the fifth embodiment is described in detail, background to the content of the detection camera as an example of the substance detecting device of the fifth embodiment is described with reference to FIGS. 54A and 54B. Hereinafter, gas is described as the target substance detected by the detection camera of the fifth embodiment; however, the detection target substance is not limited to the gas.

Figure 54A:
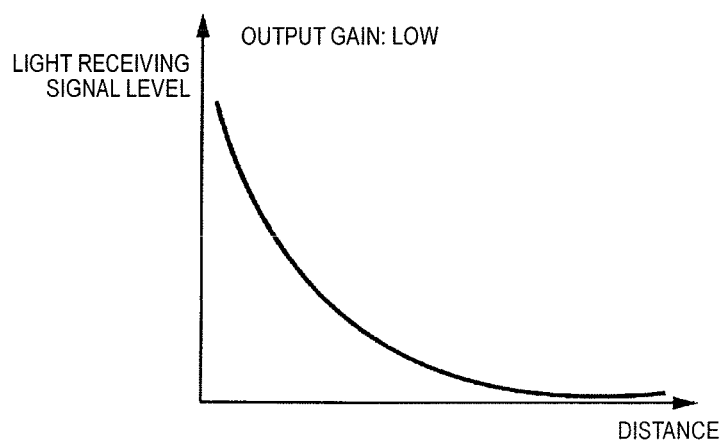
FIG. 54A is a graph illustrating an example of a relationship between a distance to detection target gas and a signal level of reflected light obtained by reflection from the gas in a case where output gain of detection light for gas detection is low in the substance detecting device that performs gas detection with one arbitrary position in measurement environment as a target.

FIG. 54A is a graph illustrating an example of a relationship between a distance to the detection target gas and a signal level of reflected light reflected from the gas in a case where output gain of detection light for detecting a gas is low in the substance detecting device that performs gas detection with one arbitrary position in measurement environment as a target. FIG. 54B is a graph illustrating an example of a relationship between a distance to the detection target gas and the signal level of the reflected light reflected from the gas in a case where the output gain of detection light for detecting the gas is high in the substance detecting device that performs gas detection with one arbitrary position in measurement environment as a target. In FIGS. 54A and 54B, the signal of the reflected light is a light receiving signal obtained by receiving light in the substance detecting device that performs gas detection with an arbitrary position in a measurement environment as a target.

The substance detecting device that performs the gas detection with an arbitrary position in the measurement environment as a target does not perform the gas detection with an arbitrary two-dimensional area (that is, a spatial area) in the measurement environment as a target from the substance detecting device that is a start point.

In addition, as illustrated in FIG. 54A, in a case where the output gain of the laser light for substance detection (that is, a light emitting intensity of the laser light that is emitted from the substance detecting device) is low, and the substance detecting device receives the reflected light reflected from gas present at a position at a short distance from the substance detecting device, it is possible to detect the gas because the level of the light receiving signal is high. However, in a case where the substance detecting device receives the reflected light reflected from the gas present at a position at a long distance from the substance detecting device, it is difficult to detect the gas because the level of the light receiving signal is low.

Figure 54B:
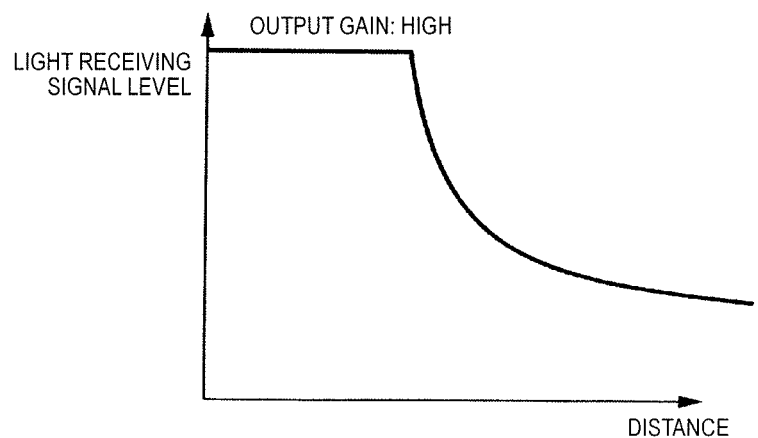
FIG. 54B is a graph illustrating an example of a relationship between a distance to the detection target gas and the signal level of the reflected light obtained by reflection from the gas in a case where the output gain of detection light for gas detection is high in the substance detecting device that performs gas detection with one arbitrary position in measurement environment as a target.

On the other hand, as illustrated in FIG. 54B, in a case where the output gain of the laser light for substance detection (that is, a light emitting intensity of the laser light that is emitted from the substance detecting device) is high, and the substance detecting device receives the reflected light reflected from gas present at a position at a long distance from the substance detecting device, it is possible to detect the gas because the level of the light receiving signal is high. However, in a case where the substance detecting device receives the reflected light reflected from the gas present at a position at a short distance from the substance detecting device, it is difficult to detect the gas because the level of the light receiving signal is too high and is saturated. Therefore, a distance range in which it is possible to detect a substance such as gas is limited to a predetermined distance range (for example, 5 m to 10 m) from the substance detecting device.

In the fifth embodiment, a distance to the gas as an example of the detection target substance is measured, and the output gain of the laser light for gas detection is changeable depending on the obtained distance. In this manner, the detection camera as an example of the substance detecting device in which it is not necessary to regulate a distance range, in which it is possible to detect the gas, and an example of a gas detecting system including the detection camera are described.

Hereinafter, embodiments of the detection camera, the gas detecting system, and a gas detecting method of the fifth embodiment will be described in detail with reference to proper figures. However, the detailed description that is more than necessary is omitted in some cases. For example, the detailed description of a well-known subject or repetitive description of substantially the same configuration is omitted in some cases, in order to avoid unnecessary and redundant description and in order for those skilled in the art to achieve easy understanding. The accompanying figures and the following description are provided to make those skilled in the art sufficiently understand this disclosure and are not provided to limit subjects according to claims.

Figure 40:
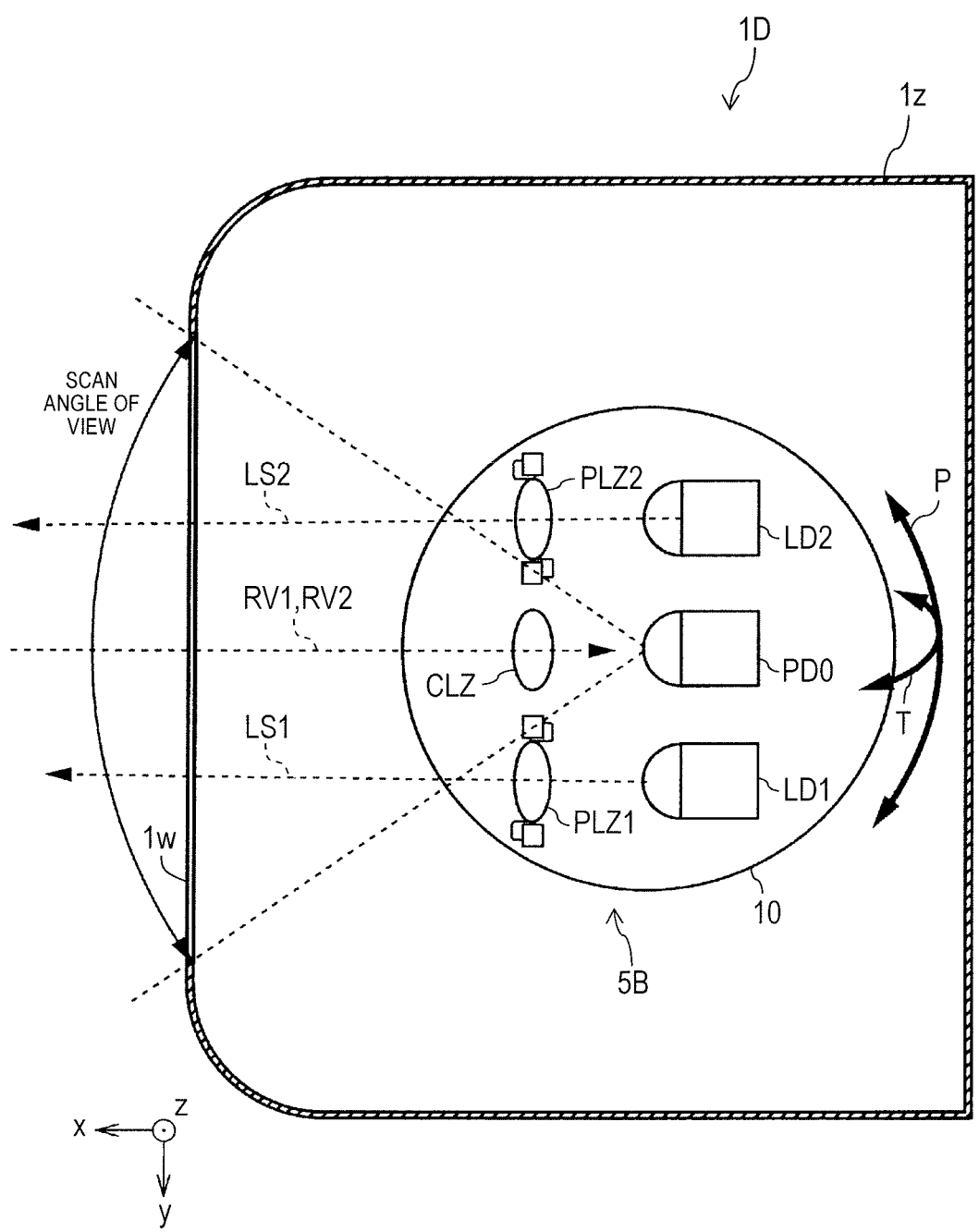
FIG. 40 is a diagram illustrating an example of an internal configuration of the sensor scanning unit of the fifth embodiment.

A schematic diagram illustrating an outline of detection camera 1D including invisible light sensor NVSS in the fifth embodiment is the same as FIG. 1 in the first to third embodiments, and thus the detailed description thereof is omitted. Detection camera 1D illustrated in FIG. 40 is configured to include visible light camera illustrated in FIG. 1 VSC and invisible light sensor NVSS.

Figure 37:
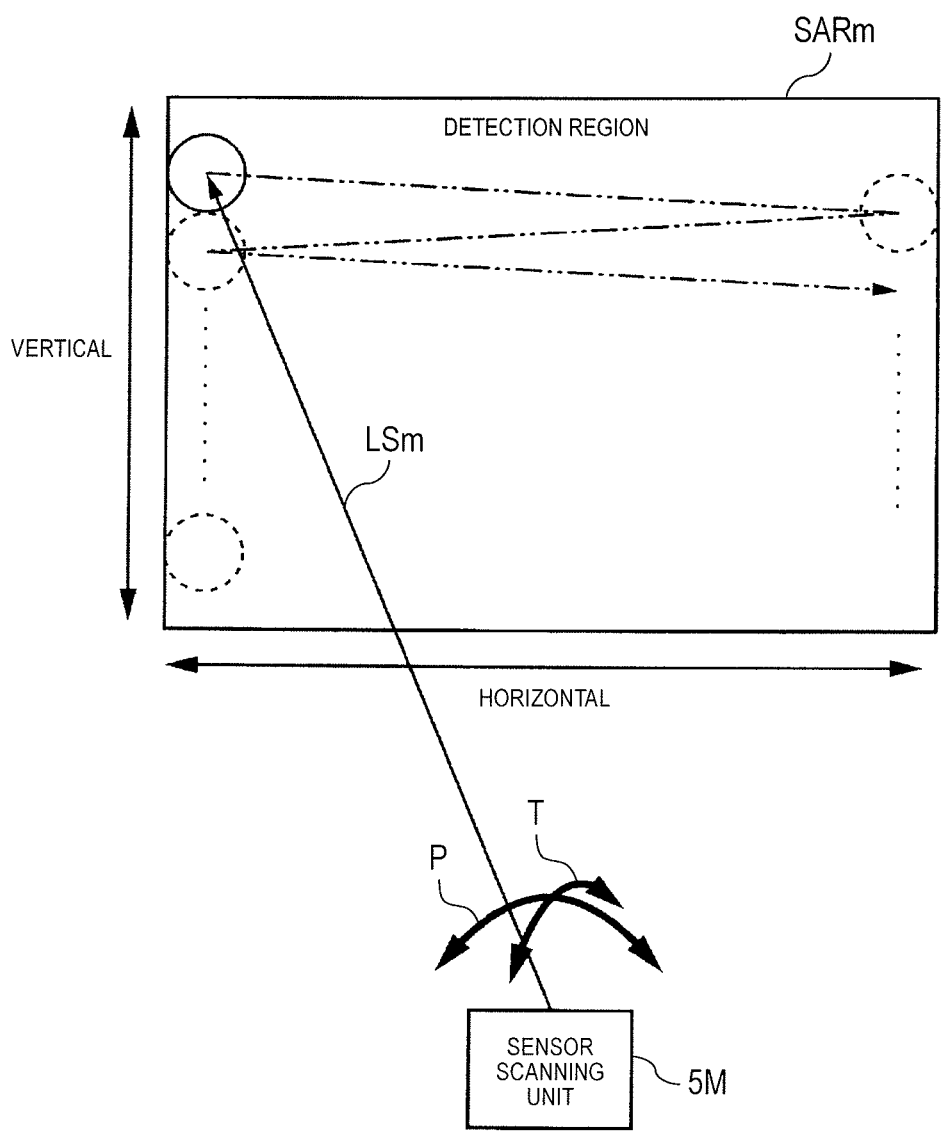
FIG. 37 is a diagram illustrating an example of scanning a detection region by a sensor scanning unit in a comparative example.

FIG. 37 is a diagram illustrating an example of scanning of detection region SARm by sensor scanning unit 5M in a comparative example. Sensor scanning unit 5M of the comparative example drives and causes camera platform 10 to swivel in pan direction P and tilt direction T so as to achieve a scan angle of view that covers entire detection region SARm from sensor scanning unit 5M as a start point, and thereby laser light LSm emitted from the laser diode for gas detection which is mounted on the camera platform is emitted while scanning in a zigzag manner. In this manner, sensor scanning unit 5M is capable of irradiating entire detection region SARm with laser light LSm.

Figure 38:
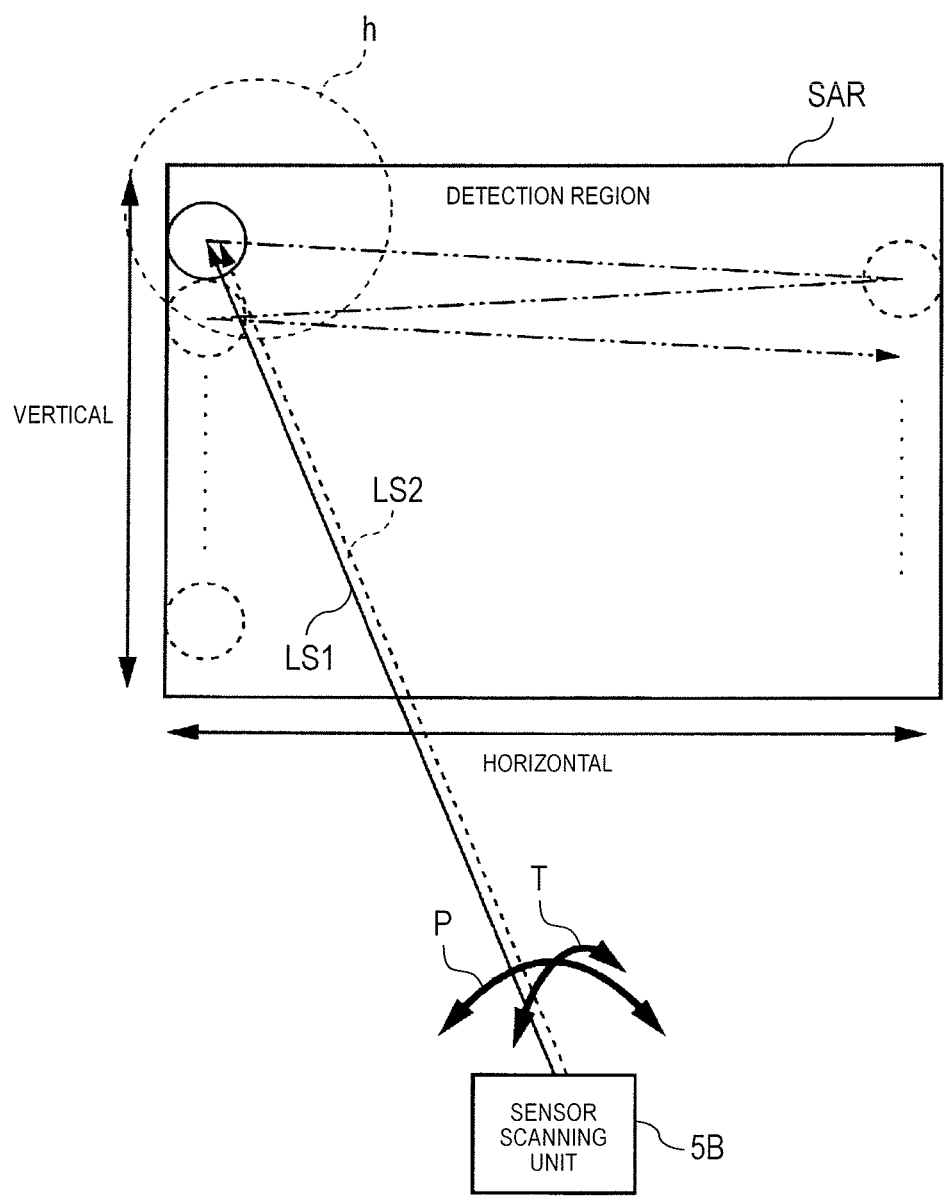
FIG. 38 is a diagram illustrating an example of scanning of a detection region by a sensor scanning unit in a fifth embodiment.

FIG. 38 is a diagram illustrating an example of the scanning of detection region SAR by sensor scanning unit 5B in the fifth embodiment. Sensor scanning unit 5B of the fifth embodiment drives and causes camera platform 10 to swivel in pan direction P and tilt direction T so as to achieve a scan angle of view that covers entire detection region SAR from sensor scanning unit 5B as a start point, and thereby laser light LS1 from laser diode LD1 for gas detection and laser light LS2 from laser diode LD2 for distance measurement which are mounted on camera platform 10 are emitted while scanning in the zigzag manner. In addition, in the scanning of the fifth embodiment, before the irradiation position is irradiated with laser light LS1 for gas detection, laser light LS2 for distance measurement is emitted to the same irradiation position.

Figure 39:
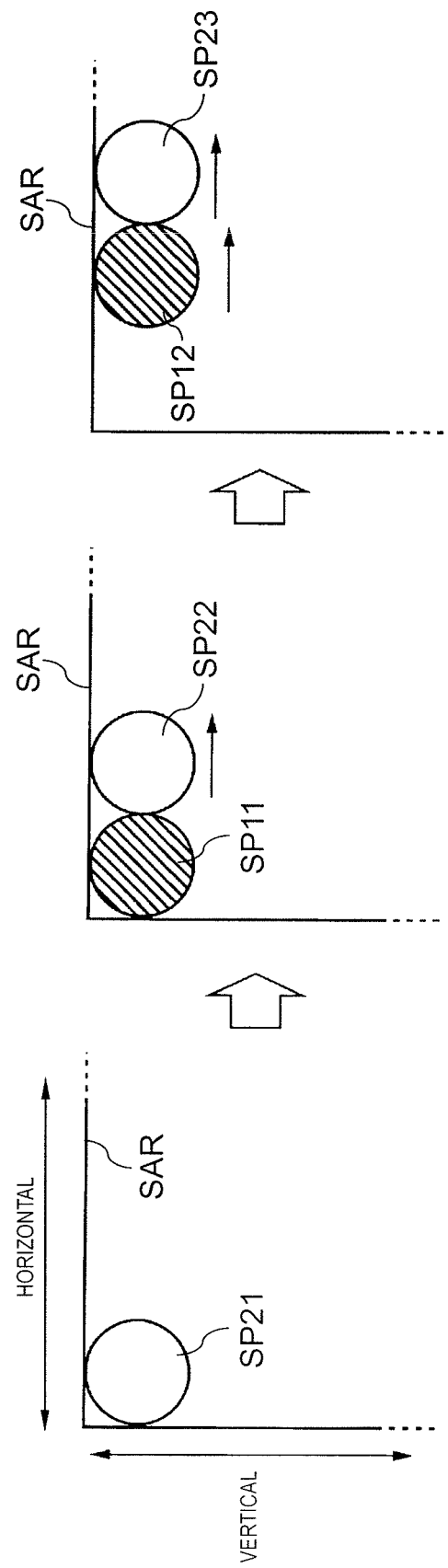
FIG. 39 is a diagram illustrating irradiation positions of laser light for gas detection and laser light for distance measurement in a time series in a region surrounded by a dotted frame h in FIG. 38.

FIG. 39 is a diagram illustrating irradiation positions of laser light LS1 for gas detection and laser light LS2 for distance measurement in a time series in a region surrounded by a dotted frame h in FIG. 38. In FIG. 39, laser light LS1 and LS2 is irradiated toward a right direction on the page in the same figure (a "−y direction" in FIG. 1). Irradiation with laser light LS1 and LS2 is simultaneously performed in a spot manner such that the irradiation positions are adjacent except for the first irradiation position (that is, an irradiation position illustrated on the leftmost side in FIG. 39). Hereinafter, an operation of irradiating the irradiation positions having a finite area with the same predetermined diameter with laser light LS1 and LS2 in a spot manner by detection camera 1D is abbreviated to "spot irradiation". Therefore, emission of laser light LS1 and LS2 moves in a zigzag shape and detection region SAR is two-dimensionally scanned such that the respective irradiation positions of laser light LS1 and LS2 travels forward and backward in the horizontal direction and moves in the vertical direction.

In the first spot irradiation (that is, the leftmost side) illustrated in FIG. 39, irradiation position SP21 is irradiated with laser light LS2 for distance measurement.

In the continual (that is, central) spot irradiation, irradiation position SP22 is irradiated with laser light LS2 for distance measurement, irradiation position SP22 reached by moving to the right side by a length of one irradiation position from irradiation position SP21 irradiated in the first spot irradiation. At this time, irradiation with laser light LS1 for gas detection is performed on the same irradiation position SP11 as irradiation position SP21 irradiated with laser light LS2 for distance measurement in the first spot irradiation.

Similarly, in the continual (that is, right-most side) spot irradiation, the irradiation position with laser light LS2 for distance measurement, irradiation position SP22 and the irradiation position with laser light LS1 for gas detection move to the right side by a length of one irradiation position. In other words, irradiation position SP23 is irradiated with laser light LS2 for distance measurement by moving to the right side by a length of one irradiation position from irradiation position SP22 irradiated in the previous spot irradiation. At this time, irradiation with laser light LS1 for gas detection is performed on the same irradiation position SP12 as irradiation position SP22 irradiated with laser light LS2 for distance measurement in the previous spot irradiation. Hereinafter, similarly, spot irradiation with laser light LS1 and LS2 is repeated.

As described above, in detection camera 1D of the fifth embodiment, the irradiation position irradiated with laser light LS2 for distance measurement is ahead of the irradiation position irradiated with laser light LS1 for gas detection by a length of one irradiation position. In this manner, detection camera 1D can measure a distance to the irradiation position in the spot irradiation with laser light LS1 for gas detection is performed to the same irradiation position as the irradiation position irradiated with laser light LS2 for distance measurement, based on reflected light RV2 of laser light LS2 reflected from the irradiation position. Hence, detection camera 1D can set the output gain of laser light LS1 for gas detection depending on the distance obtained from the measurement and can perform irradiation with laser light LS1 having appropriate emission intensity so as to determine the detection of the presence or absence of gas with high accuracy.

FIG. 40 is a diagram illustrating an example of an internal configuration of sensor scanning unit 5B of the fifth embodiment. FIG. 40 illustrates the internal configuration related to sensor scanning unit 5B in detection camera 1D when viewed from above in FIG. 1 (that is, in the −z-axis direction).

For example, detection camera 1D includes box-shaped housing 1z. Opening 1w for invisible light sensor NVSS is formed in a side surface of housing 1z (that is, x-axis direction). Transparent glass or resin may be fit in opening 1w for water proof and dust proof. In addition, condenser V31 of visible light camera VSC is exposed from the side surface of housing 1z.

Sensor scanning unit 5B is provided to be supported in housing 1z. Sensor scanning unit 5B has camera platform 10, which freely swivels in pan direction P (direction parallel to the xy plane in the figure) and in tilt direction T (z-axis direction in the figure), and pan/tilt unit 15 including a motor mechanism that drives camera platform 10.

On camera platform 10 as an example of a base, two laser diodes (that is, laser diode LD1 for gas detection and laser diode LD2 for distance measurement), two collimator lenses PLZ1 and PLZ2, photodiode PD, and condenser CLZ are mounted. On camera platform 10, laser diode LD2 for distance measurement is disposed on the upper side in the figure (a minus direction of a y axis) from laser diode LD1 for gas detection. Pan/tilt unit 15 causes camera platform 10 to swivel in pan direction P and tilt direction T, thereby making it possible to perform two-dimensional scanning (horizontal scanning and vertical scanning) in detection region SAR with emission of laser light LS1 and LS2 that is emitted from laser diode LD1 for gas detection and laser diode LD2 for distance measurement, respectively.

Laser light LS1 emitted from laser diode LD1 for gas detection is transmitted through collimator lens PLZ1 so as to be parallel light and is emitted toward detection space K. Reflected light RV1 of laser light LS1 reflected from gas GS in detection space K is incident through opening 1w formed in housing 1z of detection camera 1D, is condensed by condenser CLZ, and is received by photodiode PD0.

The presence or absence of gas GS which is present in detection space K is determined from absorption spectra as an example of absorption characteristics of reflected light RV1 received by photodiode PD0. For example, detection region SAR that is a range in which it is possible to perform scanning in detection space K with laser light LS1 emitted from laser diode LD1 for gas detection is set depending on the shape of opening 1w formed in housing 1z.

Laser light LS2 emitted from laser diode LD2 for distance measurement is transmitted through collimator lens PLZ2 so as to be parallel light and is emitted toward detection space K. Similar to the case of reflected light RV1 of laser light LS1, reflected light RV2 of laser light LS2 reflected from gas GS in detection space K is incident through opening 1w formed in housing 1z of detection camera 1D, is condensed by condenser CLZ, and is received by photodiode PD0.

Figure 41:
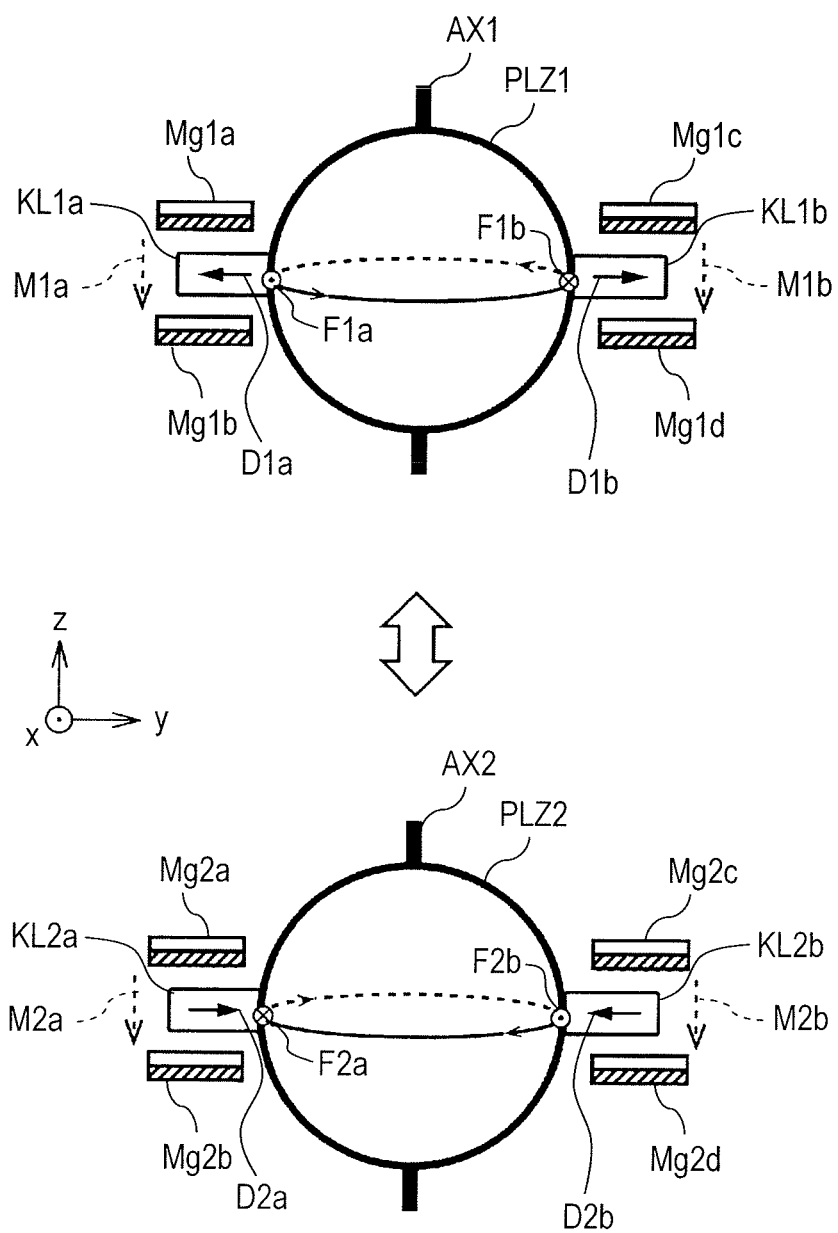
FIG. 41 is a diagram illustrating an example of driving of a collimator lens that is provided in the sensor scanning unit of the fifth embodiment.

FIG. 41 is a diagram illustrating an example of driving of collimator lenses PLZ1 and PLZ2 that are provided in sensor scanning unit 5B of the fifth embodiment. FIG. 42 is a diagram illustrating an example of driving of collimator lenses PLZ1 and PLZ2 when viewed from above (in the −z direction) in FIG. 41. Collimator lenses PLZ1 and PLZ2 are disposed to be freely swivel around lens rotation shaft AX1 (parallel to the z-axis direction) on camera platform 10. Mechanisms of drivers of collimator lenses PLZ1 and PLZ2 are substantially the same.

A pair of coils KL1a and KL1b is attached to collimator lens PLZ1 on both sides in the y-axis direction. In addition, a pair of magnets Mg1a and Mg1b is disposed to be opposite to each other on camera platform 10 so as to sandwich coil KL1a therebetween in the z-axis direction. Similarly, a pair of magnets Mg1c and Mg1d is disposed to be opposite to each other on camera platform 10 so as to sandwich coil KL1b in the z-axis direction therebetween. In addition, as illustrated in FIG. 42, the pair of magnets Mg1a and Mg1b is disposed to cover a current path of coil KL1a in the y direction on the lower side in the figure (that is, not to cover current in the y direction on the upper side in the figure). Similarly, as illustrated in FIG. 42, the pair of magnets Mg1c and Mg1d is disposed to cover a current path of coil KL1b in the y direction on the upper side in the figure (that is, not to cover current in the y direction on the lower side in the figure).

When the pair of magnets Mg1a and Mg1b is disposed such that a side of magnet Mg1a which is opposite to magnet Mg1b is set as a N pole, and a side of magnet Mg1b which is opposite to magnet Mg1a is set as a S pole, magnetic field lines M1a acting in the −z-axis direction are generated between the pair of magnets Mg1a and Mg1b. Similarly, when the pair of magnets Mg1c and Mg1d is disposed such that a side of magnet Mg1c which is opposite to magnet Mg1d is set as a N pole, and a side of magnet Mg1d which is opposite to magnet Mg1c is set as a S pole, magnetic field lines M1b acting in the −z-axis direction are generated between the pair of magnets Mg1c and Mg1d.

When a current flows through coil KL1a in a direction (rightward direction with respect to the −z axis) represented by arrow D1a, force F1a due to electromagnetic induction in accordance with Fleming's law acts on a portion of coil KL1a sandwiched by the pair of magnets Mg1a and Mg1b. Force F1a is a force (rotating force) that causes collimator lens PLZ1 to rotate around lens rotation shaft AX1 (z axis) counterclockwise in FIG. 42. Similarly, when a current flows through coil KL1b in a direction (rightward direction with respect to the −z axis) represented by arrow D1b, force F1b due to electromagnetic induction in accordance with Fleming's law acts on a portion of coil KL1b sandwiched by the pair of magnets Mg1c and Mg1d. Similar to force F1a, force F1b is a force (rotating force) that causes collimator lens PLZ1 to rotate around lens rotation shaft AX1 (z axis) counterclockwise in FIG. 42. Forces F1a and F1b are proportional to an amount of the current supplied to coils KL1a and KL1b, respectively, from two-dimensionalization unit controller 112 to be described below.

In addition, a spring member that biases collimator lens PLZ1, which freely swivels around lens rotation shaft AX1, back to an initial position is attached to collimator lens PLZ1. Hence, two-dimensionalization unit controller 112 supplies the current to coils KL1a and KL1b such that the rotating force of collimator lens PLZ1 cancels the bias force of the spring member. In this manner, it is possible to stop collimator lens PLZ1 at any rotation angle. In other words, collimator lens PLZ1 can tilt with respect to an optical axis by a predetermined angle. The maximum tilt angle of collimator lens PLZ1 is a limit angle at which coil KL1a is not sandwiched between the pair of magnets Mg1a and Mg1b (coil KL1b between the pair of magnets Mg1c and Mg1d). Collimator lens PLZ2 is similarly described by using reference marks corresponding to collimator lens PLZ1.

A pair of coils KL2a and KL2b is attached to collimator lens PLZ2 on both sides in the y-axis direction. In addition, a pair of magnets Mg2a and Mg2b is disposed to be opposite to each other on camera platform 10 so as to sandwich coil KL2a therebetween in the z-axis direction. Similarly, a pair of magnets Mg2c and Mg2d is disposed to be opposite to each other on camera platform 10 so as to sandwich coil KL2b in the z-axis direction therebetween. In addition, as illustrated in FIG. 42, the pair of magnets Mg2a and Mg2b is disposed to cover a current path of coil KL2a in the y direction on the lower side in the figure (that is, not to cover current in the y direction on the upper side in the figure). Similarly, as illustrated in FIG. 42, the pair of magnets Mg2c and Mg2d is disposed to cover a current path of coil KL2b in the y direction on the upper side in the figure (that is, not to cover current in the y direction on the lower side in the figure).

When the pair of magnets Mg2a and Mg2b is disposed such that a side of magnet Mg2a which is opposite to magnet Mg2b is set as a N pole, and a side of magnet Mg2b which is opposite to magnet Mg2a is set as a S pole, magnetic field lines M2a acting in the −z-axis direction are generated between the pair of magnets Mg2a and Mg2b. Similarly, when the pair of magnets Mg2c and Mg2d is disposed such that a side of magnet Mg2c which is opposite to magnet Mg2d is set as a N pole, and a side of magnet Mg2d which is opposite to magnet Mg2c is set as a S pole, magnetic field lines M2b acting in the −z-axis direction are generated between the pair of magnets Mg2c and Mg2d.

When a current flows through coil KL2a in a direction (rightward direction with respect to the −z axis) represented by arrow D2a, force F2a due to electromagnetic induction in accordance with Fleming's law acts on a portion of coil KL2a sandwiched by the pair of magnets Mg2a and Mg2b. Force F2a is a force (rotating force) that causes collimator lens PLZ2 to rotate around lens rotation shaft AX2 (z axis) clockwise in FIG. 42. Similarly, when a current flows through coil KL2b in a direction (rightward direction with respect to the −z axis) represented by arrow D2b, force F2b due to electromagnetic induction in accordance with Fleming's law acts on a portion of coil KL2b sandwiched by the pair of magnets Mg2c and Mg2d. Similar to force F2a, force F2b is a force (rotating force) that causes collimator lens PLZ2 to rotate around lens rotation shaft AX2 (z axis)

clockwise in FIG. 42. Forces F2a and F2b are proportional to an amount of the current supplied to coils KL2a and KL2b, respectively, from two-dimensionalization unit controller 112 to be described below.

In addition, a spring member that biases collimator lens PLZ2, which freely swivels around lens rotation shaft AX2, back to an initial position is attached to collimator lens PLZ2. Hence, two-dimensionalization unit controller 112 supplies the current to coils KL2a and KL2b such that the rotating force of collimator lens PLZ2 cancels the bias force of the spring member. In this manner, it is possible to stop collimator lens PLZ2 at any rotation angle. In other words, collimator lens PLZ2 can tilt with respect to an optical axis by a predetermined angle. The maximum tilt angle of collimator lens PLZ2 is a limit angle at which coil KL2a is not sandwiched between the pair of magnets Mg2a and Mg2b (coil KL2b between the pair of magnets Mg2c and Mg2d).

As described above, two-dimensionalization unit controller 112 drives collimator lenses PLZ1 and PLZ2 to rotate at a predetermined rotation angle and to tilt with respect to the optical axis, thereby adjusting an angle of laser light LS1 and LS2 in the pan direction which is emitted from the laser diodes LD1 and LD2, respectively. In this manner, two-dimensionalization unit controller 112 can shift, by a length of one irradiation position, the irradiation position, on which the spot irradiation is performed with laser light LS1 that is transmitted through collimator lens PLZ1, and the irradiation position, on which the spot irradiation is performed with laser light LS2 that is transmitted through collimator lens PLZ2. In the fifth embodiment, both of collimator lenses PLZ1 and PLZ2 have respective rotatable drivers; however, one collimator lens may be fixed and only the other collimator lens may have the driver.

Figure 43:
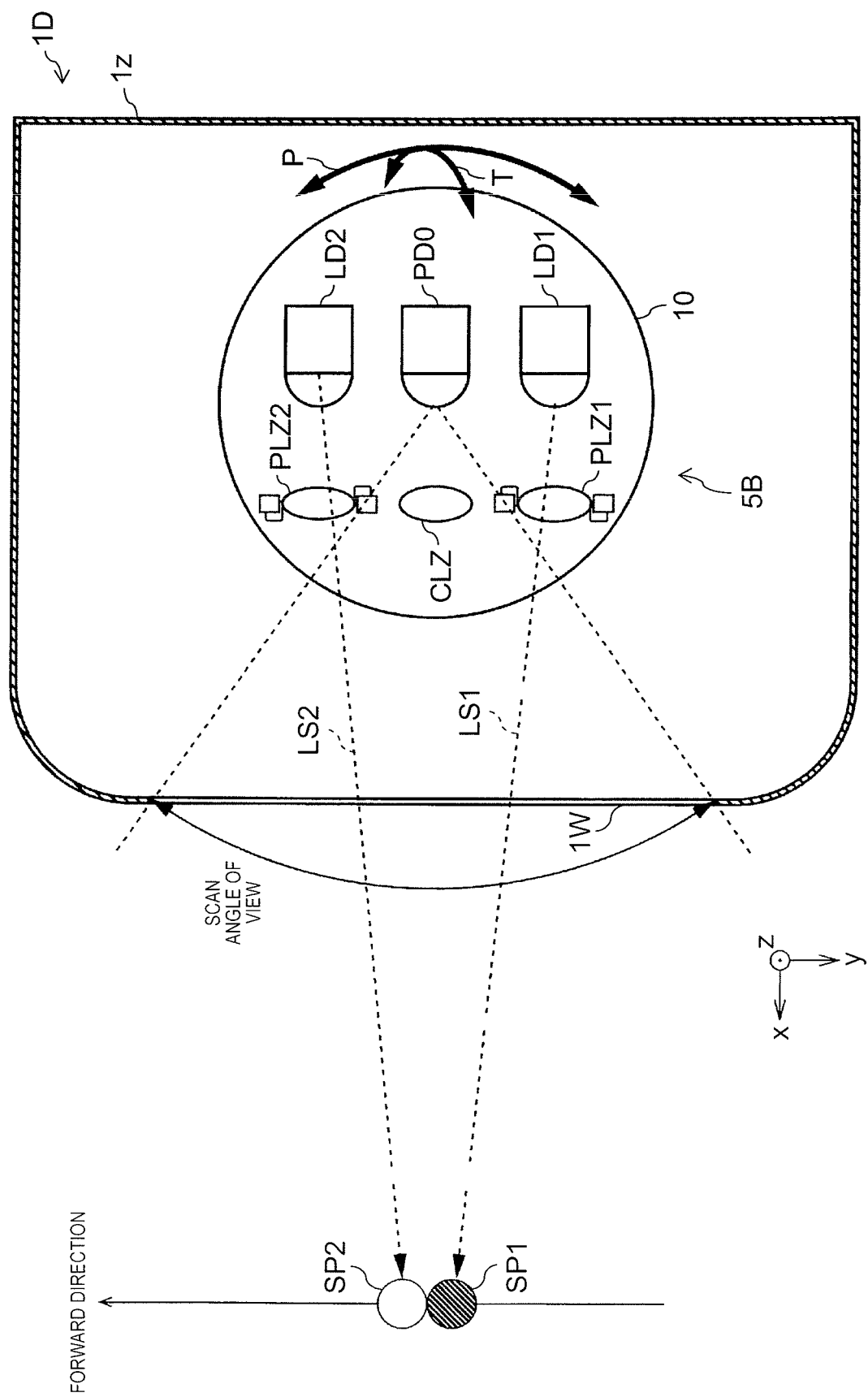
FIG. 43 is a diagram illustrating an example of a swivel operation of the sensor scanning unit and irradiation positions of the laser light for distance measurement and the laser light for gas detection in a case of one line is scanned in a forward direction (−y direction) in the fifth embodiment.

FIG. 43 is a diagram illustrating an example of a swivel operation of sensor scanning unit 5B and the irradiation positions of laser light LS2 for distance measurement and laser light LS1 for gas detection in a case of one line is scanned in a forward direction (−y direction) in the fifth embodiment. Here, when viewed from above in the −z-axis direction to look at the paper of FIG. 43, a direction in which camera platform 10 rotates clockwise is set as a plus (+) direction, and a direction in which camera platform 10 rotates counterclockwise is set as a minus (−) direction.

Laser diode LD2 for distance measurement is disposed on the upper side in the figure (−y-axis direction) from laser diode LD1 for gas detection on camera platform 10. Therefore, in a case where scanning with laser light LS1 for gas detection and laser light LS2 for distance measurement is performed in the forward direction, irradiation position SP2 of laser light LS2 for distance measurement is ahead of irradiation position SP1 of laser light LS1 for gas detection by a length of one irradiation position, even when laser light does not intersect (cross) with each other.

In this case, in order to accurately match irradiation position SP1 irradiated later with laser light LS1 for gas detection with irradiation position SP2 irradiated first with laser light LS2 for distance measurement, at least one of collimator lens PLZ1 for gas detection and collimator lens PLZ2 for distance measurement may be adjusted to tilt.

Figure 44:
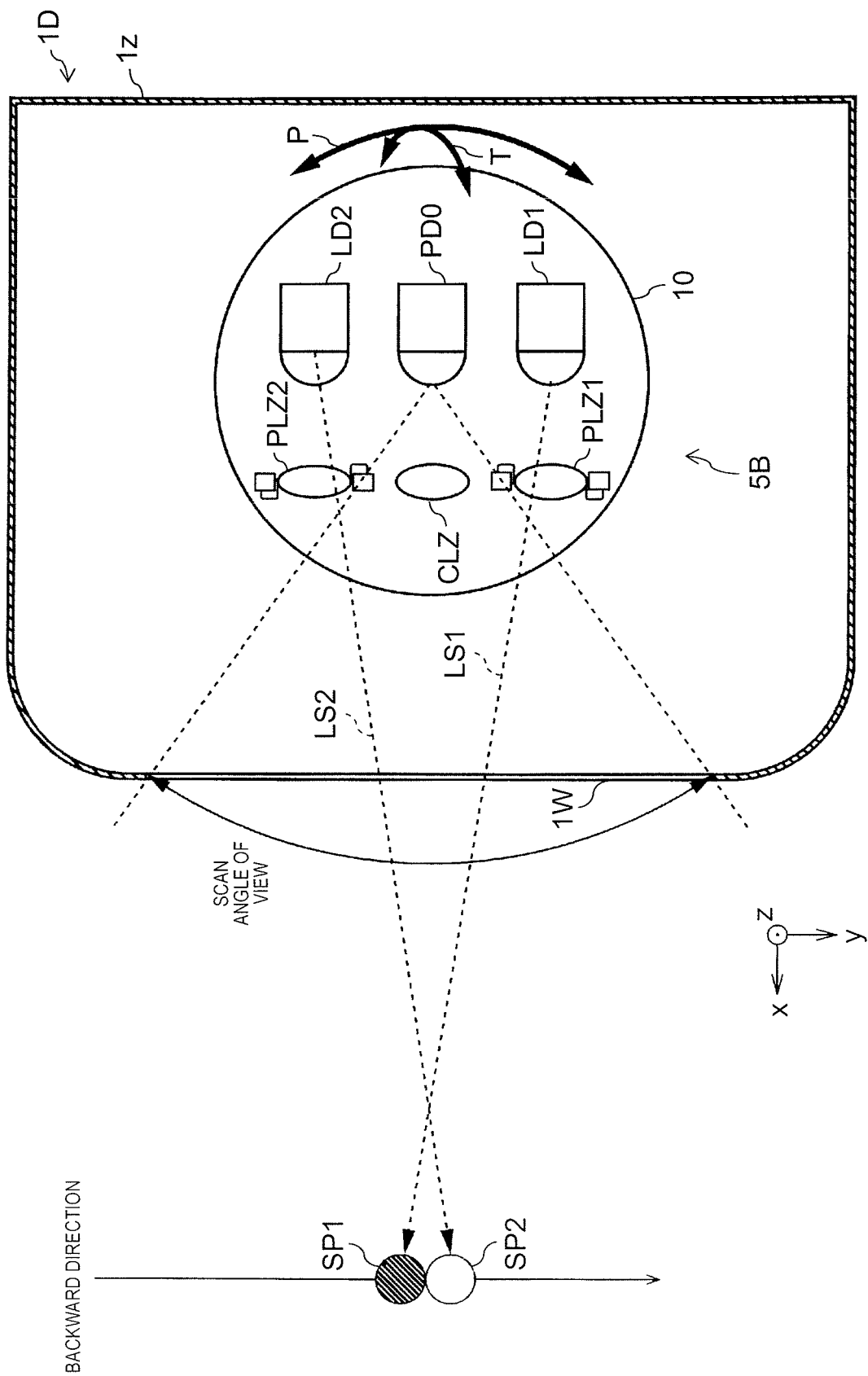
FIG. 44 is a diagram illustrating an example of a swivel operation of the sensor scanning unit and irradiation positions of the laser light for distance measurement and laser light for gas detection in a case of one line scanning in a backward direction (+y direction) in the fifth embodiment.

FIG. 44 is a diagram illustrating an example of a swivel operation of sensor scanning unit 5B and irradiation positions of laser light LS2 for distance measurement and laser light LS1 for gas detection in a case of one line is scanned in a backward direction (+y direction) in the fifth embodiment. Laser diode LD2 for distance measurement is disposed on the upper side in the figure (−y-axis direction) from laser diode LD1 for gas detection on camera platform 10. Therefore, in a case where scanning with laser light LS1 for gas detection and laser light LS2 for distance measurement is performed in the backward direction, laser light does not need to intersect (cross) with each other. Thus, at least one of Collimator lens PLZ1 and collimator lens PLZ2 significantly tilts, and irradiation position SP2 of laser light LS2 for distance measurement is ahead of irradiation position SP1 of laser light LS1 for gas detection by a length of one irradiation position. At this time, in order to accurately match irradiation position SP1 irradiated later with laser light LS1 for gas detection with irradiation position SP2 irradiated first with laser light LS2 for distance measurement, the adjustment may be performed simultaneously.

In the fifth embodiment, a case where line scanning is performed with laser light LS2 for distance measurement and laser light LS1 for gas detection in the forward/backward direction is described; however, in a case where line scanning is performed in one direction (only frontward direction) as the scanning direction, laser light LS1 and LS2 may intersect (cross) to each other or may be parallel to each other. In this case, at a stage in which both of laser light LS1 and LS2 for distance measurement and gas detection reach an end point in one direction, sensor scanning unit 5B may stop emission of laser light LS1 and LS2 so as to cause laser light to rapidly move to a start point of the next line and may again start emission of laser light so as to scan the next line. The laser light may move to a start point of the next line while laser light is emitted without stopping/restarting of the laser light.

FIG. 45 is a block diagram illustrating an example of an internal configuration of detection camera 1D in the fifth embodiment in detail. As described above, detection camera 1D is configured to include invisible light sensor NVSS and visible light camera VSC. Invisible light sensor NVSS is configured to include controller 11B, projector PJ, and received light processor SA. For simplification of figures, in FIG. 45, laser diode LD1 for gas detection and laser diode LD2 for distance measurement are abbreviated to "for gas detection LD" and "for distance measurement LD", respectively, and the abbreviated terms are different from reference mark "LD" of "LD1" and "LD2".

Controller 11B is configured by using a central processing unit (CPU), a micro processing unit (MPU), or a digital signal processor (DSP). For example, controller 11 performs signal processing for overall control of operation control of the members of invisible light sensor NVSS, input/output processing of data with the other members, arithmetic processing of data, and storage processing of data.

Controller 11B includes two-dimensionalization unit controller 112, modulation signal generator 113, and signal gain adjustor 114. Two-dimensionalization unit controller 112 outputs, to pan/tilt unit 15, pan/tilt driving signal for driving sensor scanning unit 5B in pan direction P and tilt direction T. Pan/tilt unit 15 causes camera platform 10 to swivel in the pan direction and tilt direction in response to the pan/tilt driving signal.

In addition, as described with reference to FIGS. 41 and 42, two-dimensionalization unit controller 112 supplies the current to coils by controlling an amount of current supply to coils KL1a, KL1b, KL2a, and KL2b in sensor scanning unit 5B such that the irradiation position, on which the spot irradiation is performed with laser light LS1 that is transmitted through collimator lens PLZ1, and the irradiation position, on which the spot irradiation is performed with laser light LS2 that is transmitted through collimator lens PLZ2 are shifted by a length of one irradiation position.

Modulation signal generator 113 generates a modulation signal for performing wavelength modulation on laser light LS1 that is emitted from laser diode LD1 for gas detection and outputs the modulation signal as the light source light-emitting signal to laser diode LD1 for gas detection and laser diode LD2 for distance measurement. Laser diode LD1 for gas detection and laser diode LD2 for distance measurement emit wavelength-modulated laser light LS1 and LS2, respectively, in response to the light source light-emitting signal. Modulation signal generator 113 may output a signal for emitting laser light LS2 having constant amplitude on which the wavelength modulation is not performed, as the light source light-emitting signal that is input to laser diode LD2 for distance measurement. In this case, laser diode LD2 for distance measurement emits laser light LS2 having constant amplitude in response to the light source light-emitting signal from modulation signal generator 113.

The wavelength modulation can be performed by using various methods. In the fifth embodiment, drive current of laser diode LD1 for gas detection and laser diode LD2 for distance measurement is changed, and thereby the wavelength modulation is performed. The drive current is an input signal to the laser diodes, and the frequency of the drive current is the frequency of the wavelength modulation. A temperature is swept (changed) in predetermined amplitude to a target temperature at which laser diodes are stabilized, and thereby the wavelength modulation can be performed. In this case, Peltier element Pt provided in a laser diode absorbs or emits heat in response to a signal from controller 11B and changes the temperature of the laser diode, thereby making it possible to change the wavelength of laser light.

In addition, it is desirable that output gain of laser diode LD2 for distance measurement is set to be high such that laser light LS2 reaches an irradiation position deep in detection region SAR. In addition, modulation signal generator 113 sets, to detection processor 27B, detection threshold M for detecting the specific substance as the detection target of invisible light sensor NVSS.

Signal gain adjustor 114 as an example of a gain adjustor includes table 14z in which a corresponding relationship between a distance from detection camera 1D and the output gain of laser light LS1 that is emitted from laser diode LD1 for gas detection is registered. Signal gain adjustor 114 calculates, based on table 14z, the output gain corresponding to the distance to the irradiation position in detection region SAR which is calculated by distance calculator 274.

In addition, signal gain adjustor 114 includes memory 14y that temporarily stores calculated output gain. Signal gain adjustor 114 sets output gain stored in memory 14y to laser diode LD1 for gas detection and adjusts, to the optimum value, the output gain of laser light LS1 that is emitted from laser diode LD1 for gas detection.

Figure 47A:
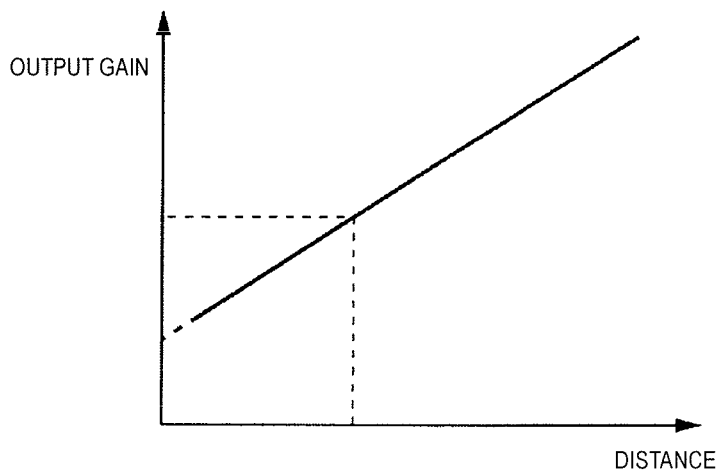
FIG. 47A is a graph illustrating an example of output gain corresponding to a distance registered in a table.
Figure 47B:
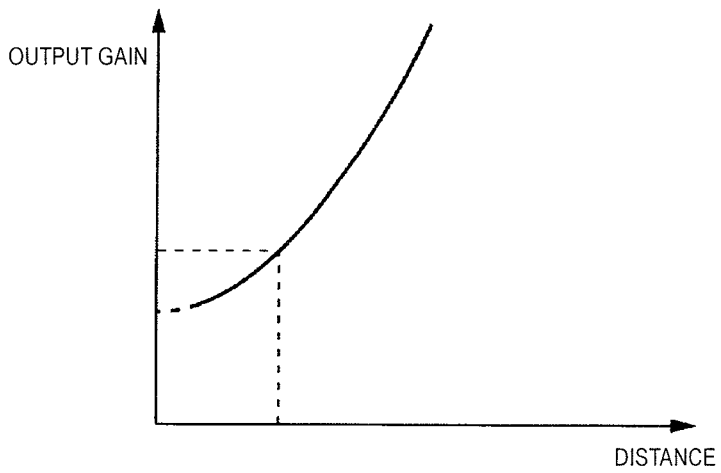
FIG. 47B is a graph illustrating an example of output gain corresponding to a distance registered in a table.

FIGS. 47A and 47B are graphs illustrating an example of the output gain corresponding to a distance registered in table 14z. FIG. 47A illustrates a graph showing a relationship between the distance and the output gain in a linear function. FIG. 47B illustrates a graph showing a relationship between the distance and the output gain in a quadratic function. In both of the graphs in FIGS. 47A and 47B, the longer the distance, the larger value the output gain is set to. The graphs may be set in a function in advance or may be experimentally obtained.

In addition, controller 11B outputs, to AD conversion circuit 271 in detection processor 27B to be described below, a timing signal for instructing execution of AD conversion in AD conversion circuit 271 of detection processor 27B to be described below.

Projector PJ includes laser diode LD1 for gas detection as an example of a first light source, laser diode LD2 for distance measurement as an example of a second light source, projection light source optical portion OP1 for gas detection, projection light source optical portion OP2 for distance measurement, and pan/tilt unit 15. Projection light source optical portion OP1 for gas detection includes collimator lens PLZ1 and the pair of coils KL1a and KL1b. Projection light source optical portion OP2 for distance measurement includes collimator lens PLZ2 and the pair of coils KL2a and KL2b.

Laser diode LD1 for gas detection emits laser light LS1 as an example of wavelength-modulated detection light such that the wavelength of the laser light is included in the absorption wavelength band of gas GS which is the detection target substance. Here, an example of the gas which is the detection target substance includes methane gas (CH4). Similar to laser diode LD1 for gas detection, laser diode LD2 for distance measurement emits laser light LS2 as an example of wavelength-modulated measurement light.

Collimator lenses PLZ1 and PLZ2 changes laser light LS1 and LS2 emitted from laser diodes LD1 and LD2, respectively, into parallel light. As described above, the pair of coils KL1a and KL1b and the pair of coils KL2a and KL2b drive collimator lenses PLZ1 and PLZ2, respectively, such that the collimator lenses tilt with respect to the optical axis at only a predetermined angle.

Pan/tilt unit 15 drives and swivels camera platform 10 in pan direction P and tilt direction T, on which laser diodes LD1 and LD2, projection light source optical portion OP1 for gas detection, projection light source optical portion OP2 for distance measurement, condenser CLZ, and photodiode PD are mounted. In other words, pan/tilt unit 15 causes camera platform 10 to swivel such that the two-dimensional scanning is performed in the scanning range including detection region SAR with laser light LS1 and LS2 that is emitted from laser diode LD1 for gas detection and laser diode LD2 for distance measurement, respectively.

Figure 46:
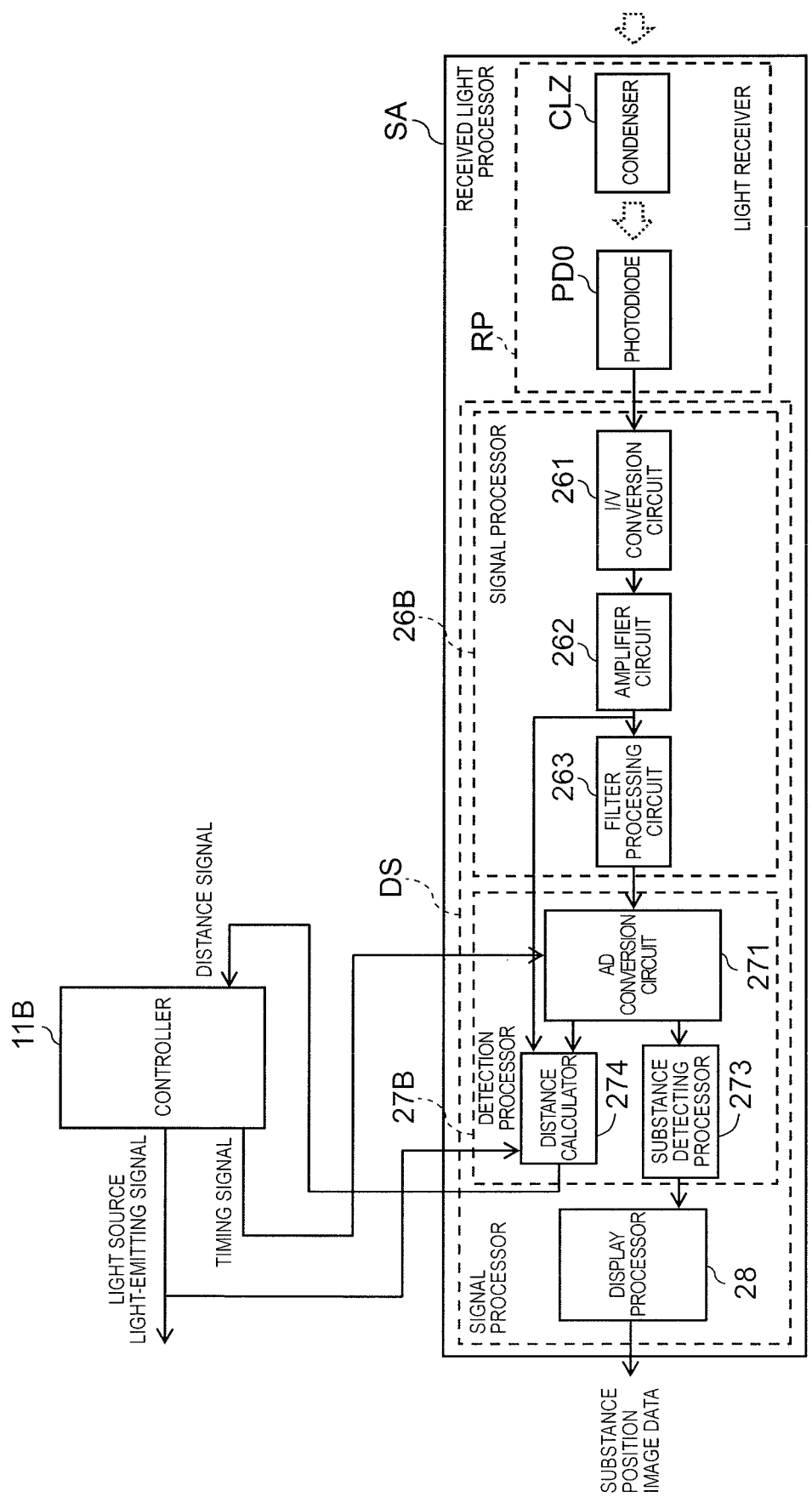
FIG. 46 is a block diagram illustrating an example of an internal configuration of a received light processor illustrated in FIG. 45 in detail.

In addition, received light processor SA is configured to include light receiver RP, which receives reflected light RV1 and RV2 reflected in detection region SAR, and signal processor DS which processes signals of received laser light LS1 and LS2. FIG. 46 is a block diagram illustrating an example of an internal configuration of received light processor SA illustrated in FIG. 45. Light receiver RP includes condenser CLZ and photodiode PD0. Signal processor DS includes signal processing unit 26B, detection processor 27B, and display processor 28.

Signal processing unit 26B includes I/V conversion circuit 261, amplifier circuit 262, and filter processing circuit 263. Detection processor 27B includes AD conversion circuit 271, distance calculator 274, and substance detection processor 273. A processor executes a program stored in the memory, and thereby the functions of distance calculator 274, substance detection processor 273, and display processor 28 are realized.

Condenser CLZ condenses laser light which is emitted from laser diode LD1 for gas detection and laser diode LD2 for distance measurement and is reflected from the specific substance in detection region SAR, and the condensed laser light is received by photodiode PD0. Photodiode PD0 generates electric charges corresponding to the intensity of the received laser light and outputs the electric charges as a current signal.

I/V conversion circuit 261 converts the current signal output from photodiode PD0 into a voltage signal. Amplifier circuit 262 amplifies the voltage signal output from I/V conversion circuit 261. Filter processing circuit 263 performs filter processing on the signal amplified in amplifier circuit 262, and the signal obtained after the filter processing is output as a signal, which is used for the substance detection, to AD conversion circuit 271 in detection processor 27B.

AD conversion circuit 271 in detection processor 27B converts a signal input from signal processing unit 26B into a digital signal, in response to a timing signal output from controller 11B.

A signal that is output from AD conversion circuit 271 is a signal having frequency (2f) twice the signal (frequency 1f of the wavelength-modulated laser light that is emitted from laser diode LD1 for gas detection. The signal having the frequency (frequency 2f) twice frequency 1f is converted into a digital value by AD conversion circuit 271 and, then, is extracted. In other words, in a case where laser light LS1 of frequency 1f is emitted from laser diode LD1 for gas detection, reflected light RV1 reflected from gas GS or reflected from background after the light is transmitted through gas GS is obtained as reflected light of frequency 2f as an output from AD conversion circuit 271.

In addition, in a case where the temperature of laser diode LD1 for gas detection is not changed, and the modulation wavelength width of laser light LS1 that is emitted from laser diode LD1 for gas detection is not shifted from the absorption wavelength band of the specific substance, the signal is the sine wave signal having the constant frequency, which is obtained based on the signal from photodiode PD0.

Distance calculator 274 as an example of a distance measurer calculates a distance from detection camera 1D to the irradiation position based on an output from AD conversion circuit 271 corresponding to reflected light RV2 of laser light LS2 that is emitted from laser diode LD2 for distance measurement, and the signal (distance signal) indicating the calculated distance is output to controller 11B.

FIG. 48 is a timing chart for illustrating an example of a distance detecting method in detection camera 1D of the fifth embodiment. The timing chart shows a change in received light intensity of laser light LS2 for distance measurement and reflected light RV2 with time. Specifically, distance calculator 274 determines an input time of the light source light-emitting signal from controller 11B and a projection time (timing t1 in the figure) of laser light LS2 from laser diode LD2 for distance measurement. In addition, reflected light RV2 of laser light LS2 is received by photodiode PD0 in received light processor SA, and distance calculator 274 determines an input time of an output from a comparator/peak-hold processor in amplifier circuit 262, as a light receiving time (timing t2 in the figure) of reflected light RM. For example, distance calculator 274 calculates the distance in a relationship of "distance=light speed× (temporal difference Δt/2)" and can simply derive the distance from invisible light sensor NVSS to the specific substance.

Substance detection processor 273 as an example of a substance detector determines whether the specific substance is detected, based on an output from AD conversion circuit 271 corresponding to reflected light RV1 of laser light LS1 that is emitted from laser diode LD1 for gas detection, and the substance detection processor outputs the signal indicating the detected specific substance to display processor 28.

Display processor 28 as an example of an image generator generates substance position image data indicating the two-dimensional position of the specific substance in detection region SAR, which is viewed from invisible light sensor NVSS, based on the signal indicating the detected specific substance. The substance position image data includes image data indicating the specific substance and two-dimensional position information (for example, the pan angle and the tilt angle of camera platform 10) in detection region SAR. Display processor 28 outputs the substance position image data to display controller 37 of visible light camera VSC.

For example, in the fifth embodiment, display processor 28 may directly transmit the substance position image data to monitor 150, or camera server CS, which will be described below, or a communication terminal, instead of transmitting the data to display controller 37 in visible light camera VSC.

As described above, display data obtained by synthesizing information associated to the specific substance which is obtained by detection processor 27B with the visible light image data obtained in detection region SAR is output. Hence, invisible light sensor NVSS can visually and clearly show a user where the specific substance is present in detection region SAR.

As illustrated in FIG. 45, visible light camera VSC includes condenser V31, image sensor V33, signal processor V35, display controller 37, and output 38. Processor V20 executes a program stored in the memory, and thereby the functions of signal processor V35 and display controller 37 are realized.

Condenser V31 condenses incident light (reflected light RM) from outside in a range including detection region SAR, as a range of an angle of view, by invisible light sensor NVSS, and forms an image on a capturing surface of image sensor V33.

Image sensor V33 is a capturing element that has the peak of spectral sensitivity with respect to the wavelength (for example, 0.4 μm to 0.7 μm) of visible light. Image sensor V33 converts an optical image formed on the capturing surface into an electric signal. Output from image sensor V33 is input as the electric signal into signal processor V35.

Signal processor V35 generates visible light image data defined by RGB (red, green, and blue), YUV (luminance/ color difference), or the like by using the electric signal output from image sensor V33. In this manner, visible light image data captured by visible light camera VSC is generated. Signal processor V35 outputs the visible light image data to display controller 37.

For example, in a case where the specific substance is detected at a predetermined position from the visible light image data, display controller 37 synthesizes the visible light image data output from signal processor V35 with the substance position image data output from display processor 28 and generates display data. The display data is an example of information associated with the specific substance.

Output 38 as an example of an image output outputs the display data to external devices (for example, camera server CS and monitor 150).

Camera server CS transmits, to a communication terminal or one or more externally connected devices, the display data output from display controller 37 and promotes display of the display data on a display screen of the communication terminal or one or more externally connected devices. Monitor 150 displays the display data output from display controller 37.

Figure 49:
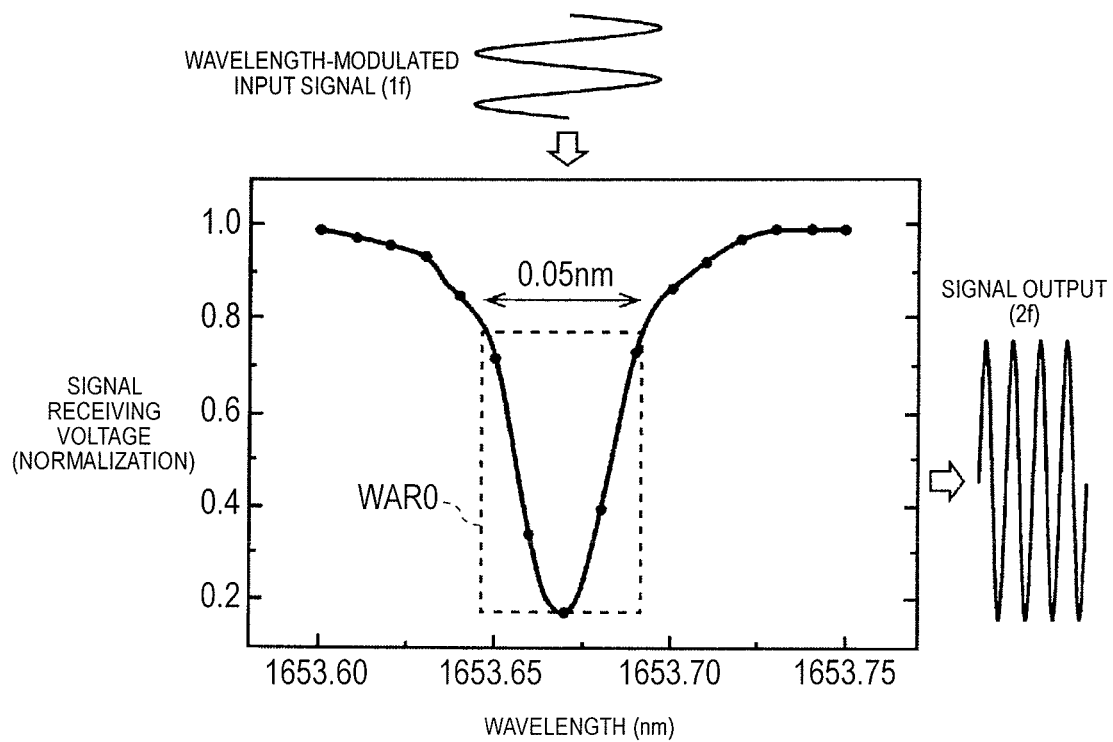
FIG. 49 is a diagram illustrating an example of an input signal and an output signal of laser light in a case where an oscillation frequency of a laser diode is in an optimal range with respect to absorption spectra of a specific substance.

FIG. 49 is a diagram illustrating an example of the input signal and the output signal of laser light in a case where an oscillation frequency of a laser diode is in an optimal range with respect to absorption spectra of a specific substance. FIG. 49 illustrates an output signal of laser light that is reflected from the specific substance and is received by the photodiode with respect to an input signal of the laser light that is emitted from laser diode and is subjected to the wavelength modulation.

In addition, an example of the gas which is the detection target substance includes methane gas (CH4). In FIG. 49, the vertical axis represents light receiving voltage (unit is a normalized value) corresponding to an output from I/V conversion circuit 261, which corresponds to reflected light received by photodiode PD, and the horizontal axis represents a wavelength (nm) of the laser light which is received by photodiode PD. A portion, in which the light receiving voltage is significantly reduced, is a unique energy absorbing region of the specific substance, that is, a wavelength band having a high absorption rate of the laser light.

In FIG. 49, the absorption spectra of the specific substance have a wavelength band having the center thereof at 1,653.67 nm. On the other hand, the laser light emitted from laser diode LD1 is modulated in a modulation width of 0.05 nm in which the center wavelength is at 1,653.67 nm as shown in wavelength modulating range WAR0.

As described above, the reflected light of laser light emitted from laser diode LD1, which is reflected from the specific substance in detection region SAR or is reflected from background after being transmitted through the specific substance, is detected as an output signal which has constant amplitude and the frequency (2f) twice the input signal of laser light subjected to the wavelength modulation as a sine wave having the constant frequency (1f).

Figure 50:
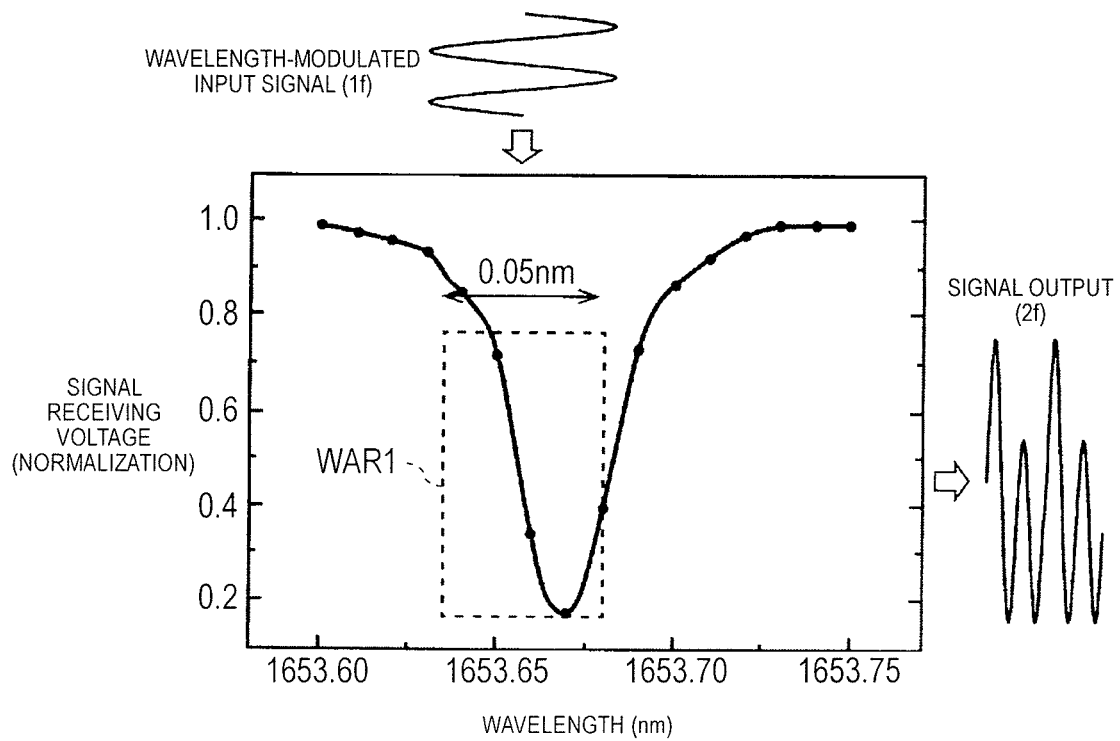
FIG. 50 is a diagram illustrating an example of the input signal and the output signal of the laser light in a case where an oscillation frequency of a laser diode is shifted to the side of a short wavelength from an oscillation frequency in the optimal range with respect to absorption spectra of a specific substance.

FIG. 50 is a diagram illustrating an example of the input signal and the output signal of the laser light in a case where an oscillation frequency of laser diode LD1 for gas detection is shifted to the side of a short wavelength from an oscillation frequency in the optimal range, with respect to absorption spectra of the specific substance.

In FIG. 50, for example, laser light LS1 is subjected to the wavelength modulation in the modulation width of 0.05 nm having the center wavelength at 1,653.66 nm as shown in wavelength modulating range WAR1. The reflected light in this case is detected as an output signal that has the frequency (2f) twice the frequency and does not have constant amplitude.

Figure 51:
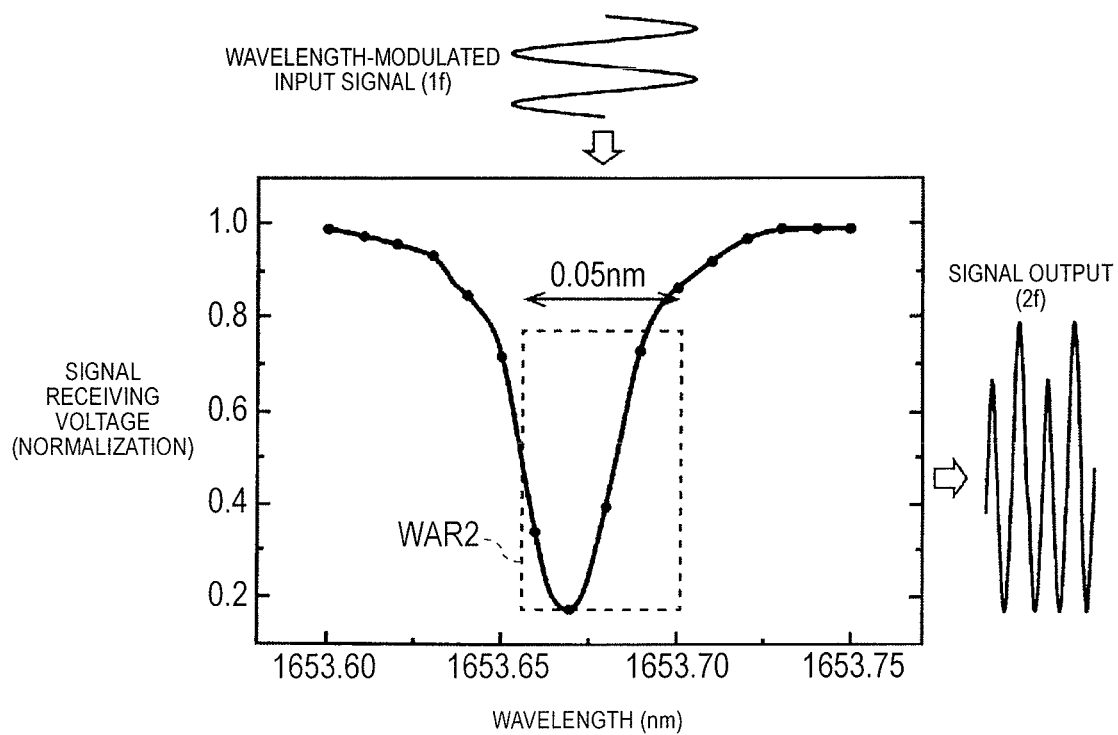
FIG. 51 is a diagram illustrating an example of the input signal and the output signal of the laser light in a case where the oscillation frequency of the laser diode is shifted to the side of a long wavelength from an oscillation frequency in the optimal range with respect to absorption spectra of a specific substance.

FIG. 51 is a diagram illustrating an example of the input signal and the output signal of the laser light in a case where an oscillation frequency of laser diode LD1 for gas detection is shifted to the side of a long wavelength from an oscillation frequency in the optimal range, with respect to absorption spectra of the specific substance.

In FIG. 51, for example, laser light LS1 is subjected to the wavelength modulation in the modulation width of 0.05 nm having the center wavelength at 1,653.68 nm as shown in wavelength modulating range WAR2. The reflected light in this case is detected as an output signal that has the frequency (2f) twice the input signal and does not have constant amplitude.

As illustrated in FIGS. 50 and 51, in a case where the wavelength of the laser light emitted from laser diode LD1 is shifted to the side of the short wavelength or the side of the long wavelength, a signal having a change in amplitude is output. The change in amplitude is represented as a state in which the wavelength of laser light LS1 and the center wavelength of the energy absorption region of the specific substance are shifted. The wavelength of laser light LS1 depends on the temperature of laser diode LD1. Therefore, when the wavelength is significantly shifted due to a change in temperature, an output signal having the frequency (2f) twice the input signal of laser light is not output. In other words, it is difficult to detect the specific substance. Therefore, it is preferable that temperature control is performed so as to maintain the constant temperature of laser diode LD1 such that the output signal having the frequency (2f) twice the input signal of laser light LS1 has constant amplitude. In this manner, detection camera 1D can detect the output signal having the frequency (2f) that has stable amplitude and is twice the input signal of laser light LS1, and accuracy of the substance detection is improved.

An operation of detection camera 1D having the configuration described above is described.

Figure 52:
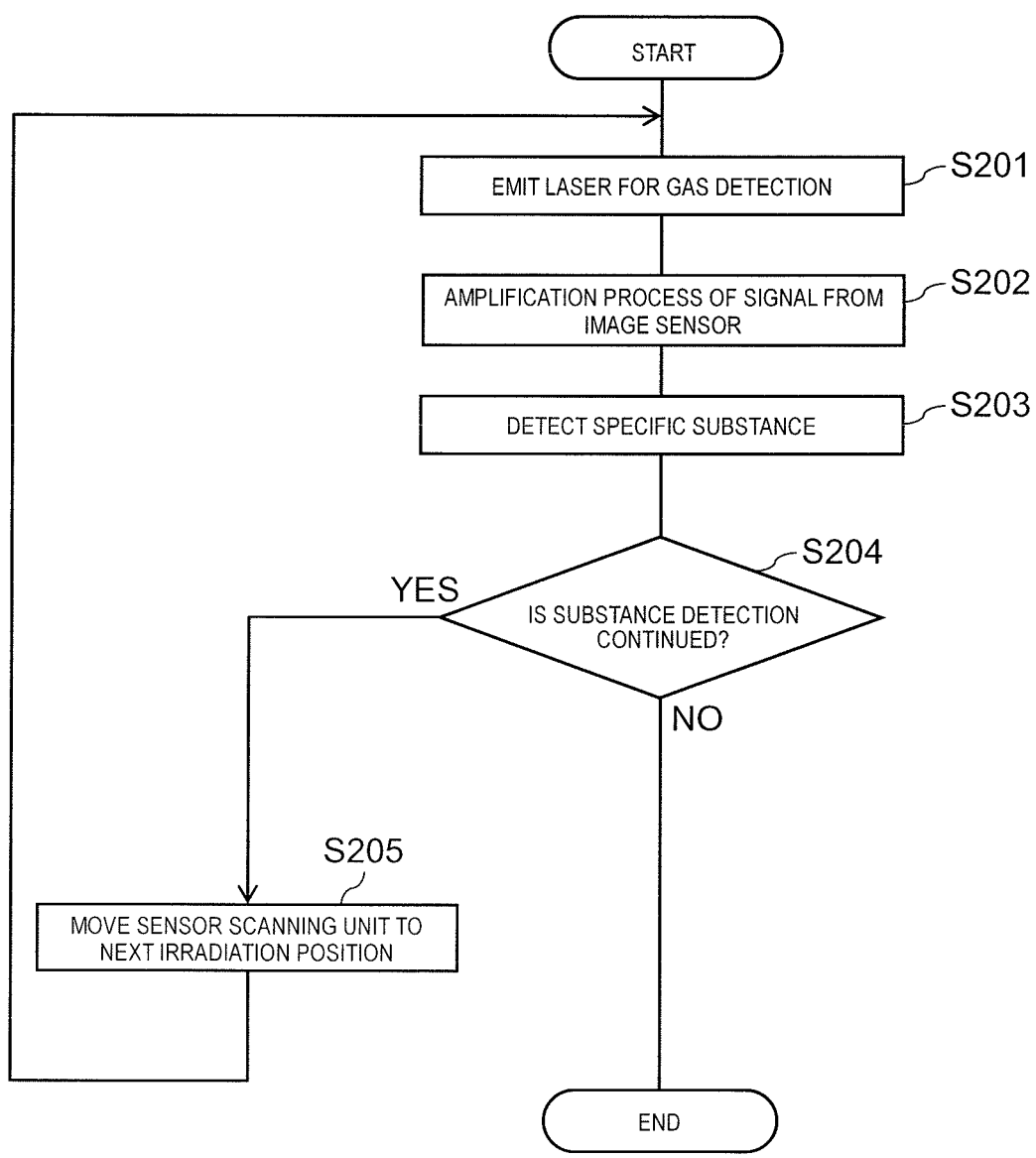
FIG. 52 is a flowchart illustrating an example of a signal processing procedure of the invisible light sensor in a comparative example.

At the beginning, signal processing of the invisible light sensor in a comparative example is described. In the comparative example, a case where two-dimensional scanning is simply performed with laser light in detection region SARm is described. FIG. 52 is a flowchart illustrating an example of a signal processing procedure of the invisible light sensor in the comparative example. In FIG. 52, when the laser light is emitted from the laser diode for gas detection to the irradiation position in detection region SARm (S201), the reflected light reflected from gas GS which is the specific substance is received by photodiode PD0 in a case where the specific substance is present at the irradiation position in detection region SARm. When the output signal from photodiode PD0 is subjected to various types of signal processing including amplification processing in received light processor SA (S202), the presence or absence of gas GS that is the specific substance is detected (S203).

Then, whether or not the substance detection is continued is determined (S204). In a case where the substance detection is continued, sensor scanning unit 5M moves to the next irradiation position (S205). The processes from Step S201 are repeated. On the other hand, in a case where the substance detection is not continued, the signal processing of invisible light sensor NVSS is ended as it is.

Figure 53:
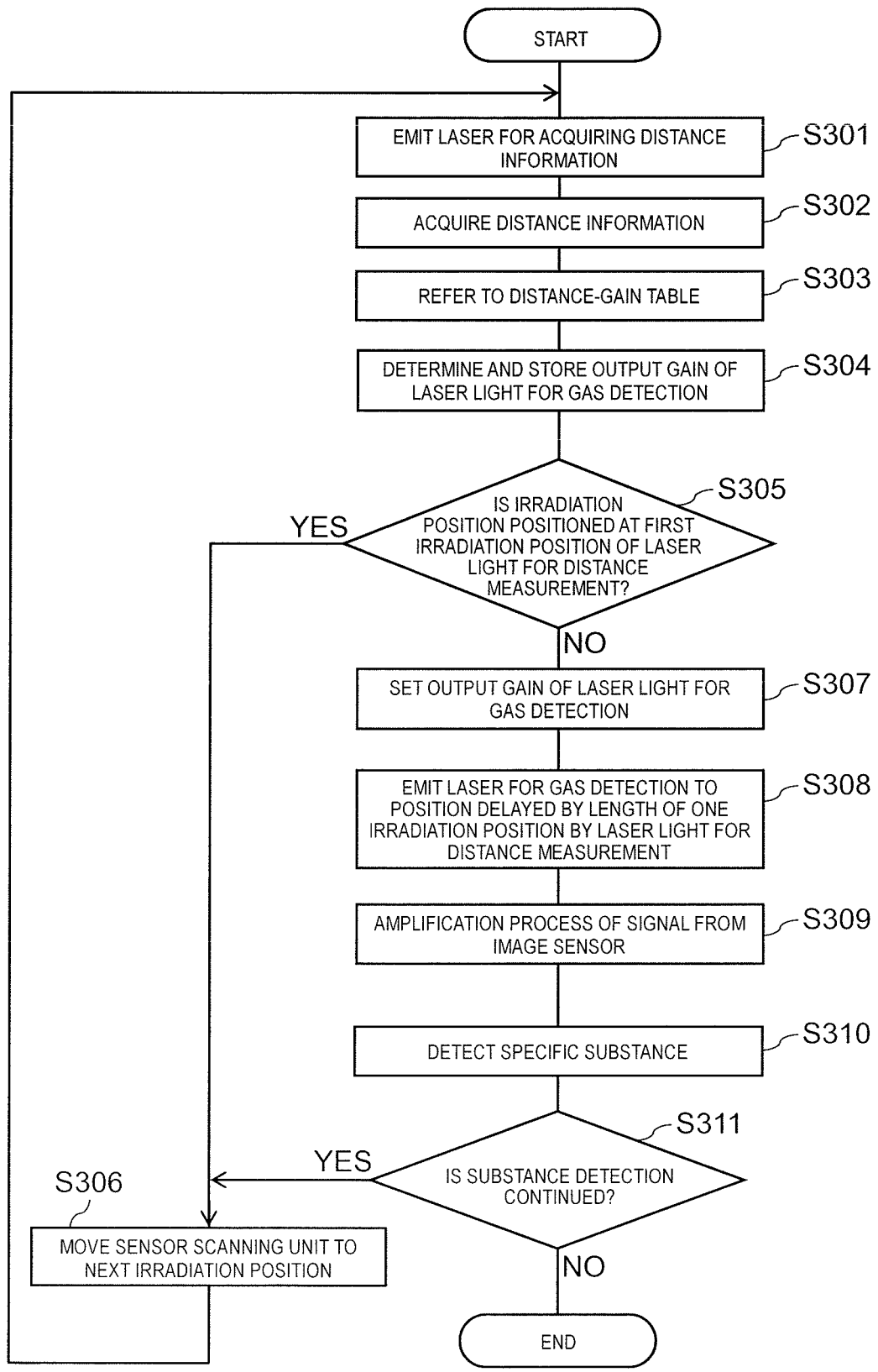
FIG. 53 is a flowchart illustrating an example of the signal processing procedure of the invisible light sensor in the fifth embodiment.

FIG. 53 is a flowchart illustrating an example of the signal processing procedure of invisible light sensor NVSS in the fifth embodiment. In FIG. 53, modulation signal generator 113 in controller 11B outputs the light source light-emitting signal to laser diode LD2 for distance measurement and emits laser light LS2 toward the irradiation position in detection region SAR (S301). When photodiode PD0 receives reflected light RV2 of laser light LS2 reflected at the irradiation position in detection region SAR, distance calculator 274 in received light processor SA calculates a distance from sensor scanning unit 5B to the irradiation position in detection region SAR and acquires distance information (S302).

When signal gain adjustor 114 in controller 11B receives the distance information from distance calculator 274, the output gain corresponding to the distance calculated in Step S302 is acquired, based on table 14z (S303), and the output gain is temporarily stored in memory 14y so as to be used as the output gain of laser light LS1 for gas detection (S304).

Controller 11B determines whether or not the irradiation position of laser light LS2 that is emitted from laser diode LD2 for distance measurement is the first irradiation position (S305).

In a case where the irradiation position is the first irradiation position (S305, YES), two-dimensionalization unit controller 112 in controller 11B causes sensor scanning unit 5B to move such that the irradiation position can be irradiated with laser light LS1 and LS2 (S306). Then, controller 11B performs the process in Step S301, and the same process is repeatedly performed.

On the other hand, in a case where the irradiation position of laser light LS2 emitted from laser diode LD2 for distance measurement is not the first irradiation position (S305, NO), signal gain adjustor 114 acquires the output gain corresponding to the distance information stored in memory 14y based on table 14z, and the output gain is set to laser diode LD1 for gas detection (S307).

Figure 54C:
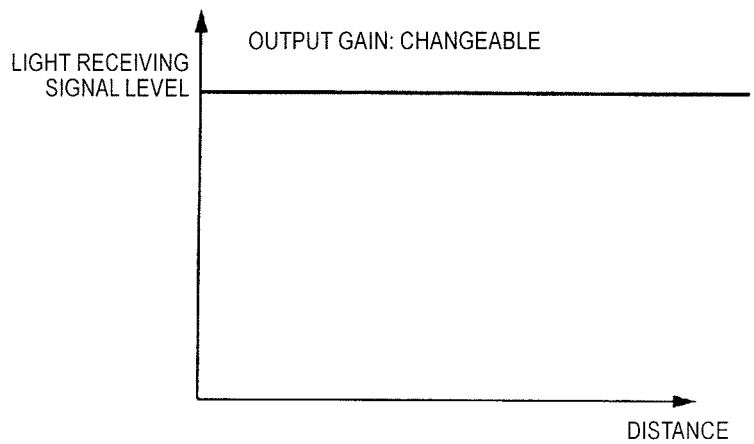
FIG. 54C is a graph illustrating an example of a relationship between the distance to the detection target gas and the signal level of the reflected light obtained by reflection from the gas in a case where the output gain of the laser light for gas detection is changeable in the detection camera in the fifth embodiment.

Here, a relationship between the output gain and the light receiving signal level is considered. FIGS. 54A, 54B, and 54C all illustrate graphs showing a change in light receiving signal level depending on the distance. FIG. 54A illustrates a change in the light receiving signal level in a case where the output gain is set to be low. In this case, when the distance to the irradiation position is a short distance, the photodiode obtains a signal having a high light receiving level; however, the intensity of laser light from laser diode is reduced at a long distance, and thus a signal having a light receiving level, at which it is possible to detect gas, is not obtained.

FIG. 54B illustrates a change in the light receiving signal level in a case where the output gain is set to be high. In this case, even when the distance to the irradiation position is a long distance, the photodiode obtains the signal having the light receiving level at which it is possible to detect the gas; however, the signal having the light receiving level is saturated at a short distance, and thus the signal having a high light receiving level is not obtained.

In this respect, in the fifth embodiment, as illustrated in FIG. 54C, the appropriate output gain corresponding to the distance to the irradiation position is set. FIG. 54C is a graph illustrating an example of a relationship between the distance to gas GS that is the detection target and the signal level of reflected light RV1 reflected from gas GS, in a case where the output gain of laser light LS1 for gas detection is changeable in detection camera 1D of the fifth embodiment. In other words, the output gain is set such that the signal level of light received by photodiode PD0 is in a range from the short distance to the long distance of the distance to the irradiation position. The output gain of laser light LS1 emitted from laser diode LD1 for gas detection is set to an appropriate value depending on the distance to the irradiation position, which is set in table 14z, and thereby photodiode PD0 can obtain a signal having substantially constant light receiving level even when the irradiation position in detection region SAR is within the range from the short distance to the long distance. The output gain of laser diode LD2 for distance measurement is a relatively large value as described above, and may be a constant value.

Modulation signal generator 113 enables the spot irradiation to be performed, with laser light LS1 for gas detection from laser diode LD1 for gas detection, on the irradiation position irradiated with laser light LS2 from laser diode LD2 for distance measurement in the previous spot irradiation (S308). In other words, the spot irradiation is performed with laser light LS1 for gas detection that is delayed by a length of one irradiation position, compared to laser light LS2 for distance measurement. In addition, the spot irradiation with laser light LS1 for gas detection is performed at the same time as modulation signal generator 113 performs spot irradiation with laser light LS2 for distance measurement from laser diode LD2 for distance measurement. In other words, the spot irradiation is performed with laser light LS2 for distance measurement that is ahead of laser light LS1 for gas detection by a length of one irradiation position.

Received light processor SA performs various types of signal processing including the amplification processing with respect to the output from photodiode PD0 (S309). Substance detection processor 273 detects the presence or absence of gas GS that is the specific substance depending on the result of the various types of signal processing and the presence or absence of the output signal having the frequency (2f) twice the input signal described above (S310).

Then, controller 11B determines whether or not the substance detection is continued (S311). In a case where the substance detection is continued, two-dimensionalization unit controller 112 in controller 11B causes sensor scanning unit 5B to move in Step S306 such that the next irradiation position can be irradiated with laser light LS1 and LS2. Then, controller 11B makes the procedure return to the process in Step S301, and the same process is repeatedly performed. On the other hand, in a case where the substance detection is not continued, controller 11B ends the signal processing of invisible light sensor NVSS.

In a case where gas GS that is the specific substance is detected in Step S310, as described above, display processor 28 generates an image (substance position image data) including gas GS that is the specific substance. The generated image including gas GS that is the specific substance is superimposed on a visible light image captured with visible light camera VSC by display controller 37. A synthesized image obtained by superimposing the image including gas GS, which is the specific substance, on the visible light image is displayed on monitor 150.

Figure 55:
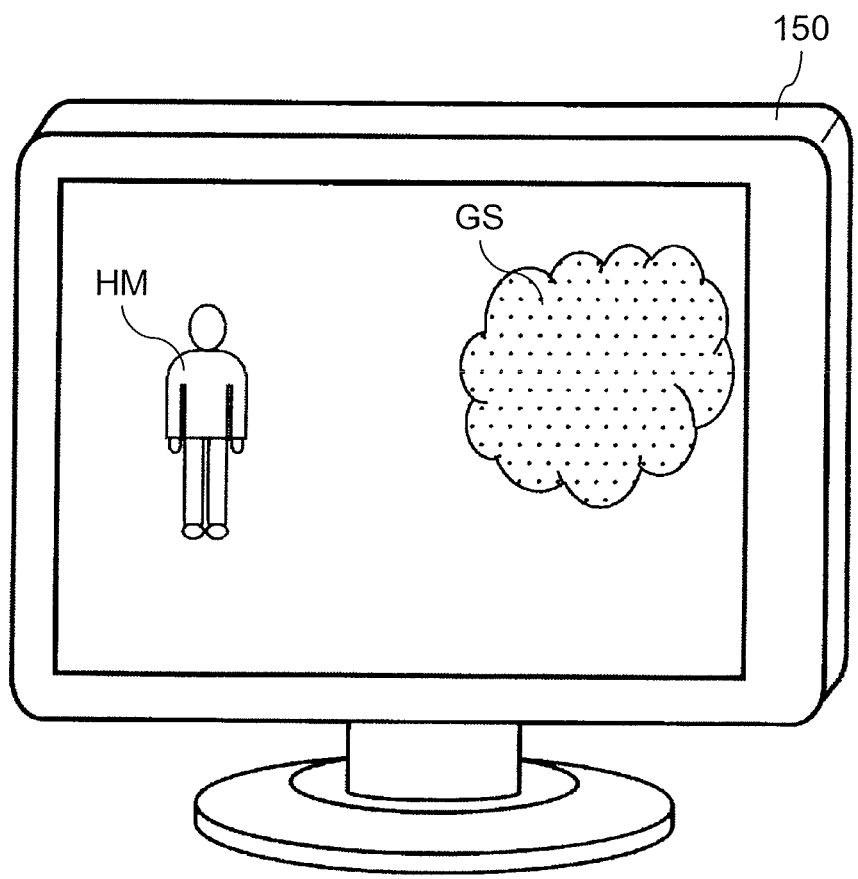
FIG. 55 is a diagram illustrating an example of a display screen of a monitor.

FIG. 55 is a diagram illustrating an example of a display screen of monitor 150. Monitor 150 superimposes the image including gas GS which is the specific substance detected by invisible light sensor NVSS on the visible light image (image including a human HM) captured by visible light camera VSC and displays the superimposed image. In this manner, a user can visually recognize gas GS displayed on monitor 150.

As described above, in detection camera 1D of the fifth embodiment, laser diode LD1 for gas detection emits laser light LS1 having the wavelength for gas detection to a detection area (detection region (SAR). Laser diode LD2 for distance measurement emits laser light LS2 for distance measurement to detection region SAR. Distance calculator 274 measures the distance to the irradiation position based on laser light RV2 reflected at the irradiation position in detection region SAR. Signal gain adjustor 114 adjusts the output gain of laser light LS1 for gas detection with respect to the distance measured by distance calculator 274. Substance detection processor 273 detects the presence or absence of gas, based on reflected light RV1 from the irradiation position with laser light LS1 for gas detection of which the output gain is adjusted. When detection region SAR is scanned with laser light LS1 and laser light LS2, detection camera 1D causes laser light LS2 to be ahead of laser light LS1.

In this manner, detection camera 1D can easily detect the gas (substance) in the two-dimensional detection area (detection region SAR). In addition, since the output gain of laser light LS1 for gas detection is adjusted depending on the distance to the irradiation position, detection camera 1D can detect the gas from a short distance to a long distance and can broaden the region in detection region SAR, in which it is possible to detect the gas.

In addition, in detection camera 1D, since the irradiation position, on which the spot irradiation is performed ahead with laser light LS2 for distance measurement, is subjected to the spot irradiation with laser light LS1 for gas detection, detection camera 1D can set the output gain of laser light LS1 for gas detection to an appropriate value depending on the distance. Hence, detection camera 1D can enhance the accuracy of the gas detection. In addition, it is possible to continuously perform the distance measurement and the gas detection, and it is possible to perform efficient gas detection.

In addition, detection camera 1D swivels camera platform 10 to which laser diode LD1 for gas detection and laser diode LD2 for distance measurement are fixed, and thereby scanning is performed with laser light LS1 for gas detection and laser light LS2 for distance measurement in pan direction P and tilt direction T. Therefore, the control of scanning with the laser light is simply and efficiently performed.

In addition, laser diode LD1 for gas detection and laser diode LD2 for distance measurement are fixed to camera platform 10 so as to perform spot irradiation in which the irradiation position is shifted by a length of one irradiation position. Therefore, control of spot irradiation with laser light LS1 for gas detection and laser light LS2 for distance measurement in which the irradiation position is shifted by a length of one irradiation position is simply performed.

In addition, when scanning is performed forward and backward with laser light LS1 for gas detection and laser light LS2 for distance measurement in pan direction P, the irradiation position, on which the spot irradiation is performed ahead with laser light LS2 for distance measurement, is subjected to the spot irradiation with laser light LS1 for gas detection also in a scanning direction of both of the forward direction and the backward direction. Therefore, the output gain of laser light LS1 for gas detection is set to an appropriate value depending on the distance in every direction. In addition, the gas detection is performed in a reciprocating manner, it is possible to shorten time to perform gas detection.

In addition, since detection camera 1D generates an image of the detected gas and outputs the image, it is possible to visualize the detected gas.

In addition, since the image of the gas is superimposed on the captured visible light image and is displayed on monitor 150, a user looks at the screen of monitor 150 and can visually recognize the position of the gas on the visible light image.

As described above, embodiments are described with reference to the accompanying figures; however, it is needless to say that the present invention is not limited to the examples. It is obvious for those skilled in the art to conceive various modification examples or alteration examples within the range of the claims, and thus it is understood that the examples belongs to the technical scope of the present invention.

For example, in the embodiments described above, spot irradiation with laser light LS1 for gas detection and laser light LS2 for distance measurement is performed in which the irradiation position is shifted by a length of one irradiation position; however, as long as spot irradiation with laser light LS1 for gas detection and laser light LS2 for distance measurement is performed on the irradiation position and the spot irradiation is again performed on the irradiation position, the spot irradiation may be performed in which the irradiation position is shifted by a length longer than two irradiation positions. In addition, the configuration is not limited to a case where spot irradiation with laser light LS1 for gas detection and laser light LS2 for distance measurement is performed such that the scanning is performed, the scanning may be performed while continuous irradiation is performed.

In addition, in the embodiments described above, an example of the specific substance includes methane gas (CH4); however, another substance may be used regardless of gases, liquids, or solids. Table 1 shows the specific substance that can be detected by invisible light sensor NVSS and a wavelength used to detect the specific substance. In this manner, invisible light sensor NVSS can detect large types of specific substances by using the wavelength corresponding to individual specific substances and can generate the substance position image data indicating that the specific substances are detected.

TABLE 1

| Specific substance | Major use wavelength |
| --- | --- |
| Chlorophyll | 0.44 μm, 0.68 μm |
| Hemoglobin (HB) | 0.66 μm |
| Protein | 1.19 μm |
| Water (H2O) | 1.45 μm |
| Plastics | 1.7 μm |
| Sugar | 2.1 μm |
| Carbon dioxide (CO2) | 2.8 μm |
| Methane gas (CH4) | 3.3 μm |

As described above, this disclosure is described based on the specific embodiments; however, the embodiments are just examples, and this disclosure is not limited to the embodiments. There is no need to absolutely include all of the constituent elements of the substance detecting device, the substance detecting system, and the substance detecting method according to this disclosure which are described in the embodiment, and it is possible to appropriately perform selection thereof without departing from at least the scope of this disclosure.

INDUSTRIAL APPLICABILITY

This disclosure is applicable to the substance detecting device, the substance detecting system, the substance detecting method, and the like in which it is possible to easily detect the substance in the detection region. In addition, this disclosure is applicable to the substance detecting device, the substance detecting method, and the like in which it is possible to improve the detection accuracy of the substance in the detection region. In addition, this disclosure is applicable to the substance detecting device, the substance detecting system, and the substance detecting method in which it is possible to easily detect, with fine resolution, the substance that is difficult to be visible through imaging with visible light in the detection region, without user's significant effort.

REFERENCE MARKS IN THE DRAWINGS 1, 1A, 1B DETECTION CAMERA
1w OPENING
1z HOUSING
5, 5B, 5M SENSOR SCANNING UNIT
10 CAMERA PLATFORM
11, 11A, 11B CONTROLLER
12, 12A WAVELENGTH DETECTION/TEMPERATURE CONTROLLER
14y MEMORY
14z TABLE
15 PAN/TILT UNIT
20 PROCESSOR
26, 26B SIGNAL PROCESSING UNIT
27, 27A, 27B DETECTION PROCESSOR

28 DISPLAY PROCESSOR
30 TEMPERATURE CONTROLLING UNIT
31 I/V CONVERSION CIRCUIT
32 AMPLIFIER CIRCUIT
33 FILTER PROCESSING CIRCUIT
37 DISPLAY CONTROLLER
38 OUTPUT
112 TWO-DIMENSIONALIZATION UNIT CONTROLLER
113 MODULATION SIGNAL GENERATOR
114 SIGNAL GAIN ADJUSTOR
150 MONITOR
261 I/V CONVERSION CIRCUIT
262 AMPLIFIER CIRCUIT
263 FILTER PROCESSING CIRCUIT
271 AD CONVERSION CIRCUIT
272 TEMPERATURE CONTROLLING PROCESSOR
273 SUBSTANCE DETECTION PROCESSOR
274 DISTANCE CALCULATOR
AX1, AX2 LENS ROTATION SHAFT
CEL REFERENCE CELL
CLZ, CLZ2, V31 CONDENSER
CS CAMERA SERVER
D1a, D1b, D2a, D2b ARROW
DS SIGNAL PROCESSOR
F1a, F1b, F2a, F2b FORCE
EP SCAN END POSITION
FIR ND FILTER
GS GAS
HM HUMAN
HP INITIAL POSITION
K DETECTION SPACE
KL1a, KL1b, KL2a, KL2b COIL
LD1, LD2 LASER DIODE
LS, LS1, LS2, RV, RV1, RV2 LASER LIGHT
Mg1a, Mg1b, Mg1c, Mg1d, Mg2a, Mg2b, Mg2c, Mg2d MAGNET
MR1 REFLECTIVE PLATE
NVSS INVISIBLE LIGHT SENSOR
OP1 PROJECTION LIGHT SOURCE OPTICAL PORTION FOR GAS DETECTION
OP2 PROJECTION LIGHT SOURCE OPTICAL PORTION FOR DISTANCE MEASUREMENT
PD, PD0, PD2 PHOTODIODE
PJ PROJECTOR
PLZ, PLZ1, PLZ2 COLLIMATOR LENS
Pt PELTIER ELEMENT
RM REFLECTED LIGHT
RP LIGHT RECEIVER
SA RECEIVED LIGHT PROCESSOR
SAR, SARm DETECTION REGION
SP1, SP2, SP11, SP12, SP21, SP22, SP23 IRRADIATION POSITION
T1 PERIOD
V20 PROCESSOR
V33 IMAGE SENSOR
V35 SIGNAL PROCESSOR
VSC VISIBLE LIGHT CAMERA
WAR0, WAR1, WAR2 WAVELENGTH MODULATING RANGE

The invention claimed is:
1. A substance detecting device, comprising:
a transmitter that emits, through wavelength modulation, wavelength-modulated infrared light having a first wavelength as a center wavelength;
at least one photodiode that receives reflected light of the wavelength-modulated infrared light, the reflected light being reflected inside a detection region of a detection target substance;
a detector that detects the detection target substance, based on the reflected light;
an actuator that changes an emitting direction of the wavelength-modulated infrared light and a receiving direction of the reflected light;
the at least one photodiode that receives passing light from the wavelength-modulated infrared light passing through a reference cell, the reference cell storing a reference target substance and being in an adjustment controlling region outside the detection region, the reference target substance being same as the detection target substance; and
a processor that adjusts a temperature of the transmitter to control the first wavelength to be centered within an absorption spectra of the detection target substance such that an output from the at least one photodiode, which receives the passing light, has a frequency twice a modulation frequency of the first wavelength-modulated infrared light and such that the frequency is constant.

2. The substance detecting device of claim 1,
wherein the transmitter and the at least one photodiode are fixed to a base, and
wherein the transmitter scans the inside of the detection region and the adjustment controlling region outside of the detection region by using the wavelength-modulated infrared light with an orientation of the base being changed by the actuator.

3. The substance detecting device of claim 1, further comprising:
a reflector that is disposed in the adjustment controlling region and reflects the wavelength-modulated infrared light; and
a filter that attenuates light of the wavelength-modulated infrared light reflected from the reflector,
wherein the at least one photodiode receives, as the passing light, light passing through the reference cell after the light is attenuated by the filter.

4. The substance detecting device of claim 1, further comprising:
a diffuser that is disposed in the adjustment controlling region and diffuses the wavelength-modulated infrared light,
wherein the at least one photodiode receives, as the passing light, light passing through the reference cell after the light is diffused by the diffuser.

5. The substance detecting device of claim 1,
wherein the transmitter emits the wavelength-modulated infrared light to each position inside the detection region and, then, emits the wavelength-modulated infrared light to the adjustment controlling region by driving of the actuator.

6. The substance detecting device of claim 1,
wherein the transmitter emits the wavelength-modulated infrared light to positions adjacent to each other in a predetermined direction in the detection region and, then, emits the wavelength-modulated infrared light to the adjustment controlling region by driving of the actuator.

7. The substance detecting device of claim 1,
wherein the processor changes a modulation frequency of the wavelength-modulated infrared light and a detection frequency corresponding to the modulation frequency for detecting the detection target substance by the detector.

8. The substance detecting device of claim 7,
wherein the transmitter emits the wavelength-modulated infrared light a plurality of times in the detection region,
wherein the at least one photodiode receives the reflected light the plurality of times in the detection region,
wherein the detector repeats a detection operation for detecting the detection target substance the plurality of times in the detection region, and
wherein the controller changes the modulation frequency and the detection frequency for every detection operation in the detection region, for each detection operation on a line parallel to a predetermined direction in the detection region, or for each region in the detection region.

9. The substance detecting device of claim 8,
wherein the detector repeats detection of the detection target substance in an arbitrary region in the detection region by using a first detection frequency and a second detection frequency, determines that the detection target substance is present in the arbitrary region in a case where the detection target substance is detected in both cases of using the first detection frequency and the second detection frequency, and determines that the detection target substance is not present in the arbitrary region in a case where a detection result of the detection target substance, which is obtained by using the first detection frequency, is different from a detection result of the detection target substance, which is obtained by using the second detection frequency.

10. The substance detecting device of claim 9,
wherein the detector detects the detection target substance by using the first detection frequency and detects the detection target substance by using the second detection frequency, one time in a same region.

11. The substance detecting device of claim 1, further comprising:
a light source that emits, to the detection region, distance measuring light having a wavelength for distance measurement;
a calculator that measures a distance to an irradiation position, based on reflected distance measuring light obtained after the distance measuring light is reflected from the irradiation position in the detection region;
a gain adjustor that adjusts output gain of the wavelength-modulated infrared light in response to a measurement result from the calculator; and
a substance detector that detects a presence or an absence of the detection target substance inside the detection region, based on reflected light obtained after the wavelength-modulated infrared light, subjected to adjustment of the output gain by the gain adjustor, is reflected from the irradiation position,
wherein, in scanning with the wavelength-modulated infrared light and the distance measuring light inside the detection region, a first irradiation position that is irradiated with the distance measuring light is irradiated temporally ahead of a second irradiation position that is irradiated with the wavelength-modulated infrared light.

12. The substance detecting device of claim 11,
wherein, when the scanning is performed in a predetermined direction with emission of the wavelength-modulated infrared light and emission of the distance measuring light to the detection region, the transmitter emits the wavelength-modulated infrared light such that an irradiation position of the previous distance measuring light is irradiated with the wavelength-modulated infrared light.

13. The substance detecting device of claim 12, further comprising:
an irradiation controller that causes an irradiation direction of the wavelength-modulated infrared light and an irradiation direction of the distance measuring light to intersect during switching of scanning directions such that the irradiation position of the distance measuring light is irradiated ahead of the irradiation position of the wavelength-modulated infrared light by a length of one irradiation position in both scanning directions of a forward direction and a backward direction, when the emission of the wavelength-modulated infrared light and the emission of the distance measuring light to the detection region are performed forward and backward in the predetermined direction and scanning is performed.

14. A substance detecting system comprising:
the substance detecting device of claim 1;
a camera that captures a visible light image of the detection region; and
a display that displays image data output by the substance detecting device,
wherein the substance detecting device further includes
the processor that visualizes a position inside the detection region of the detection target substance and generates superimposed image data obtained by superimposing visualized information on visible light image data of the visible light image, and
an output that outputs the superimposed image data on the display.

15. The substance detecting device of claim 1, further comprising:
a sensor that captures a visible light image of the detection region;
the processor that visualizes a position inside the detection region of the detection target substance and generates a superimposed image obtained by superimposing visualized information on the visible light image; and
an output that outputs the superimposed image.

16. A substance detecting method used in a substance detecting device, the substance detecting method comprising:
emitting, by a transmitter and through wavelength modulation, wavelength-modulated infrared light having a first wavelength as a center wavelength;
receiving reflected light of the wavelength-modulated infrared light, the reflected light being reflected inside a detection region of a detection target substance;
detecting the detection target substance, based on the reflected light;
changing an emitting direction of the wavelength-modulated infrared light and a receiving direction of the reflected light;
receiving, by a photodiode, passing light from the wavelength-modulated infrared light that passes through a reference cell, the reference cell storing a reference target substance and being in an adjustment controlling region outside the detection region, the reference target substance being same as the detection target substance; and adjusting a temperature of the transmitter to control the first wavelength to be centered within an absorption spectra of the detection target substance such that an output from the photodiode, which receives the passing light, has a frequency twice a modulation frequency of the wavelength-modulated infrared light and such that the frequency is constant.

17. The substance detecting method of claim 16, further comprising:
changing an emitting direction of the wavelength-modulated infrared light and a receiving direction of the reflected light, inside the detection region;
changing a modulation frequency of the wavelength modulation of the wavelength-modulated infrared light and a detection frequency corresponding to the modulation frequency for detecting the detection target substance;
emitting the wavelength-modulated infrared light subjected to a change in wavelength frequency, to the inside of the detection region;
receiving the reflected light of the wavelength-modulated infrared light subjected to the change in the modulation frequency inside the detection region; and
detecting the detection target substance, based on wavelength characteristics of reflected light corresponding to the modulation frequency of the wavelength-modulated infrared light subjected to the change in the modulation frequency.

18. The substance detecting method of claim 16 comprising:
emitting distance measuring light having a wavelength for distance measurement, to the detection region;
measuring a distance to an irradiation position, based on reflected distance measuring light obtained after the distance measuring light is reflected from the irradiation position in the detection region;
adjusting output gain of the wavelength-modulated infrared light depending on the distance to the irradiation position obtained by the measuring;
emitting, to the detection region, the wavelength-modulated infrared light subjected to adjustment of the output gain; and
detecting a presence or an absence of the detection target substance inside the detection region, based on reflected light obtained after the wavelength-modulated infrared light subjected to adjustment of the output gain is reflected from the irradiation position,
wherein, in scanning with the wavelength-modulated infrared light and the measuring light inside the detection region, a first irradiation position that is irradiated with the measuring light is irradiated temporally ahead of a second irradiation position that is irradiated with the wavelength-modulated infrared light.

* * * * *